(12) United States Patent  
Patty et al.

(10) Patent No.: US 11,638,601 B2  
(45) Date of Patent: *May 2, 2023

(54) BONE COMPRESSION SYSTEMS

(71) Applicant: Bridging Medical, LLC, Tooele, UT (US)

(72) Inventors: Robert Michael Patty, West Lafayette, IN (US); Andrew Alan Enke, Highland Village, TX (US); Cameron Joseph Field, Highlands Ranch, CO (US); Daniel Robert Patty, Draper, UT (US)

(73) Assignee: BRIDGING MEDICAL, LLC, Tooele, UT (US)

( * ) Notice: Subject to any disclaimer, the term of this patent is extended or adjusted under 35 U.S.C. 154(b) by 137 days.

This patent is subject to a terminal disclaimer.

(21) Appl. No.: 17/074,155

(22) Filed: Oct. 19, 2020

(65) Prior Publication Data

US 2021/0030455 A1 Feb. 4, 2021

Related U.S. Application Data

(63) Continuation of application No. 14/944,197, filed on Nov. 17, 2015, now Pat. No. 10,806,497.

(60) Provisional application No. 62/080,893, filed on Nov. 17, 2014, provisional application No. 62/080,954, filed on Nov. 17, 2014.

(51) Int. Cl.
*A61B 17/86* (2006.01)
*A61B 17/68* (2006.01)
*A61B 17/80* (2006.01)
*F16B 43/00* (2006.01)

(Continued)

(52) U.S. Cl.
CPC ........ *A61B 17/8695* (2013.01); *A61B 17/866* (2013.01); *A61B 17/8014* (2013.01); *A61B 17/8047* (2013.01); *A61B 2017/681* (2013.01); *F16B 43/00* (2013.01); *F16D 13/583* (2013.01); *F16F 1/32* (2013.01)

(58) Field of Classification Search
CPC ............ A61B 17/8695; A61B 17/8047; A61B 17/8028; A61B 17/683; A61B 2017/681; F16F 1/32; F16F 1/324; F16F 1/328; F16F 3/02; F16B 43/33; F16D 13/583
USPC .................................. 267/160–162; 606/294
See application file for complete search history.

(56) References Cited

U.S. PATENT DOCUMENTS 5,496,142 A * 3/1996 Fodor ................... F16B 43/004
411/368
7,462,007 B2 * 12/2008 Sullivan .................. F16B 39/24
411/231

(Continued)

OTHER PUBLICATIONS (eDesignLab. Rondelle Belleville : Empilage Série Et Parallèle, Charge Et Flèche, Nov. 20, 2012, https://web.archive.org/web/20130121192600/http://edesignlab.fr/rondelle-belleville/.; utilizing page archived on Jan. 21, 2013 and machine translated to English, and accessed Sep. 9, 2019 (Year: 2013).*

*Primary Examiner* — Marcela I. Shirsat
(74) *Attorney, Agent, or Firm* — David Meibos; Maywood IP Law

(57) ABSTRACT

Bone compression systems for internal fixation of bone portions include one or more spring washers having ultra high load capacity and ultra low displacement to close diminution gaps that develop in a discontinuity between the bone portions after fixation. The spring washers may be included in implant systems with bone screws and/or bone plates.

16 Claims, 45 Drawing Sheets

(51) Int. Cl.
*F16F 1/32* (2006.01)
*F16D 13/58* (2006.01)

(56) References Cited

U.S. PATENT DOCUMENTS 10,806,497 B2 * 10/2020 Patty .................... A61B 17/866
2016/0278949 A1 * 9/2016 Dillingham ............... A61F 2/54

* cited by examiner

| Name | Outer Diameter, mm (D) | Inner Diameter, mm (d) | Overall Height, mm (H) | Inner Height, mm (h) | Thickness, mm (t) | Ratio of Inner Height to Thickness (h/t) | Ratio of Outer Diameter to Thickness (D/t) | Design State |
|---|---|---|---|---|---|---|---|---|
| 8 x 3.2 x 0.35 | 8.0 | 3.2 | 0.70 | 0.35 | 0.35 | 1.00 | 22.9 | In Standard Range |
| 8 x 3.2 x 0.82 | 8.0 | 3.2 |  |  | 0.82 |  | 9.8 |  |
| 8 x 3.2 x 1.10 | 8.0 | 3.2 |  |  | 1.10 |  | 7.3 |  |
| 8 x 3.4 x 0.82 | 8.0 | 3.4 | 1.02 | 0.20 | 0.82 | 0.24 | 9.8 | Out of Standard Range |
| 8 x 3.4 x 1.10 | 8.0 | 3.4 | 1.21 | 0.11 | 1.10 | 0.10 | 7.3 |  |
| 8 x 3.4 x 1.10 | 8.0 | 3.4 | 1.23 | 0.13 | 1.10 | 0.12 | 7.3 |  |
| 8 x 3.4 x 1.10 | 8.0 | 3.4 | 1.30 | 0.20 | 1.10 | 0.18 | 7.3 | Out of Standard Range |
|  |  |  |  |  |  | Standard Ratio Ranges (Mubea) | | Design State |
|  |  |  |  |  |  | 0.4 < h/t < 1.3 | 18 < D/t < 40 |  |

Mechanical Properties of 316L Stainless Steel ASTM F138

| Condition | Diameter or Thickness, mm | Ultimate Tensile Strength, min, Mpa | Yield Strength (0.2% offset), min, Mpa | Elongation[A] in 4D or 4W, min, % | Brinell[B] Hardness, max, HB |
|---|---|---|---|---|---|
| Hot-worked[C] | All | | | | 250 |
| Annealed | 1.60 and over | 490 | 190 | 40 | |
| Cold-worked | 1.60 to 38.1 | 860 | 690 | 12 | |
| Extra-hard | 1.60 to 6.35 | 1350 | | | |

[A] 4D = 4 x diameter, 4W = 4 x width. Alternatively, a gage length corresponding to ISO 6892 may be used when agreed upon between supplier and purchaser.

[B] 29-kN load.

[C] Typically supplied as hot-rolled bar for forging applications.

FIG. 3

Mechanical Properties of Titanium ASTM F136

| Nominal Diameter or Distance Between Parallel Sides, mm | Tensile Strength, min, Mpa | Yield Strength (0.2% offset), min, Mpa | Elongation[B] in 4D or 4W, min, % | | | Reduction of Area[C], min, % | | |
|---|---|---|---|---|---|---|---|---|
| | | | L | LT | ST | L | LT | ST |
| Under 4.75 thickness or diameter | 860 | 795 | 10 | | | | | |
| 4.75 to under 44.45, incl | 860 | 795 | 10 | | | 25 | | |
| 44.45 to under 63.50, incl | 825 | 760 | 8 | | | 20 | | |
| 63.50 to 101.60, incl | 825 | 760 | 8 | 8[D] | 8[D] | 15 | 15[D] | 15[D] |
| | Bend Test[E] | | | | | | | |
| Under 1.778 in thickness | 9 T | | | | | | | |
| 1.778 to 4.75, incl | 10 T | | | | | | | |

[A] Mechanical properties for conditions other than those listed in this table may be established by agreement between the supplier and the implant manufacturer.

[B] Elongation of material 1.575 mm or greater in diameter or thickness shall be measured using a gage length of 50.8 mm or 4D or 4W. The gage length must be reported with the test results. Elongation of material under 1.575 mm in diameter or thickness may be obtained by negotiation. L = longitudinal; LT = long transverse; ST = short transverse.

[C] Applies to bar, plate, and forgings only. L = longitudinal; LT = long transverse; ST = short transverse. For round bar the long and short transverse are identical tests, therefore only one transverse is required.

[D] Transverse requirements in this table apply only to product from which a tensile specimen not less than 63.5 mm in length can be obtained.

[E] Bend test applicable to sheet and strip products; T = thickness of bend specimen in reference to diameter of bend.

FIG. 4

Mechanical Properties of Stainless Steel Sold Under the Trademark BIODur 108

| Condition | Diameter or Thickness, mm | Ultimate Tensile Strength, min, Mpa | Yield Strength (0.2% offset), min, Mpa | Elongation in 4D or 4W, min, % | % Reduction in Area |
|---|---|---|---|---|---|
| Annealed[A, B] | All | 931 | 607 | 49 | 70 |
| 10[A, B] | 2.5 mm wire | 1138 | 965 | 33 | 69 |
| 20[A, B] | 2.5 mm wire | 1345 | 1207 | 23 | 68 |
| 30[A, B] | 2.5 mm wire | 1551 | 1413 | 16 | 64 |
| 40[A, B] | 2.5 mm wire | 1689 | 1586 | 12 | 60 |
| 50[A, B] | 2.5 mm wire | 1862 | 1689 | 7 | 53 |
| 60[A, B] | 2.5 mm wire | 2013 | 1793 | 5 | 45 |
| 70[A, B] | 2.5 mm wire | 2124 | 1848 | 4 | 35 |
| 80[A, B] | 2.5 mm wire | 2206 | 1862 | 3 | 23 |
| Annealed[C, D] | 25 mm diameter bar | 931 | 586 | 52 | 75 |
| 10[C, D] | 25 mm diameter bar | 1062 | 786 | 37 | 73 |
| 20[C, D] | 25 mm diameter bar | 1262 | 952 | 25 | 68 |
| 30[C, D] | 25 mm diameter bar | 1496 | 1227 | 19 | 63 |
| 40[C, D] | 25 mm diameter bar | 1731 | 1551 | 12 | 59 |

[A] Data represent wire cold drawn various amounts from a starting diameter of 2.55 mm.
[B] Tests represent full wire section. Elongation values represent a gauge length of 50 mm.
[C] Data represent bar cold drawn various amounts from a starting diameter of 25 mm.
[D] Tests represent 12.8 mm diameter specimens machined from the bar center.

FIG. 5

Disc Springs, Data Sheet
group 1 part./drawing no.:
project:

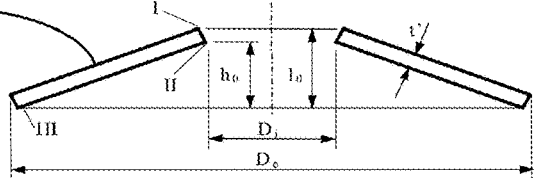

characteristic of spring

| dimensions | | | |
|---|---|---|---|
| outer diam.: | $D_e =$ | 8.000 | mm |
| inner diam.: | $D_i =$ | 3.200 | mm |
| thickness: | $t =$ | 0.350 | mm |
| red. thickness: | $t' =$ | 0.350 | mm |
| spring height: | $l_0 =$ | 0.700 | mm |
| data | $h_0 =$ | 0.350 | mm |
| $h_0/t =$ 1.000 | $h_0' =$ | 0.350 | mm |
| $h_0'/t =$ 1.000 | $D_e/D_i =$ | 2.500 | |

1 spring    1

| | load points of one spring | | | calculated stresses | | | | load points of one spring | | |
|---|---|---|---|---|---|---|---|---|---|---|
| load- point | height l mm | travel s mm | load F N | $\sigma_I$ | $\sigma_{II}$ | $\sigma_{III}$ | $\sigma_{OM}$ MPa | height l mm | travel s mm | load F N |
| 0 | 0.700 | | | | | | | 0.700 | | |
| 1 | 0.488 | 0.212 | 215 | -3434 | 880 | 1555 | -1318 | 0.488 | 0.212 | 215 |
| 2 | 0.363 | 0.337 | 274 | -4939 | 1919 | 2190 | -2095 | 0.363 | 0.337 | 274 |
| Flat | 0.350 | 0.350 | 279 | -5074 | 2049 | 2244 | -2175 | 0.350 | 0.350 | 279 |

| specification | | | |
|---|---|---|---|
| material: | 50 CrV 4 | Youngs-modulus: | 206000 MPa |
| surface finish: | shot peening | temperature: | 20 °C |
| corrosion prot.: | phosphated and oiled | | | fatigue life of springs
upper stress too high!                    S2 too high!
        travel:    0.13 mm    between l 1 :    0.49 mm    and l 2 :    0.36 mm remarks

Load tolerance:    +25 / -7,5% at 75% of h0 of one spring
tolerance inner diam.:    3.200    mm    to    3.320    mm
tolerance outer diam.:    7.850    mm    to    8.000    mm

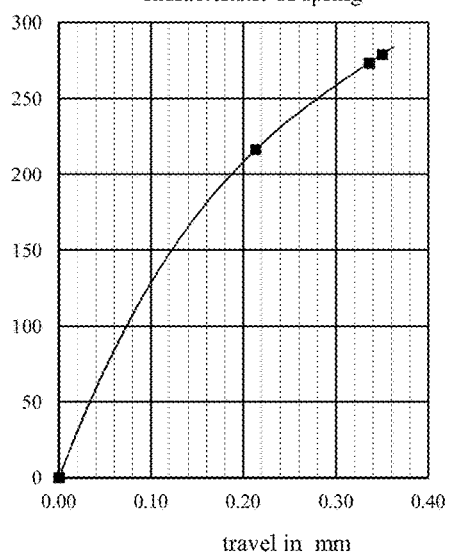

FIG. 6

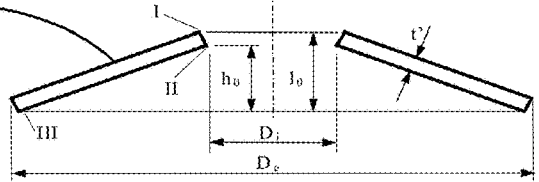

Disc Springs, Data Sheet
group 1 part./drawing no.:
project:

82 — dimensions
| | | | |
|---|---|---|---|
| outer diam.: | $D_e=$ | 8.000 | mm |
| inner diam.: | $D_i=$ | 3.400 | mm |
| thickness: | $t=$ | 1.100 | mm |
| red. thickness: | $t'=$ | 1.100 | mm |
| spring height: | $l_0=$ | 1.211 | mm |

| data | | $h_0=$ | 0.111 | mm |
|---|---|---|---|---|
| $h_0/t=$ | 0.101 | $h_0'=$ | 0.111 | mm |
| $h_0'/t'=$ | 0.101 | $D_e/D_i=$ | 2.353 | |

1 spring

| | load points of one spring | | | calculated stresses | | | | load points of one spring | | |
|---|---|---|---|---|---|---|---|---|---|---|
| load-point | height l mm | travel s mm | load F N | $\sigma_I$ | $\sigma_{II}$ | $\sigma_{III}$ | $\sigma_{OM}$ | height l mm | travel s mm | load F N |
| | | | | MPa | | | | | | |
| 0 | 1.211 | | | | | | | 1.211 | | |
| 1 | 0.488 | 0.723 | 20538 | -18296 | 27196 | 7155 | -14386 | 0.488 | 0.723 | 20538 |
| 2 | 0.363 | 0.848 | 25456 | -20157 | 33201 | 7658 | -16873 | 0.363 | 0.848 | 25456 |
| Flat | 1.100 | 0.111 | 2799 | -3644 | 3341 | 1570 | -2209 | 1.100 | 0.111 | 2799 | specification
| | | | |
|---|---|---|---|
| material: | 50 CrV 4 | Youngs-modulus: | 206000 MPa |
| surface finish: | shot peening | temperature: | 20 °C |
| corrosion prot.: | phosphated and oiled | | | fatigue life of springs
upper stress too high!  S2 too high!
travel: 0.13 mm   between l 1: 0.49 mm   and l 2: 0.36 mm remarks Load tolerance:   +25 / -7,5% at 75% of h0 of one spring
tolerance inner diam.:   3.400 mm   to   3.520 mm
tolerance outer diam.:   7.850 mm   to   8.000 mm

FIG. 19

Disc Springs, Data Sheet
group 1 part./drawing no.:

project:

dimensions

| | | | |
|---|---|---|---|
| outer diam.: | $D_e=$ | 8.000 | mm |
| inner diam.: | $D_i=$ | 3.400 | mm |
| thickness: | $t=$ | 1.100 | mm |
| red. thickness: | $t'=$ | 1.100 | mm |
| spring height: | $l_0=$ | 1.232 | mm | data

| | | | | |
|---|---|---|---|---|
| | | $h_0=$ | 0.132 | mm |
| $h_0/t=$ | 0.120 | $h_0'=$ | 0.132 | mm |
| $h_0'/t=$ | 0.120 | $D_e/D_i=$ | 2.353 | |

1 spring     1 characteristic of spring spring-load in N vs travel in mm

| | load points of one spring | | | calculated stresses | | | | load points of one spring | | |
|---|---|---|---|---|---|---|---|---|---|---|
| load-point | height l mm | travel s mm | load F N | $\sigma_I$ | $\sigma_{II}$ | $\sigma_{III}$ | $\sigma_{OM}$ MPa | height l mm | travel s mm | load F N |
| 0 | 1.232 | | | | | | | 1.232 | | |
| 1 | 0.488 | 0.744 | 21035 | -19020 | 27794 | 7472 | -14804 | 0.488 | 0.744 | 21035 |
| 2 | 0.363 | 0.869 | 25946 | -20881 | 33799 | 7974 | -17291 | 0.363 | 0.869 | 25946 |
| Flat | 1.100 | 0.132 | 3328 | -4367 | 3939 | 1886 | -2626 | 1.100 | 0.132 | 3328 | specification

| | | | |
|---|---|---|---|
| material: | 50 CrV 4 | Youngs-modulus: | 206000 MPa |
| surface finish: | shot peening | temperature: | 20 °C |
| corrosion prot.: | phosphated and oiled | | | fatigue life of springs
upper stress too high!                    S2 too high!
           travel:     0.13 mm     between l 1:     0.49 mm     and l 2:     0.36 mm remarks

Load tolerance:     +25 / -7,5% at 75% of h0 of one spring
tolerance inner diam.:     3.400     mm     to     3.520     mm
tolerance outer diam.:     7.850     mm     to     8.000     mm

FIG. 20

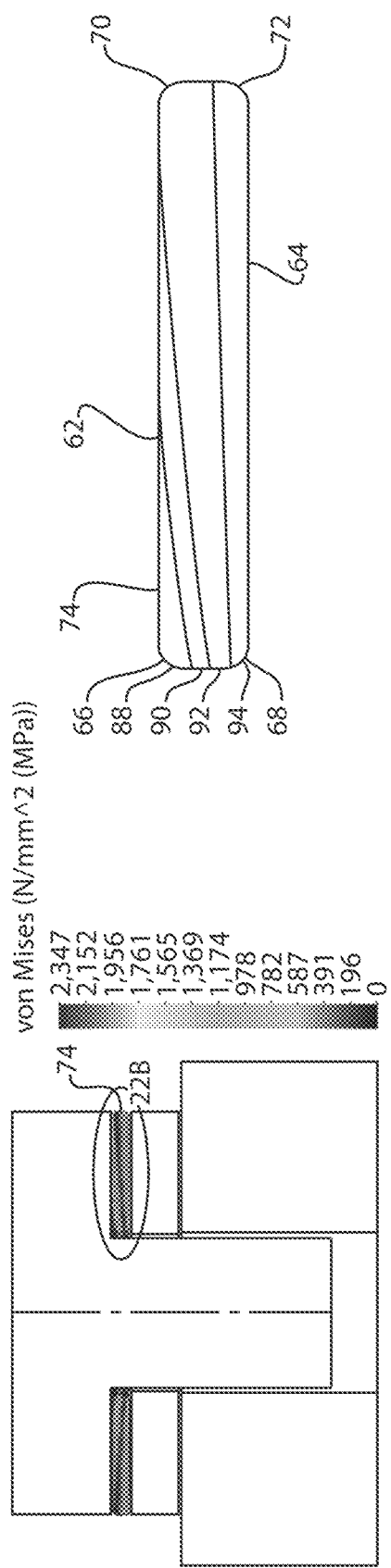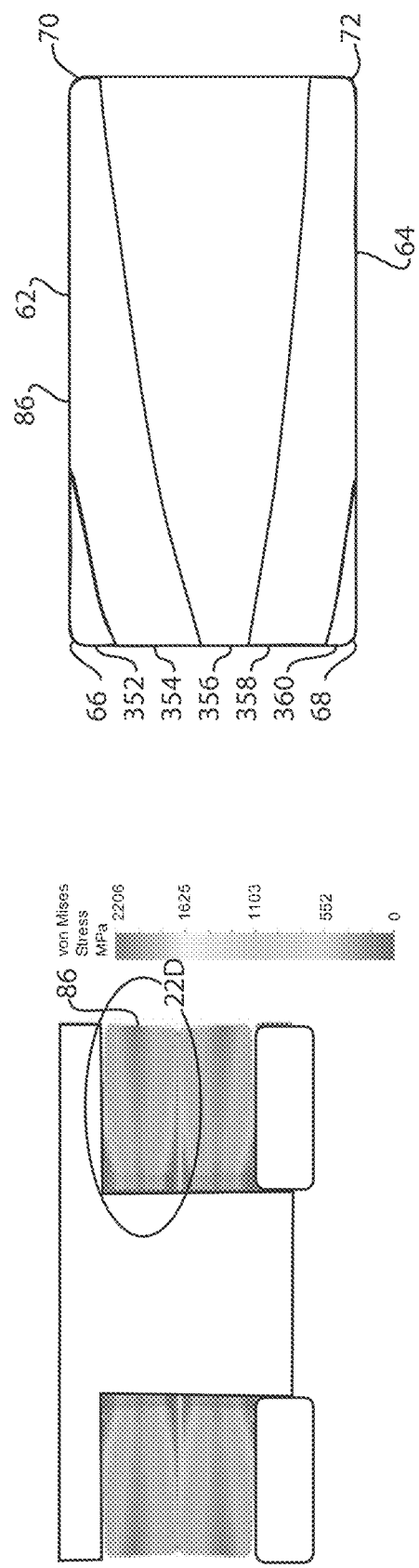
FIG. 22A
FIG. 22B
FIG. 22C
FIG. 22D

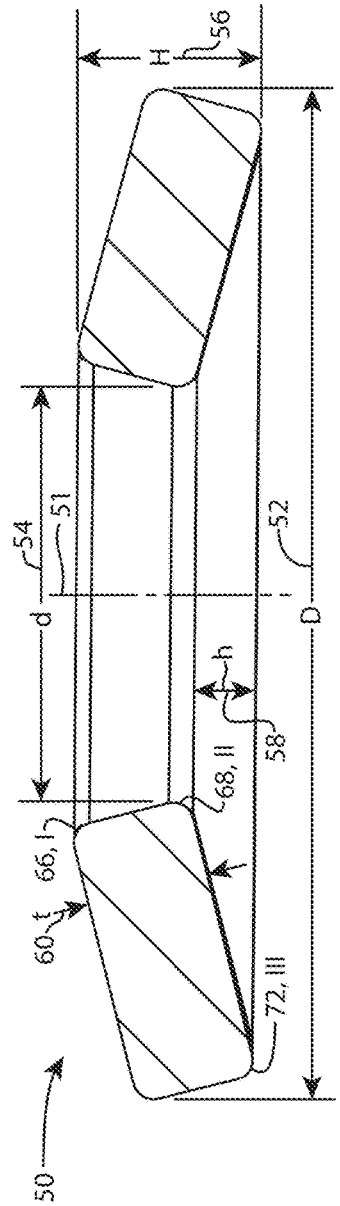

FIG. 25A

| Name | Intended Configuration | Outer Diameter, mm D | Inner Diameter, mm d | Thickness, mm t | Overall Height, mm H | Inner Height, mm h | Ratio of Inner Height to Thickness h/t | Spring Travel per Washer, mm s | Force per Washer, N F | $\sigma_I$ MPa | $\sigma_{II}$ MPa | $\sigma_{III}$ MPa |
|---|---|---|---|---|---|---|---|---|---|---|---|---|
| Mubea Standard Offering | | | | | | | | | | Stress from Mubea Design Program (UTS = 2206 MPa, YS = 1862 MPa) | | |
| | | 8.0 | 3.2 | 0.30 | 0.55 | 0.25 | 0.83 | 0.25 | 126 | -2952 | 1409 | 1290 |
| | | 8.0 | 3.2 | 0.40 | 0.60 | 0.20 | 0.50 | 0.20 | 238 | -2820 | 1832 | 1198 |
| | | 8.0 | 3.2 | 0.50 | 0.70 | 0.20 | 0.40 | 0.20 | 465 | -3401 | 2413 | 1430 |
| | | 8.0 | 4.2 | 0.20 | 0.45 | 0.25 | 1.25 | 0.25 | 42 | -2195 | 622 | 1251 |
| | | 8.0 | 4.2 | 0.30 | 0.55 | 0.25 | 0.83 | 0.25 | 142 | -2900 | 1326 | 1620 |
| | | 8.0 | 4.2 | 0.40 | 0.60 | 0.20 | 0.50 | 0.20 | 269 | -2757 | 1750 | 1511 |
| BMG Design Examples | | | | | | | | | | | | |
| 8 x 3.2 x 0.35 | Parallel 7 | 8.0 | 3.2 | 0.35 | 0.70 | 0.35 | 1.00 | 0.294 | 256 | -4465 | 1518 | 1995 |
| | Parallel 7 | | | | | | | 0.297 | 286 | | | |
| 8 x 3.4 x 1.1 | Single | 8.0 | 3.4 | 1.10 | 1.30 | 0.20 | 0.18 | 0.160 | 4050 | -5506 | 4562 | 2406 |
| | Single | | | | | | | 0.160 | 2600 | | | |
| | Series 2 | | | | | | | 0.112 | 2853 | -3920 | 3127 | 1721 |
| | Series 2 | | | | | | | 0.110 | 2500 | | | |
| 8 x 3.4 x 0.82 | Single | 8.0 | 3.4 | 0.82 | 1.02 | 0.20 | 0.24 | 0.152 | 1602 | -4028 | 3102 | 1776 |
| | Single | | | | | | | 0.155 | 1500 | | | |
| | Series 4 | | | | | | | 0.112 | 1192 | -3023 | 2230 | 1340 |
| | Series 4 | | | | | | | 0.111 | 1500 | | | |

FIG. 25B

| Configuration | 8 x 3.2 x 0.35 | | 8 x 3.2 x 0.82 | | | 8 x 3.2 x 1.1 | | 8 x 3.4 x 1.1 | | |
|---|---|---|---|---|---|---|---|---|---|---|
| | Single | Parallel | Single | Series 4 | Series 4 | Single | Series 4 | Series 2 | Series 2 | Series 2 |
| Figure No. | 7 | 9 | 11 | 12A | 12B | 15 | | 17 | 18A | 18B |
| Effective Installation Load, N | 286 | 2000 | 1500 | 2000 | 2000 | 2500 | 2800[A] | 2500 | 2500 | 2500 |
| Load After 0.75 mm Diminution from Installed Load, N | 143 | 1000 | 560 | 1300 | 1250 | 1170 | 2000[A] | 1500 | 1450 | 1420 |
| Diminution at 1500 N, mm | 0.04 | 0.04 | 0 | 0.050 (0.056)[B] | 0.035 (0.041)[B] | 0.057 (0.071)[B] | 0.140[A] | 0.075 (0.088)[B] | 0.071 (0.083)[B] | 0.069 (0.088)[B] |
| Diminution at 1000 N, mm | 0.088 | 0.088 | 0.032 | 0.160 (0.173)[B] | 0.140 (0.153)[B] | 0.089 (0.110)[B] | 0.200[A] | 0.125 (0.145)[B] | 0.112 (0.132)[B] | 0.114 (0.124)[B] |
| % Difference in 1000 N Diminution versus 8 x 3.2 x 0.35 | — | 0% | — | 82% | 59% | 1% | 127% | 42% | 27% | 30% |

[A] Estimates
[B] Values in parentheses include deflection of a 3.2 mm diameter x 21 mm long screw

FIG. 26

Compression Force after Diminution

| Total Diminution $\delta_D$ | Compression Loss $\Delta C_{BW}$ | Final Compression $C_{BW}$ | Bone Stress After Diminution | Spring Extension $\delta_W$ | Bone Extension $\delta_B$ | Screw Contraction $\delta_S$ |
|---|---|---|---|---|---|---|
| | $\Delta C_{BW} = \delta_D K_{SBW}$ | $C_{BW} = 3000\,N - \Delta C_{BW}$ | | $\delta_W = \Delta C_{BW}/K_W$ | $\delta_B = \Delta C_{BW}/K_B$ | $\delta_S = \Delta C_{BW}/K_S$ |
| mm | N | N | Mpa | mm | mm | mm |
| 0.114 | 1163 | 1837 | 18.2 | 0.081 | 0.019 | 0.014 |
| 0.15 | 1531 | 1469 | 14.5 | 0.107 | 0.024 | 0.018 |
| 0.25 | 2551 | 449 | 4.4 | 0.179 | 0.041 | 0.031 |

Screw Spring Constant: $K_S = (0.000012\,mm/N)^{-1}$ Per Screw-in-Bone FEA
Bone Spring Constant: $K_B = (0.000015\,mm/N)^{-1}$ Per Screw-in-Bone FEA
Washer Spring Constant: $K_W = (0.000070\,mm/N)^{-1}$ Per BMG Prototype 3 Dual Washer Stack test, Fig. 7
Series (Screw + Bone + Washer) Spring Constant: $1/K_{SBW} = 1/K_S + 1/K_B + 1/K_W = (0.000098\,mm/N)$

FIG. 27B

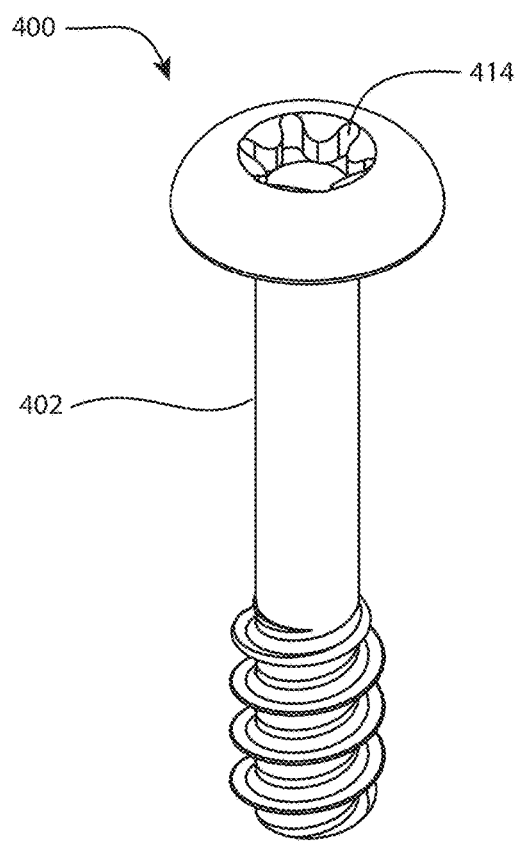
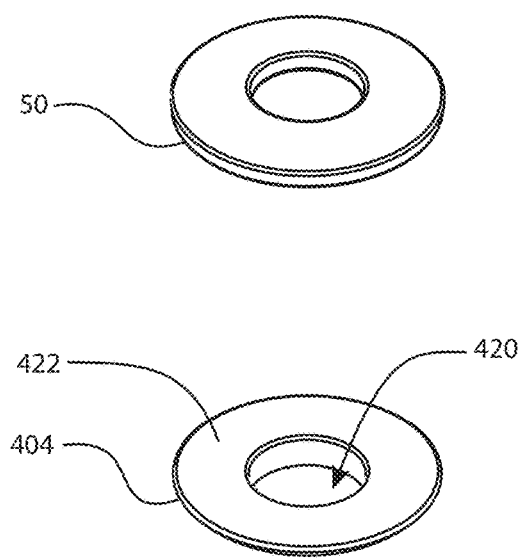
FIG. 29C
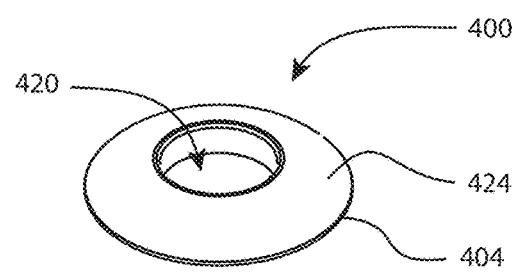
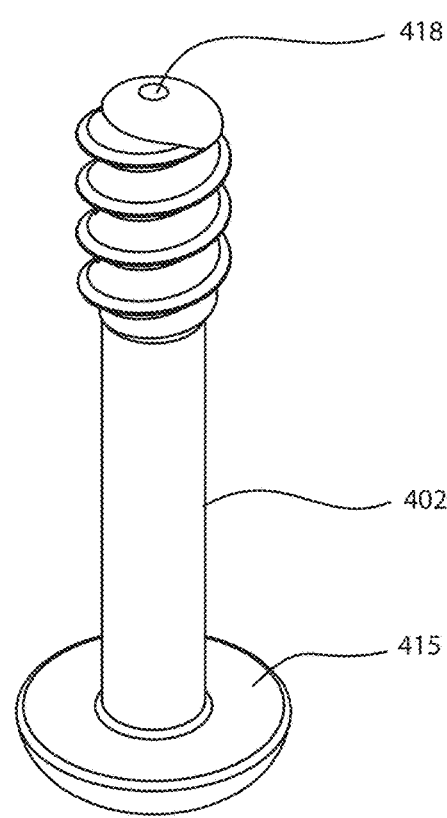
FIG. 29D

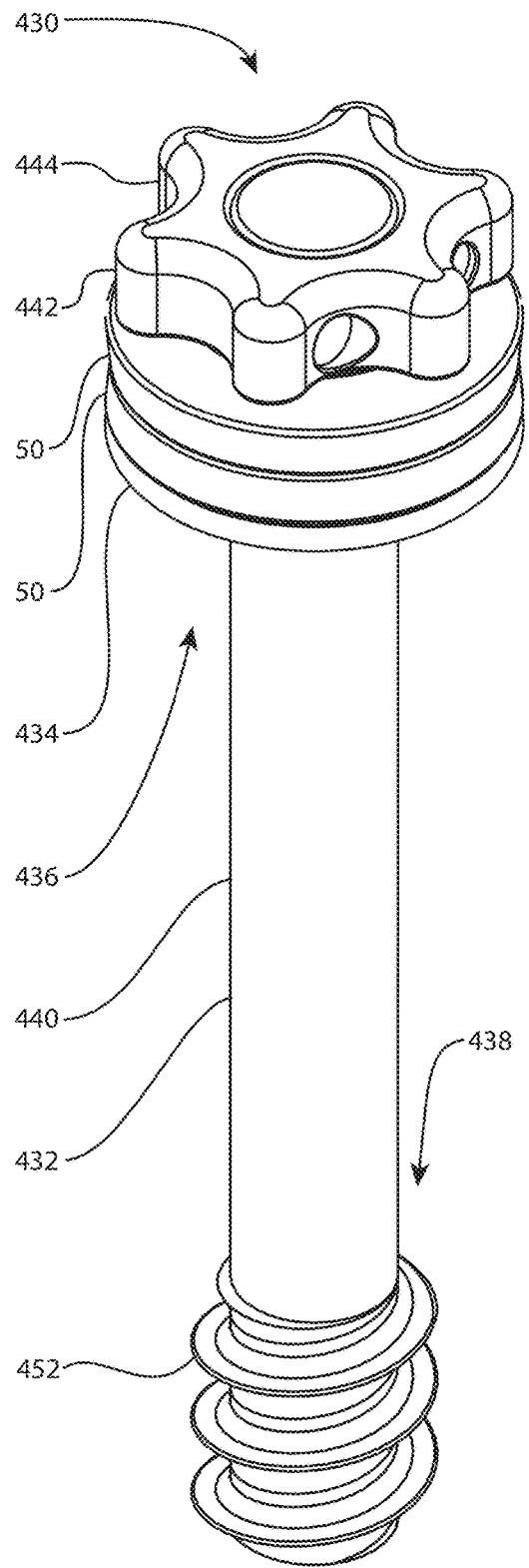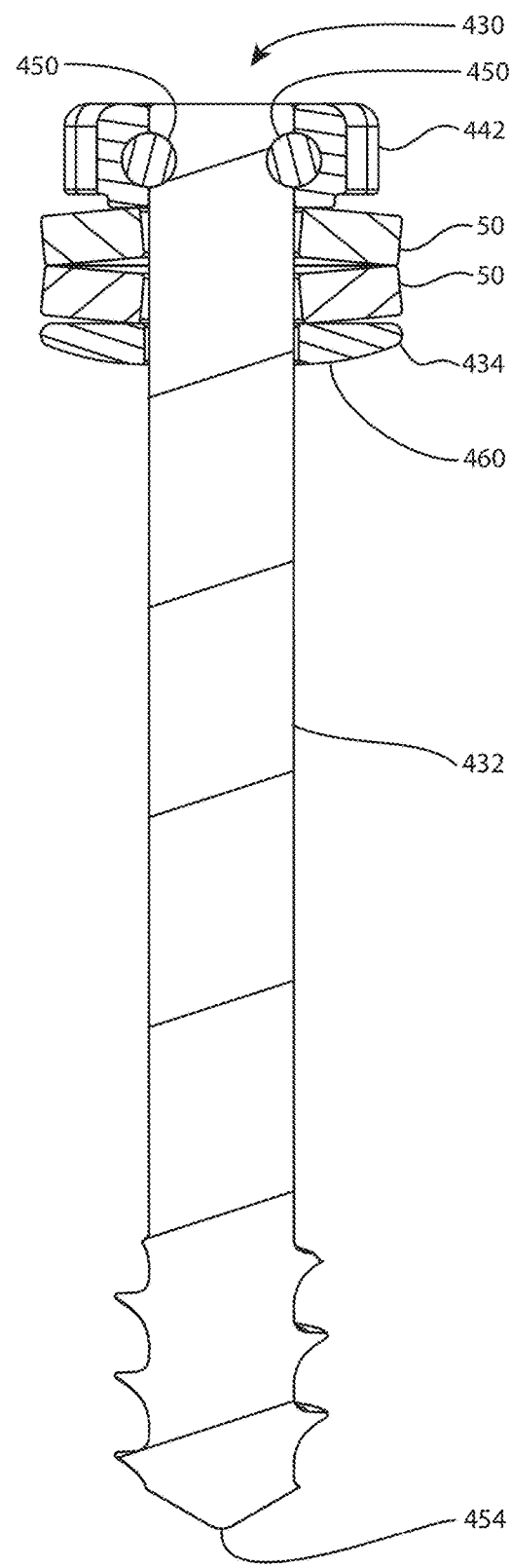
FIG. 30A
FIG. 30B

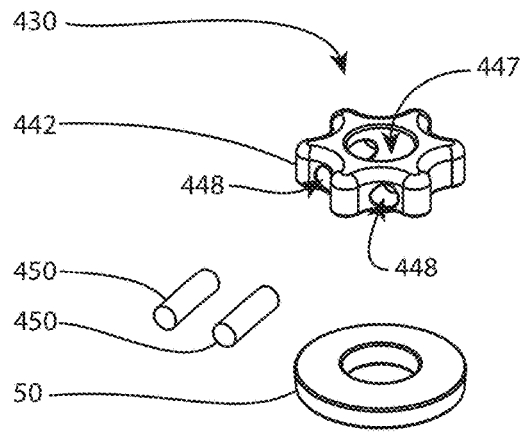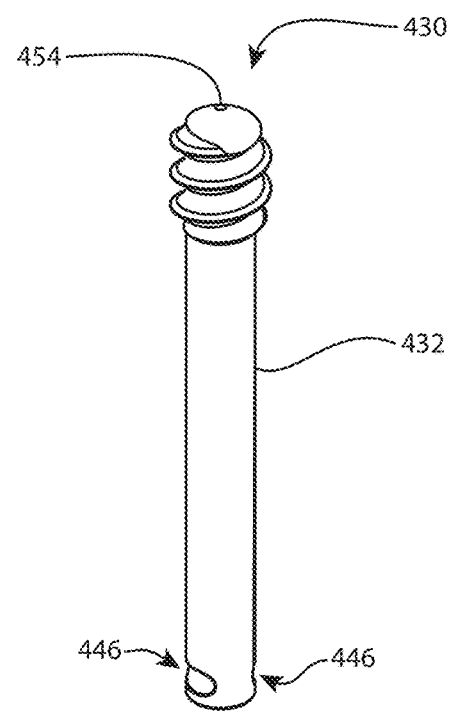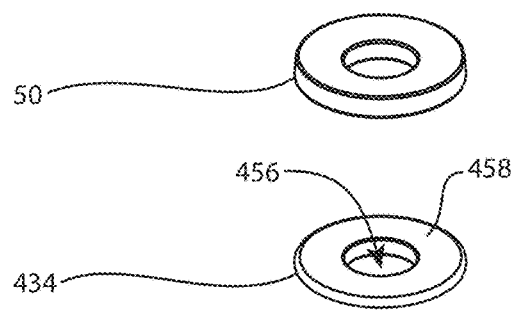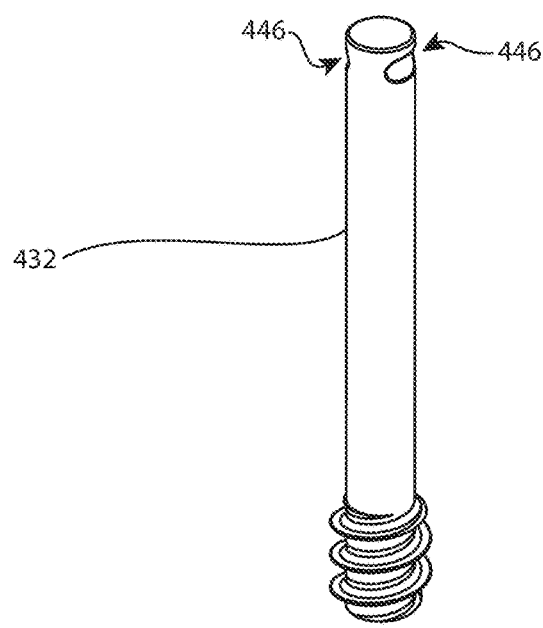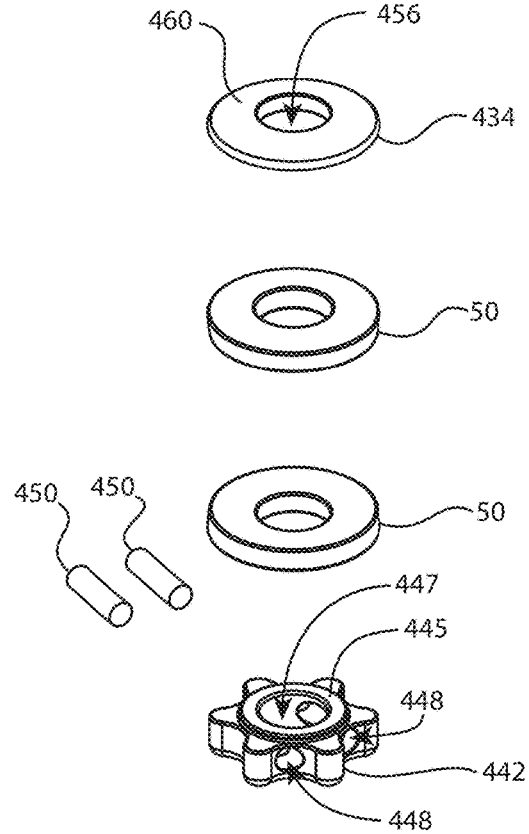
FIG. 30C  FIG. 30D

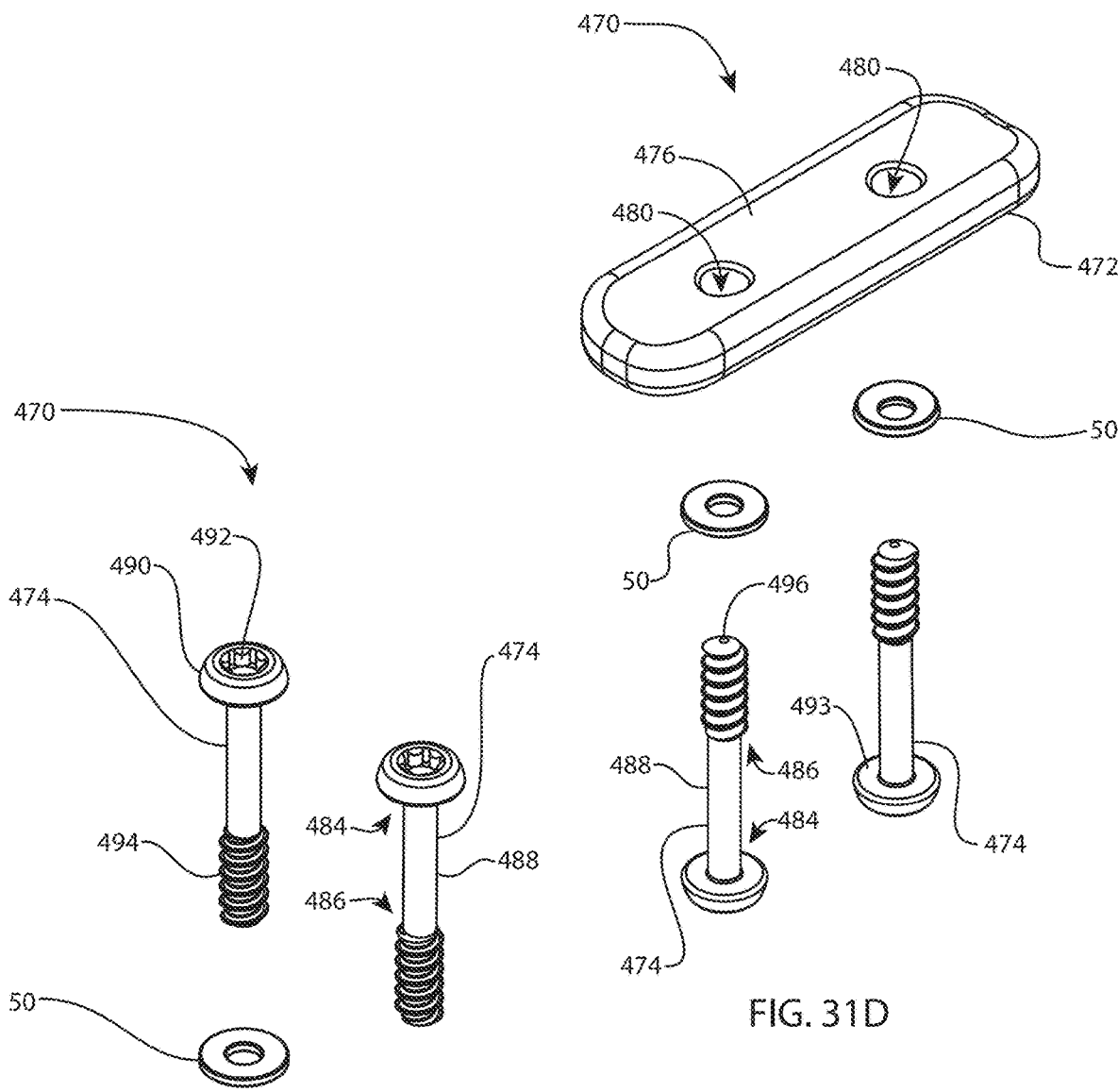
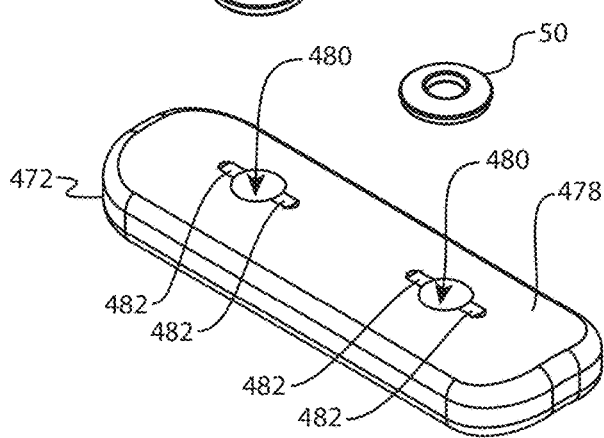
FIG. 31C

BONE COMPRESSION SYSTEMS

CROSS-REFERENCE TO RELATED APPLICATIONS

The present application is a continuation of:

U.S. patent application Ser. No. 14/944,197, entitled BONE COMPRESSION SYSTEMS, which was filed on Nov. 17, 2015;

U.S. patent application Ser. No. 14/944,197 claims the benefit of:

U.S. Provisional Patent Application Ser. No. 62/080,893, entitled BONE COMPRESSION SYSTEMS, which was filed on Nov. 17, 2014; and U.S. Provisional Patent Application Ser. No. 62/080,954, entitled BONE COMPRESSION SYSTEMS, which was filed on Nov. 17, 2014.

The foregoing are incorporated by reference as though set forth herein in their entirety.

TECHNICAL FIELD

The present disclosure relates to apparatus, systems, and methods for compressing bone portions together with a dynamic load that stimulates the bone portions to fuse. More specifically, the present disclosure relates to a spring washer with specific load versus deflection characteristics achieved by specific design, material, and fabrication; medical devices which include one or more of the spring washers, including bone screws, and bone plate and screw systems; methods of designing and fabricating the spring washer and medical devices; and methods of using the spring washer and medical devices.

BACKGROUND

There are many situations in which bones, bone portions, or bone fragments are to be fused together during the healing process. The fragments of a broken bone are fused together to heal a fracture. The bone portions involved in a corrective osteotomy or resection are fused together during healing so that the healed bone(s) provide more normal anatomy, biomechanics, and/or cosmesis. The bones involved in a joint fusion, also known as an arthrodesis or an artificial ankylosis, are fused together to eliminate a joint that has become painful or degenerate. These are a few examples of situations in which bones, bone portions, or bone fragments become fused together during the healing process. For brevity, the remainder of this specification will use the term "bone fragment" as a generic term for an actual fragment of a broken bone, a bone portion of an osteotomy, or a bone of a joint fusion. The term "discontinuity" will be used as a generic term for a fracture, an osteotomy or resection, or a joint for fusion.

Successful fusion, also known as union, depends on the formation of new bone tissue that bridges from one bone portion to another across a bony discontinuity. The formation of new bone is sensitive to the local stress field and local micromotion between bone portions. When stress falls below 1 MPa-4 MPa, bone atrophies. There is no impact to bone strengthening when stress is between 1 MPa-4 MPa and 20 MPa. The threshold for bone strengthening is genetically determined and occurs at 20 to 30 MPa. The operational threshold for bone occurs at about 60 MPa. When stress is sustained above this threshold, bone experiences osteoclastic resorption. The operational threshold may be referred to as the live stress yield point. The ultimate strength of normal bone in healthy young adult mammals is 120 MPa for short duration stress.

Doctor assisted healing of a bone fracture consists of reduction (pushing bones back into place), stabilizing the bone fragments, eliminating any conditions incompatible with healing, and then waiting for natural physiological processes to occur. Under typical conditions, and the current standard of care, available hardware screws and other internal fixation hardware loosen by a process described below. When conventional internal fixation hardware loosens, remaining force and contribution to stability and bone growth become uncertain. Some screws loosen completely and may twist out if not locked into a plate. Consequently, physicians typically prescribe protection (casting) and non-weight bearing of the discontinuity. Despite well-established healing benefits, these measures and the unreliable stability warranting them, also result in bone and muscle atrophy and increased risk of complications from premature weight bearing. Such complications may result in revisional surgery which prolongs potential complications from non-weight bearing, increasing risk that complications will become chronic morbidities. Hardware loosening is due to bone gaps created by osteoclastic resorption. The bone dies about 15 microns deep on each side of an osteotomy, largely due to lack of blood. Further, at the micro scale, contact surfaces (bone-to-bone fracture surfaces, screw landing-to-bone and bone-to-top-of-threads) do not meet uniformly but initially at limited contact points. These initial bone contact points are highly stressed (i.e., >60 N/mm2 (MPa)) by the installed tension in the screw and/or bone-plates. Once reduced and fixated, osteoclasts carve out the dead bone (resulting in fracture zone gaps) and resorption removes highly stressed initial bone-to-bone and bone-to-screw contact points (a process we call hardware settling-in).

Under typical conditions, if bone fragments are held in close proximity and stable by something other than loose hardware (for example casting and non-load bearing), bones heal by forming a callus at the discontinuity. The traditional healing process involves the formation of a temporary, weak cartilaginous material bridging the discontinuity, followed by formation of a mechanically weak woven bone callus with haphazardly organized collagen fibers. The callus is later replaced by highly organized lamellar bone, the normal type of adult mammalian bone. However, when bone portions remain stable and under optimal compression, for example, by the use of external fixation and frequent retightening, the callus reaction is largely skipped in favor of direct lamellar bone growth across the discontinuity. When direct lamellar bone growth occurs, healing time may be reduced by up to 50% compared to the typical progression of healing. The present technology is internal fixation to stabilize the bone portions with optimal compression to skip the callus reaction, enable direct lamellar bone growth across the discontinuity and reduce healing time by 50%.

As mentioned above, when a bony discontinuity is reduced for fixation, at the micro scale, the bone portions initially touch at only a few small contact points on their interface surfaces. Bone screw threads, shoulders, heads, plates, and the like also initially bear on the bone at only a few small contact points. These small initial contact points in the interface are locally highly stressed by bone-on-bone contact and/or by hardware that is initially producing compression in the bony discontinuity. The interface may also be referred to as the discontinuity zone or fracture zone.

Under sufficient installed compression, the few small contact points fissure and are soon resorbed by the body as a result of natural healing processes. Only so long as compression is sustained, this resorption results in progressive diminution of the interface gap, or fracture gap. Diminution is the gradual reduction in the physical dimension or gap between adjacent surfaces of bone portions across a discontinuity during the natural healing process. Diminution may occur as osteoclasts resorb necrotic bone on the contacting surfaces of the discontinuity. Diminution takes place over 2 to 24 hours after the bony discontinuity is stabilized and compressed together. Again, if compression is sustained, diminution may continue to take place over a few days. It is desirable for diminution to continue until hardware has settled in and all gaps from osteoclastic resorption of necrotic bone surfaces have been closed. As soon as traditional hardware loosens, diminution ceases and the discontinuity becomes unstable. Hardware of the present embodiment is to sustain load to continue diminution for full gap closure, hardware setting in and still have sufficient compression to stabilize the discontinuity so that intermittent load bearing is recommended.

The inventors have found that diminution has been insufficiently quantified. Electron microscopy has been ineffective in measuring diminution, at least because of the limited field of view. Magnetic resonance imaging (MRI), X-rays, ultrasonics, and combinations have also been ineffective at measuring micron movement from diminution over the size of typical fracture zones. Diminution is not equal to measurable displacement between external fixator pins or wires; the external fixator apparatus introduces significant dimensional artifact.

AO Synthes in CH669898 (Apr. 28, 1989) presumed that diminution would be in the range of 1 mm to 4 mm and installed loads would be approximately 2025 N; for a 3 mm shank diameter screw, the disclosed devices included spring stacks totaling 12 mm to 18 mm in height to accommodate the deflection and load—a medically unacceptable size, considering that cortical bone thickness is only about 8 mm in areas where a 3 mm shank diameter screw would be used.

Olerud et al. (*Journal of Bone and Joint Surgery* 1968, V50B, p. 844) reported a gap of at least 0.030 mm in a canine model using fluorescence and angiography. The inventors found this reference to be among the best available research on fracture gaps.

Through analysis of available research (Olerud), engineering calculations of diminution closure induced by longitudinal relaxation of the hardware (screws) and bone, and finite element analysis, the inventors have concluded that total diminution in a 30° osteotomy in an 18.2 mm diameter long bone fixed with three screws having 3 mm shank diameters may be in the range of 0 mm to 0.500 mm, 0.002 mm to 0.300 mm, 0.030 mm to 0.250 mm, 0.060 mm to 0.250 mm, 0.030 mm to 0.160 mm, 0.060 mm to 0.160 mm, 0.030 mm to 0.150 mm, 0.060 mm to 0.150 mm, 0.030 mm to 0.114 mm, 0.060 mm to 0.114 mm, 0.030 mm to 0.100 mm, 0.060 mm to 0.100 mm, 0.030 mm to 0.087 mm, 0.060 mm to 0.087 mm, 0.078 mm to 0.087 mm, 0.030 mm to 0.078 mm, 0.060 mm to 0.078 mm, 0.030 mm to 0.075 mm, or 0.060 mm to 0.075 mm. The conclusion is breakthrough enabling: it means that spring stack heights of 1 mm to 3 mm become feasible due to the low displacement requirement, and thus fit better into the overall height of 3 mm to 5 mm for a traditional screw with 3 mm shank diameter and 8 mm head diameter.

Additional information about diminution is disclosed in U.S. Provisional Application Ser. No. 62/080,893, at least in pages 37, 39-41, 43-45, 67, and 68 of 94; and in U.S. Provisional Application Ser. No. 62/080,954, at least in FIGS. 4-13 and pages 16, 17, and 21-33 of 67.

Total diminution is relative to the specific osteotomy or other discontinuity and the specific bone involved. These factors dictate at least the screw length and the area of bone involved around the screw, both of which contribute to total diminution. Having set forth the derivation of total diminution for the preceding conditions, one of skill in the art may readily derive total diminution for other discontinuities and/or other bones.

Tension, in the rigid hardware typically used to create compression across a bony discontinuity, is reduced by diminution of the interface gap, or fracture gap and by hardware settling in. An orthopedic screw, installed across an interface gap of a discontinuity, stretches a few microns when the screw is tightened enough to compress the bone portions together. When diminution occurs in the interface gap, the stretched screw relaxes and loses tension. The screw may relax further as a result of continued fissuring and resorption of small contact points between bone portions, under hardware, and around hardware threads bearing on bone. So long as the screw sustains sufficient compression in the bone, the result may be progressive diminution of the interface gap. Diminution may continue until net bone stress levels on bearing points decline to 60 MPa (8.7 ksi) or less. With conventional hardware, tension in the screw drops quickly as diminution occurs, because the screws are stiff. In other words, the screw loosens.

Even loose internal fixation hardware may suffice to hold bone portions together as long as the discontinuity is protected from load bearing for several weeks, such as by casting the affected body part. However, casting, bracing, crutches, non-weight-bearing, and other means of protecting a healing discontinuity have their drawbacks, many of which are secondary to low bone stress in the vicinity of the discontinuity and an extended period of disuse of the affected body part. Ideally, the internal fixation hardware should stabilize the bone portions and compress the bone portions together so that normal activities can be resumed as early as possible.

There is evidence of long felt need for sustained optimal compression of bone portions across a discontinuity with internal fixation devices, such as screws, plates, and cables. Many orthopedic spring screw designs have been published since 1944 without arriving at the particular solutions disclosed herein. The published designs tend to treat the spring washer as being interchangeable with other types of springs, such as coil springs or wave springs, that are incapable of sustaining the loads and elongations contemplated herein (when limited to a medically serviceable size). Furthermore, the published designs tend to treat the design of the spring washer in a superficial "black box" manner.

The goals of the present technology include:
Sustain compression of bone portions across the discontinuity during diminution and healing.
Close diminution gaps which open during the natural healing process.
Sustain reduction of bone portions across the discontinuity.
Resist relative movement of bone portions through sustained compression causing stabilizing friction between the bone portions at the discontinuity.
Enable early weight bearing so that post-operative non-weight-bearing period is significantly shortened or eliminated.
Resist loads associated with early protected weight bearing and exercise, preferably early unprotected weight bearing, and more preferably, intermittent overloads up to the ultimate strength of the bone. Return to optimal compression after overload events. Maintain reduction.

Optimize healing through sustained compression causing average bone stresses preferably between 18 MPa and 30 MPa, resulting in direct lamellar bone formation and little or no callus formation for up to a 50% reduction in healing time.

Facilitate bone bridging across the discontinuity.

Reduce callus reaction.

Reduce healing time substantially by sustained, optimal compression and by accommodating diminution and early healing stage exercise and/or activities, while providing full strength during intermittent overloads and returning to optimal compression once overload subsides.

Improve fusion rates, decrease rates of delayed union, malunion, non-union, and/or pseudarthrosis.

Reduce periosteal, intracortical, and/or endosteal porosity in the vicinity of the discontinuity through sustained compression while simultaneously avoiding stress shielding of the bone.

Reduce device size to be suitable for very small bones, i.e., hand and foot bones.

Spring washer sub-assembly height substantially equivalent to traditional rigid constructs to enable direct cortical load bearing and to avoid excess device protrusion into surrounding soft tissues. Spring washer sub-assembly includes spring washer or spring washer stack plus containment structure such as screw head, base, plate, etc. Spring washer sub-assembly heights are contemplated to be 3 mm to 5 mm for a screw with a 3 mm shank diameter and an 8 mm head diameter.

Provide constructs specific to longstanding problematic bony discontinuities such as calcaneus bone fractures, wherein the constructs are far less intrusive than, for example, lateral extensile plates.

Provide devices that make many existing rigid bone plates unnecessary. Devices may include screws and/or cables.

Reduce total cost to heal a discontinuity, including reducing risks and morbidities mentioned in this list, increasing patient function, and an earlier return to activities/work.

Low device cost comparable to traditional rigid constructs. In particular, low assembly cost for close-fitting spring washer on screw shank.

Reduce hardware failure, i.e., screw and/or wire fatigue and/or failure, causing loss of reduction.

Reduce plate failure, such as conventional plates and/or locking screw plates.

Eliminate bone comminution seen with traditional locking screw plates.

Decrease or avoid the risks associated with prolonged non-weight-bearing, such as blood clots, deep vein thrombosis (DVT) and associated risk of pulmonary embolism or stroke, osteopenia, muscular atrophy, joint ankylosis, soft tissue contractures, etc.

Reduce infection, especially pin-tract infection associated with external fixation devices.

Reduce pain, at least by accelerating healing, thereby decreasing duration and consumption of pain medications and concomitant risk of abuse and/or addiction.

Reduce post-traumatic arthritis.

By integrating a spring washer into medical devices such as screws and cables, the devices will accommodate diminution while continuing to hold the bone portions together under compression. Using such spring loaded hardware, internal fixation is secured against movement caused by internal and external forces, and can be optimized to sustain compression specific to promoting bone growth, preferably in the range of 4 MPa to 60 MPa, and more preferably in the range of 18 to 30 MPa. Early protected weight bearing may be tolerated in this scenario, resulting in a quicker return to activity and reduced morbidities.

SUMMARY

The various systems and methods of the present technology have been developed in response to the present state of the art, and in particular, in response to the problems and needs in the art that have not yet been fully solved by currently available medical devices with spring washers. There is no screw device currently available for surgeons, or any available patent art, which also sustains optimal bone compression following fixation. The systems and methods of the present technology may provide minimally invasive and more effective fixation than presently available to surgeons or in the patent art.

To achieve the foregoing, and in accordance with the technology as embodied and broadly described herein, the inventors have challenged long standing assumptions regarding the amount of diminution to achieve closure of a fracture gap or discontinuity gap. This disclosure sets forth numerical analysis and engineering well beyond generally accepted parameters, with validation by mechanical testing.

In an aspect of the technology, a system includes: a base including a bone-facing surface, a top surface opposite the bone-facing surface, and a through hole; a screw including a distal portion with bone-engaging external threads, a proximal portion opposite the distal portion, and a shank portion between the distal portion and the proximal portion, wherein a major diameter of the external threads is larger than the through hole of the base, wherein the shank portion fits through the through hole of the base; a screw head coupled to the proximal portion of the screw, wherein the screw head includes an outer diameter and an overall height, wherein the outer diameter of the screw head is larger than the through hole of the base; and a spring washer including a frustoconical ring having an outer diameter D, an inner diameter d, an overall height H, an inner height h, and a thickness t, wherein $t/D$ is between 0.04375 and 0.150, wherein D is larger than the through hole of the base; wherein when the system is operatively assembled, the shank portion extends through the inner diameter of the spring washer and the through hole of the base so that the spring washer sits on the top surface of the base, the spring washer is between the base and the screw head, and the distal portion of the screw protrudes past the bone-facing surface of the base.

Embodiments of this aspect of the technology may include any of the following characteristics. The base includes an annular disk. The bone-facing surface of the base is a convex spherical surface. The top surface of the base is a flat surface. The shank portion has a diameter of 3 mm, wherein the operatively assembled system delivers a first load between 2000 N and 4000 N at a first displacement and a second load between 1000 N and 3000 N at a second displacement, wherein the difference between the first displacement and the second displacement is less than 0.15 mm.

In another aspect of the technology, a system includes: a bone plate including a bone-facing surface, a top surface opposite the bone-facing surface, and a through hole; a screw including a distal portion with external bone-engaging threads, a proximal portion opposite the distal portion, and a smooth shank portion between the distal portion and the proximal portion, wherein the distal portion and the shank portion fit through the through hole of the bone plate; a screw head coupled to the proximal portion of the screw, wherein the screw head includes an outer diameter and an overall height, wherein the outer diameter of the screw head is larger than the through hole of the bone plate; and a spring washer coupled to the screw between the distal portion and the screw head, wherein the spring washer includes a frustoconical ring having an outer diameter D, an inner diameter d, an overall height H, an inner height h, and a thickness t, wherein t/D is between 0.04375 and 0.150, wherein D is larger than the through hole of the bone plate; wherein when the system is operatively assembled, the screw extends through the inner diameter of the spring washer and the through hole of the bone plate so that the distal portion of the screw protrudes past the bone-facing surface of the bone plate, and the spring washer and the screw head are outside of the through hole of the bone plate.

Embodiments of this aspect of the technology may include any of the following characteristics. The through hole of the bone plate has internal threads that are complementary to the external bone-engaging threads of the screw. The proximal portion of the screw includes a tapered shaft, wherein the tapered shaft shares a first outer diameter in common with the shank portion of the screw, wherein the tapered shaft has a second outer diameter adjacent to the screw head, wherein the second outer diameter is larger than the first outer diameter. The bone plate includes a recess in the top surface around the through hole. The recess of the bone plate has an inner diameter, wherein the inner diameter of the recess is larger than the outer diameter of the spring washer. When the system is operatively assembled, the spring washer sits in the recess of the bone plate. The recess of the bone plate has a depth from the top surface of the bone plate, wherein the depth of the recess is larger than the overall height of the spring washer. The depth of the recess of the bone plate is larger than the overall height of the spring washer plus the overall height of the screw head. When the system is operatively assembled, the spring washer is beneath the top surface of the bone plate. When the system is operatively assembled, the spring washer and the screw head are beneath the top surface of the bone plate. The system includes: a base including a flat first surface, a convex spherical second surface opposite the first surface, and a through hole; wherein the recess includes a concave spherical surface that is complementary to the convex spherical second surface of the base; wherein when the system is operatively assembled, the screw extends through the through hole of the base so that the spring washer sits on the flat first surface of the base, the spring washer is between the base and the screw head, the distal portion of the screw protrudes past the convex spherical second surface of the base, and the convex spherical second surface of the base sits in the recess of the bone plate.

In yet another aspect of the technology, a spring washer includes: a frustoconical ring having an outer diameter D, an inner diameter d, an overall height H, an inner height h, and a thickness t, wherein t/D is between 0.04375 and 0.1375.

Embodiments of this aspect of the technology may include any of the following characteristics. D is 8 mm±0.076 mm, d is 3.4 mm±0.076 mm, H is 1.295 mm±0.015 mm, h is 0.200 mm (reference), and t is 1.1 mm±0.015 mm. D is 8 mm±0.076 mm, d is 3.4 mm±0.076 mm, H is 1.017 mm±0.015 mm, h is 0.200 mm (reference), and t is 0.820 mm±0.015 mm. D is 8 mm±0.076 mm, d is 3.2 mm±0.076 mm, H is 0.700 mm±0.015 mm, h is 0.350 mm (reference), and t is 0.35 mm±0.015 mm. The spring washer is fabricated from a stainless steel with a tensile yield strength greater than 1276 MPa and an ultimate tensile strength greater than 1600 MPa. The spring washer is fabricated from an essentially nickel-free high-nitrogen austenitic stainless steel with a Young's modulus of 200 GPa, a tensile yield strength of 1862 MPa, and an ultimate tensile strength of 2206 MPa. D is less than 10 mm, wherein the spring washer delivers a first force of at least 1500 N at a deflection of less than 0.17 mm and a second force of 1000 N at a deflection of less than 0.125 mm. D is 8 mm±0.076 mm, wherein the spring washer delivers a first force of 2500 N at a deflection of 0.163 mm and a second force of 1000 N at a deflection of 0.117 mm. D is 8 mm±0.076 mm, wherein the spring washer delivers a first force of 1500 N at a deflection of 0.152 mm and a second force of 1000 N at a deflection of 0.082 mm.

In yet another aspect of the technology, a system includes: a base including a bone-facing surface, a top surface opposite the bone-facing surface, and a through hole; a screw including a distal portion with bone-engaging external threads, a proximal portion opposite the distal portion, and a shank portion between the distal portion and the proximal portion, wherein a major diameter of the external threads is larger than the through hole of the base, wherein the shank portion fits through the through hole of the base; a screw head coupled to the proximal portion of the screw, wherein the screw head includes an outer diameter and an overall height, wherein the outer diameter of the screw head is larger than the through hole of the base; and a spring washer including a frustoconical ring having an outer diameter D, an inner diameter d, an overall height H, an inner height h, and a thickness t, wherein the outer diameter of the spring washer is larger than the through hole of the base, wherein the shank portion fits through the inner diameter of the spring washer; wherein when the system is operatively assembled, the shank portion extends through the inner diameter of the spring washer and the through hole of the base so that the spring washer sits on the top surface of the base, the spring washer is between the base and the screw head, and the distal portion of the screw protrudes past the bone-facing surface of the base; wherein the operatively assembled system delivers a first load at a first displacement of the spring washer and a second load at a second displacement of the spring washer, wherein the first load is at least 1500 N, wherein the second load is at least 1000 N, wherein the second displacement is at most 0.5 mm less than the first displacement.

Embodiments of this aspect of the technology may include any of the following characteristics. An outer diameter of the shank portion is 3 mm, wherein the outer diameter of the screw head is 8 mm, wherein when the system is operatively assembled, an overall height of the base, the spring washer, and the head is no more than 5 mm. The first load is at least 2000 N. The first load is at least 2500 N. The second displacement is at most 0.250 mm less than the first displacement. The second displacement is at most 0.125 mm less than the first displacement. The second displacement is at most 0.075 mm less than the first displacement.

In yet another aspect of the technology, a method of internally fixing a discontinuity between first and second bone portions includes: providing an internal fixation device including: a base including a bone-facing surface, a top surface opposite the bone-facing surface, and a through hole; a screw including a distal portion with bone-engaging external threads, a proximal portion opposite the distal portion, and a shank portion between the distal portion and the proximal portion; a screw head coupled to the proximal portion of the screw, wherein the screw head includes an outer diameter and an overall height; and a spring washer including a frustoconical ring having an outer diameter D, an inner diameter d, an overall height H, an inner height h, and a thickness t; wherein when the system is operatively assembled, the shank portion extends through the inner diameter of the spring washer and the through hole of the base so that the spring washer sits on the top surface of the base, the spring washer is between the base and the screw head, and the distal portion of the screw protrudes past the bone-facing surface of the base; wherein the operatively assembled system delivers a first load at a first displacement of the spring washer and a second load at a second displacement of the spring washer, wherein the first load is at least 1500 N, wherein the second load is at least 1000 N, wherein the second displacement is at most 0.5 mm less than the first displacement; driving the operatively assembled system through the first and second bone portions so that the bone-facing surface of the base rests on the first bone portion, the screw extends across the discontinuity, and the bone-engaging external threads engage the second bone portion; and torqueing the operatively assembled system to compress the spring washer to the first displacement to deliver the first load.

Embodiments of this aspect of the technology may include any of the following characteristics. An outer diameter of the shank portion is 3 mm, wherein the outer diameter of the screw head is 8 mm, wherein when the system is operatively assembled, an overall height of the base, the spring washer, and the head is no more than 5 mm. The first load is at least 2000 N. The first load is at least 2500 N. The second displacement is at most 0.250 mm less than the first displacement. The second displacement is at most 0.125 mm less than the first displacement. The second displacement is at most 0.075 mm less than the first displacement.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 3 is a table listing physical characteristics of 316L stainless steel.

FIG. 4 is a table listing physical characteristics of titanium ASTM F136.

FIG. 5 is a table listing physical characteristics of stainless steel sold under the trademark BIODur 108™.

FIG. 6 is a data sheet for an 8×3.2×0.35 spring washer.

FIG. 19 is a data sheet for an 8×3.4×1.1 spring washer, with overall height H=1.211 mm and inner height h=0.111 mm.

FIG. 20 is a data sheet for another 8×3.4×1.1 spring washer, with overall height H=1.232 mm and inner height h=0.132 mm.

FIGS. 22A-22D are a comparison of the von Mises stress distributions in the spring washer of FIGS. 7A and 7B and the stack of spring washers of FIGS. 21A and 21B; FIG. 22A is the finite element analysis contour plot of FIG. 7A; FIG. 22B is the detail view of FIG. 7B; FIG. 22C is the finite element analysis contour plot of FIG. 21A; and FIG. 22D is the detail view of FIG. 21B.

FIG. 25A is another cross sectional view of the spring washer of FIG. 2A; and FIG. 25B is a table listing dimensions, travel, load, and stresses for various spring washers.

FIG. 26 is a table listing loads and diminutions for various spring washers.

FIG. 27B is a table of various diminution values.

FIG. 29C is an exploded view of the bone screw assembly of FIG. 29A; and FIG. 29D is another exploded view of the bone screw assembly of FIG. 29A from a different viewpoint.

FIG. 30A is an isometric view of another bone screw assembly; FIG. 30B is a cross sectional view of the bone screw assembly of FIG. 30A; FIG. 30C is an exploded view of the bone screw assembly of FIG. 30A; and FIG. 30D is another exploded view of the bone screw assembly of FIG. 30A from a different viewpoint.

FIG. 31C is an exploded view of the bone plate assembly of FIG. 31A; and FIG. 31D is another exploded view of the bone plate assembly of FIG. 31A from a different viewpoint.

FIG. 34C is an exploded view of the bone plate assembly of FIG. 34A.

DETAILED DESCRIPTION

Figure 1:
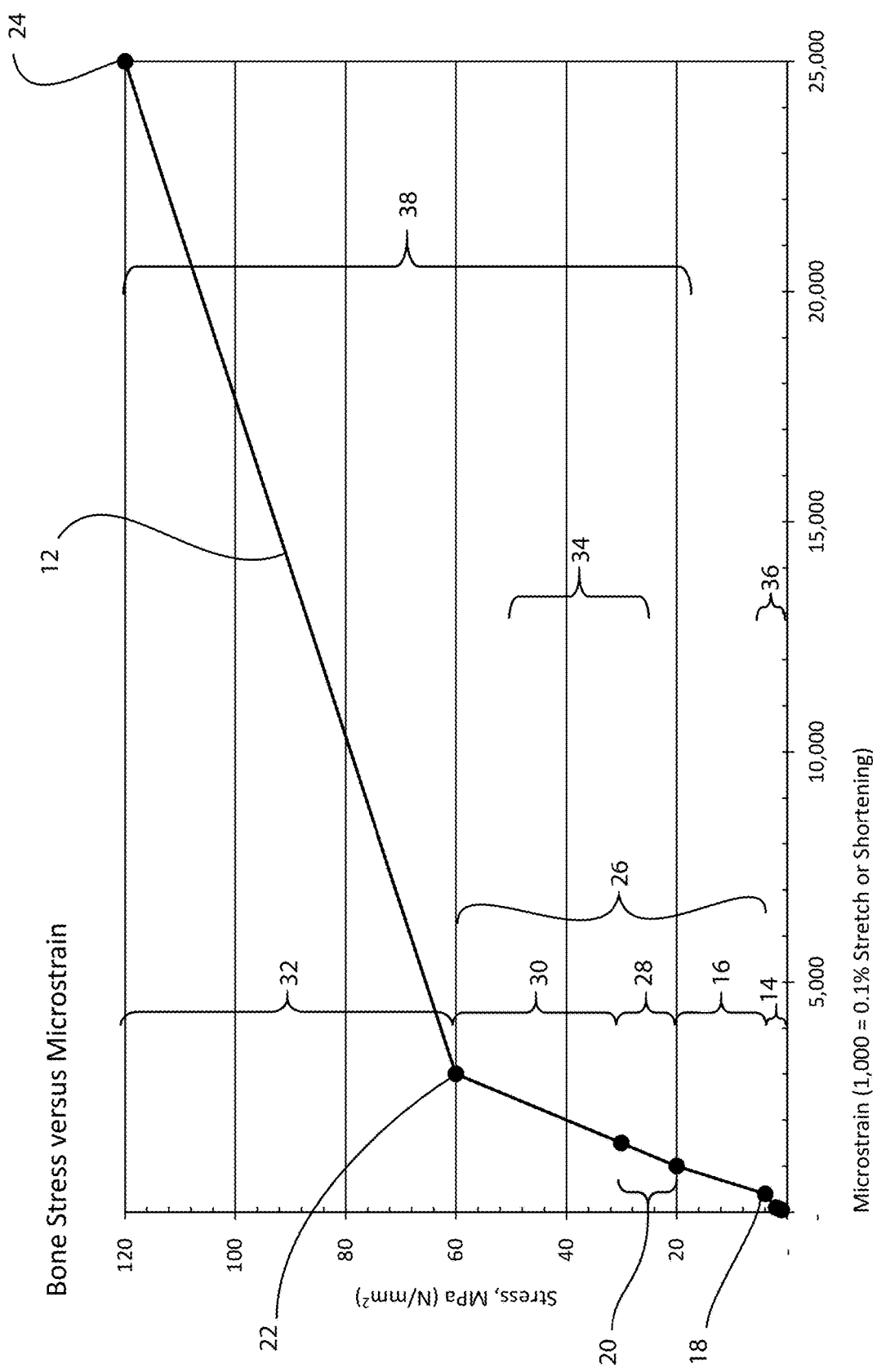
FIG. 1 is a chart of bone stress versus microstrain.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any mechanical form of interaction between two or more entities, including but not limited to sliding and/or bearing. Two components may be functionally coupled to each other even though they are not in direct contact with each other. The term "abutting" refers to items that are in direct physical contact with each other, although the items may not necessarily be attached together.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Definitions

Diminution as used herein—is fracture zone collapse (gap closure) and hardware settling-in. Diminution continues only by sufficient tension remaining in hardware to overstress the contact points and close necrotic and resorption gaps. Under conditions of sustained reduction, and a minimum level of stability, (usually available from conventional fixation hardware, casting and protocols to avoid early load bearing for protection), necrotic bone will all be removed, and live bone triggers the callus reaction, to fill gaps and increase stability.

Callus reaction—is the body's placement (using osteoblasts) of a mechanically weak, but stabilizing material composed mostly of cartilage. Callus is woven bone, that is produced quickly and characterized by haphazard organization of collagen fibers. This is the body's temporary natural reaction to fill the gaps and thereby further stabilize bone that does not remain sufficiently stable for lamellar bone growth from traditional fixation. Callus is eventually replaced by lamellar bone. In many discontinuities, (e.g., with bone fragments available for reduction and compression) this (3 to 4 week stabilization phase) reaction can be largely skipped under desired orthopedic conditions (closed bone gaps, sustained compression, non stress-shielding).

Bone-bridging—(direct to lamellar bone) growth. Existing research studies show and clinical experience of BMG surgeons confirm that fractures healing under the desired orthopedic conditions, (e.g., frequently re-tightened external fixations) lead to the following progressive outcomes;

Osteogenic resorption removes necrotic bone and initial contact points

Sustained bone compression continuously collapses the gaps while maintaining stability The body recognizes that sufficient stability already exists and largely skips the callus reaction, proceeding directly to lamellar bone growth; resulting in about 50% reduction in healing time.

Long bones—Hard, dense bones that provide strength, structure, and mobility to an animal. A long bone has a shaft and two ends. Long bones include the humerus, radius, ulna, metacarpals, femur, tibia, fibula, and metatarsals.

FIG. 1 is a chart of bone stress versus microstrain. A curve 12 illustrates the stress induced in bone as a function of microstrain. A threshold of disuse remodeling 18 is genetically determined and occurs in a first zone 14 between 1 MPa and 4 MPa. A threshold of strengthening 20 is also genetically determined and occurs in a third zone 28, between 20 MPa and 30 MPa. A yield point 22 occurs at 60 MPa. An ultimate strength point 24 occurs at 120 MPa.

Living bone responds to stress and strain within specific ranges by building or removing bone.

Bone atrophy, also known as bone resorption or bone removal, occurs in a first zone 14 at sustained stress levels below 1 MPa to 4 MPa. Bone atrophy may occur due to loss of bone mass or density, creating a condition known as osteopenia, or even osteoporosis. Existing bone fixation hardware relaxes after installation so that the average bone stress is in the first zone 14 or below (completely loose). The relaxed bone-hardware construct may be unstable for load bearing across a discontinuity.

A second zone 16 for live bone reaction to stress exists for stress levels between the threshold of disuse remodeling 18 and the threshold of strengthening 20, in other words between 4 MPa and 20 MPa. Bone experiencing stress in this zone will not be induced by the stress to grow, nor will the bone atrophy. If the fixation hardware fails to provide stability, sufficient to enable load bearing to stress the bone beyond the second zone 16, the bone response is to stabilize itself and may involve formation of a temporary, weak cartilaginous material bridging the discontinuity, followed by formation of a mechanically weak woven bone callus with haphazardly organized collagen fibers.

In a third zone 28 at a genetically determined stress level somewhere between 20 MPa and 30 MPa, in association with the threshold of strengthening 20, bone growth is triggered. Bone growth triggering is optimized by intermittent loading which results in stress passing through the third zone 28 from a level below the third zone 28, sustained by bone hardware, to a level in or above zone 28, for example, by loading the bone intermittently into zone 30. Sustained bone stress in zone 28 may be less than optimal because intermittent load bearing would not subside to levels below the trigger zone, the threshold of strengthening 20. Sustained stress by hardware in zone 30 would further shield the bone from experiencing stress fluctuations by intermittent loading. On the other hand, insufficient sustained load by the hardware (for example, hardware which produces average bone stress in the mid or lower end of zone 16) would not create sufficient friction and stability in the discontinuity to prevent micromotion during early loading. Thus, for optimal bone growth the hardware should sustain average stress in bone at about 18 MPa. Doing so would be ideal for mechanically stabilizing the bone portions across the discontinuity while facilitating osteogenic stimulation by limited intermittent mechanical loading. Lamellar bone bridging can occur if and only if bone is subjected to intermittent stress levels at or above the threshold of strengthening 20 without micromotion occurring between fragments in the discontinuity. Hardware sustaining an average of 18 MPa will create stability for load bearing across a discontinuity, and may encourage bone bridging: direct lamellar bone growth across the discontinuity. The hardware disclosed herein sustains an average of 18 MPa compression after diminution to stabilize the discontinuity in friction such that load bearing can occur without causing micro-movement between the surfaces of the discontinuity. Average bone stress sustained by the hardware will be just below the third zone 28, i.e., at about 18 MPa. This level of stress across the discontinuity is sufficient to create friction to stabilize the discontinuity to resist micro-movement during load bearing. Such load bearing will intermittently increase the stress level experienced by the bone into the third zone 28 or a fourth zone 30 discussed below, then subside to a sustained stress level in the upper range of the second zone 16, i.e., 18 MPa. The hardware disclosed herein thus mechanically stabilizes the discontinuity to create conditions that will optimize bone growth. Optimal bone growth occurs from intermittent bone stress in the third zone 28 and the fourth zone 30 between 20 MPa and 60 MPa, as the bone intermittently and repeatedly passes through the bone growth trigger stress, the threshold of strengthening 20 somewhere in zone 28.

Thus bone in a discontinuity fixated by the hardware disclosed herein will experience adequate stress in a zone 26 between the threshold of disuse remodeling 18 and the yield point 22, in other words between 1 MPa-4 MPa and 60 MPa, due to the combination of sustained average compressive stress maintained by internal fixation hardware at about 18 MPa, to maintain stability through friction, plus the stress from early load bearing.

In a fourth zone 30 between 30 MPa and 60 MPa, bone growth will continue as stress increases, but stress shielding would occur if hardware sustained even localized bone stresses that approach 60 MPa. Sustained average bone stresses in the fourth zone 30 may result in stress shielding because the bone stresses would not be intermittently passing through the bone growth trigger stress, the threshold of strengthening 20 in zone 28. Sustained loads from hardware in the fourth zone 30 may be stable for load bearing across a discontinuity, but suboptimal for triggering bone growth across the discontinuity.

Bone remodeling, also known as bone resorption or bone removal, occurs in a fifth zone 32 at sustained stress levels above the yield point 22. Conventional screws installed to produce local bone stress in zone 32, perhaps in an attempt to overcome screw loosening, in fact cause remodeling to remove the overstressed bone.

Healthy human bone can resist short duration stress up to the ultimate strength point 24, particularly durations less than or equal to 1 second. Stress sustained longer than 1 second may trigger the body to begin resorbing the overstressed bone. Bone failure (fracture) may occur at stress levels above the ultimate strength point 24.

Industry standard devices may be installed so as to induce average bone stress in an industry standard installed stress zone 34 which is known to vary widely, and which may be between the threshold of strengthening 20 and the yield point 22. However, as diminution occurs, the bone stress declines to an industry standard sustained stress zone 36 equivalent to the first zone 14 and/or the low end of the second zone 16. This occurs because rigid hardware cannot deflect to maintain desirable bone stresses, or because spring-loaded hardware does not provide sufficient load to maintain desirable bone stresses. Relaxed hardware is unlikely to stabilize the discontinuity sufficiently to sustain intermittent load bearing. Rather, the unstable discontinuity requires protection against loading so as to avoid micro-motion and possible non-union. Protection may be by casting, bracing, patient instructions to avoid loading, etc. When a discontinuity is only partially stabilized, i.e., by casting and/or relaxed hardware, the body reacts by forming callus to further stabilize the discontinuity to prevent micromotion.

The devices disclosed herein may be installed in the industry standard installed stress zone 34, for example, at 30 MPa. Due to their particular load versus elongation characteristics, after diminution, the disclosed devices provide sustained bone stresses in the upper range of the second zone 16 or in the lower range of the third zone 28, i.e., 18 MPa, and function in an allowable dynamic stress zone 38 between 18 MPa and the ultimate strength point 24 under intermittent high load, but are optimally designed to facilitate early loading for bone to experience stress between 18 MPa and 60 MPa.

This disclosure sets forth solutions for a specific scenario of a long bone with an 18.2 mm shaft diameter and an oblique mid-shaft fracture, osteotomy, or other discontinuity in a plane inclined 30° with respect to the longitudinal axis of the bone. This scenario is referred to as the example discontinuity and is illustrated in FIG. 27C. A 30° osteotomy is formed in a metatarsal bone of a mature sheep. The nominal bone diameter transverse to the major axis is 18.2 mm. The example discontinuity is employed to illustrate the principles of the technology. The principles disclosed herein and in U.S. Provisional Application Ser. Nos. 62/080,893 and 62/080,954 are applicable to other scenarios with different bone and discontinuity geometries; the local bone stress levels in the vicinity of the discontinuities still follow the principles laid out above.

One way to secure the example discontinuity is with a compression system that includes three bicortical spring washer bone screws that extend across the discontinuity perpendicular to the plane of the discontinuity. The screws may be installed with a center-to-center spacing of 8.5 mm and with the heads on alternating sides of the bone.

One example of a spring washer bone screw suitable to the example discontinuity has the following dimensions: outer diameter of screw shank is 3 mm, major diameter of threads is 4.5 mm, thread spacing (pitch) is 1.5 mm, outer diameter of head is 8 mm, and overall length is 21 mm to 29 mm. In this example, the bone screw includes a series stack of two spring washers 86 as disclosed below.

When three spring washer bone screws having the preceding dimensions are installed bicortically across the example discontinuity, each screw with an installation load of 3000 N, each bone screw dynamically adjusts to provide an 1800 N load after diminution from the installed state. The 3000 N installation load for each bone screw causes an average of 30 MPa of bone stress in the example discontinuity. The 1800 N post-diminution load causes an average bone stress of 18 MPa in the example discontinuity. The example discontinuity would be stabilized for intermittent loading. Such loading would cause intermittent stress passing through the threshold of strengthening 20, the third zone 28, and perhaps into the fourth zone 30. Occasional high stress in the fifth zone 32 would be tolerated as well. After intermittent loading or high stress, the system would revert back to the 1800 N post-diminution load sustained by the hardware.

In other examples, the installation load may be between 1500 N and 2500 N, corresponding to an average bone stress in the vicinity of the discontinuity which is less than or equal to 58 MPa. The post-diminution load may be 1000 N after 0.075 mm to 0.200 mm of diminution, corresponding to an average bone stress in the vicinity of the discontinuity which is 20 MPa. An intermittent high load of 10,000 N is sustained by each bone screw in healthy normal bone with minimal displacement, after which the bone screw will go back to the post-diminution load. An intermittent high load of 13,000 N is sustained by each spring washer. This load flattens the spring washer and corresponds to an average bone stress in the vicinity of the discontinuity which would exceed 120 MPa.

Figure 2A:
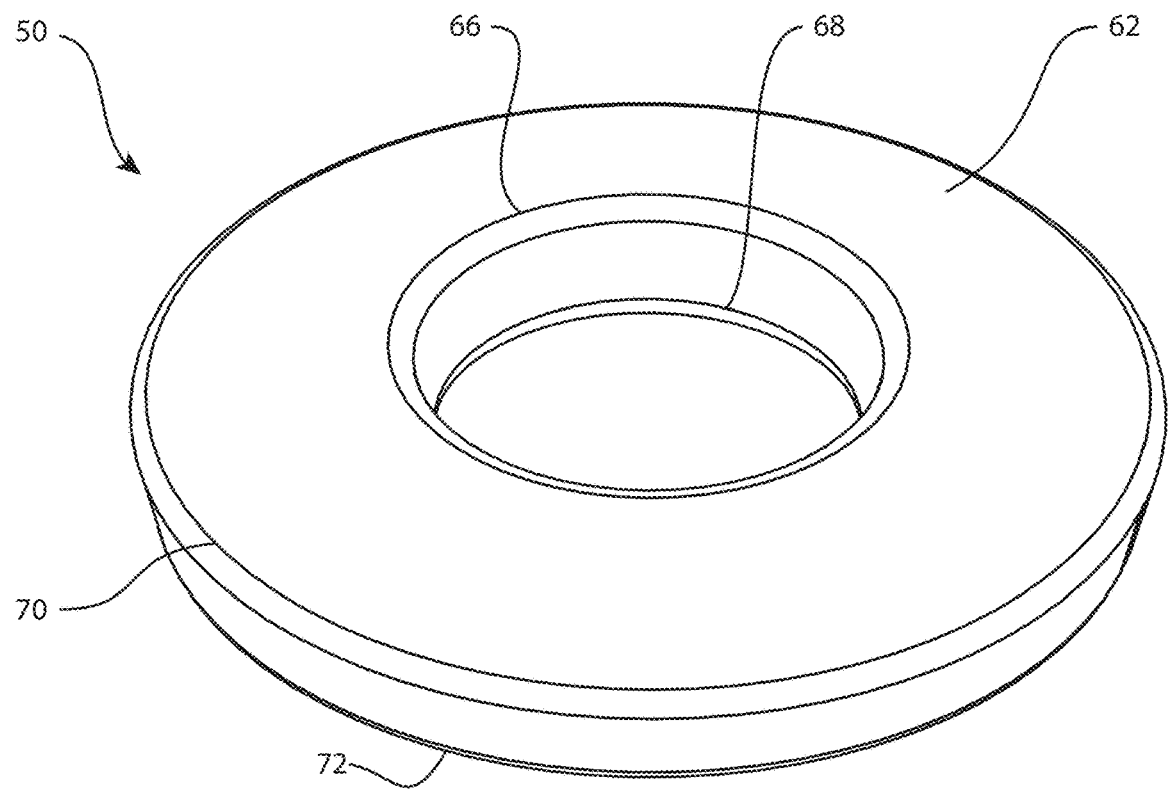
FIG. 2A is a top isometric view of a spring washer.
Figure 2B:
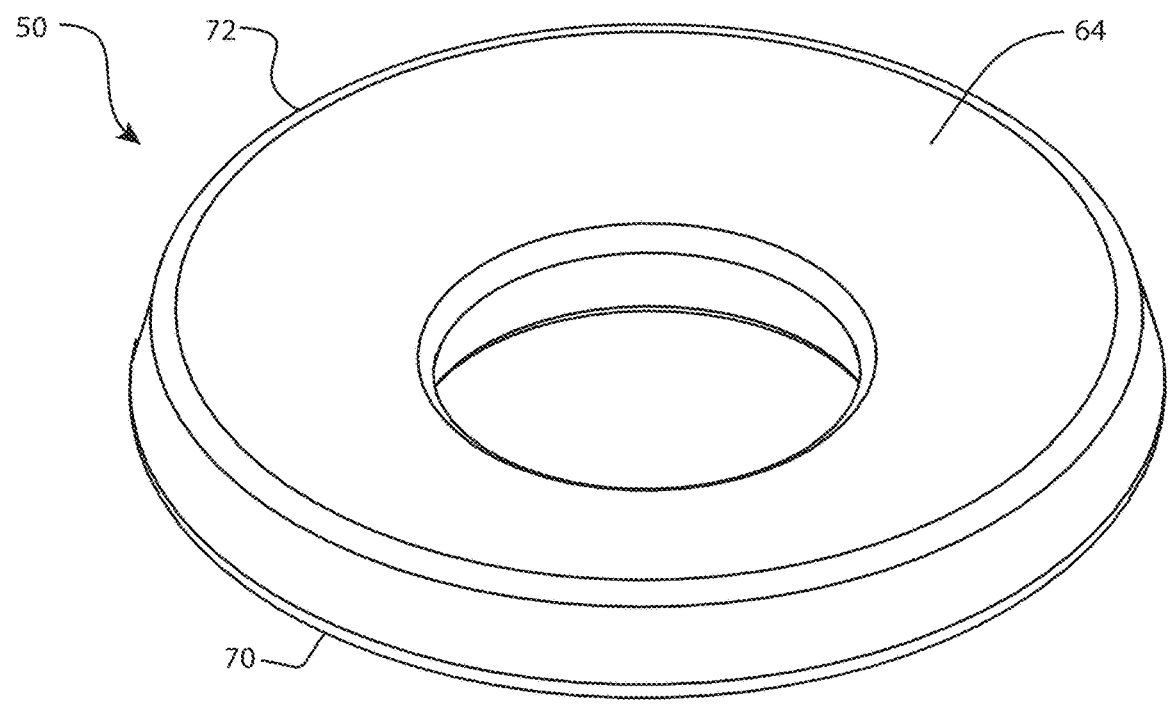
FIG. 2B is a bottom isometric view of the spring washer of FIG. 2A.
Figures 2C, 2D:
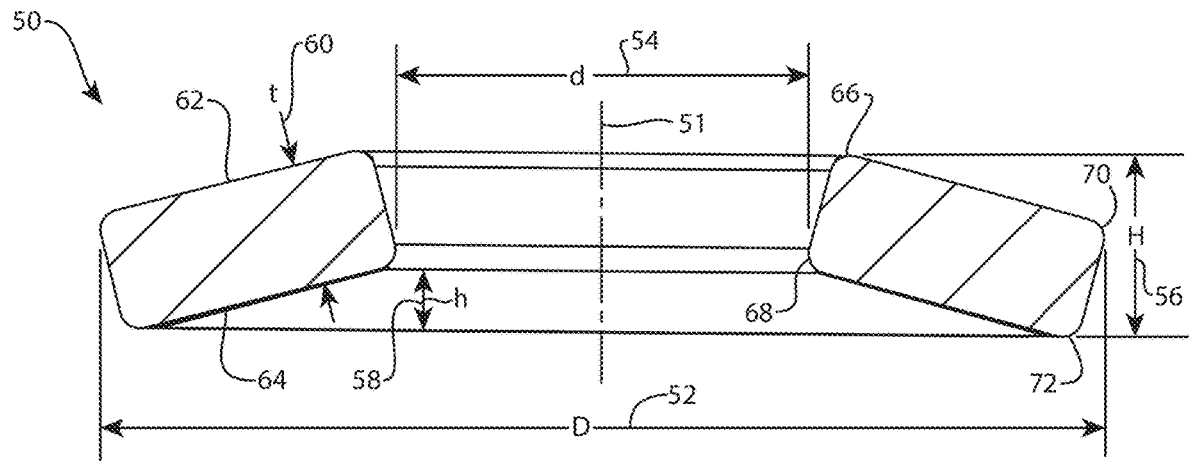
FIG. 2C is a cross sectional view of the spring washer of FIG. 2A.
FIG. 2D is a table listing dimensions and ratios for various spring washers.

Referring to FIGS. 2A-2C, a spring washer 50 is illustrated. The spring washer 50 may also be referred to as a Belleville washer or spring, a coned disc spring, a conical spring, or a cupped spring washer. Referring to FIG. 2C, the spring washer 50 is a frustoconical ring having a central axis of revolution 51, an outer diameter (D) 52, an inner diameter (d) 54, an overall height (H) 56, an inner height (h) 58, and a thickness (t) 60. The spring washer includes a convex upper surface 62, a concave lower surface 64, an inner upper edge 66, an inner lower edge 68, an outer upper edge 70, and an outer lower edge 72. These edges 66, 68, 70, 72 may form sharp corners, but preferably the edges are rounded, beveled, chamfered, or otherwise blunted.

Referring to FIG. 2D, a table lists dimensions for various sizes of the spring washer 50. Each size is named with its outer diameter (D) 52×inner diameter (d) 54×thickness (t) 60. However, spring washers that share the same "D×d×t" name may have different overall heights (H) 56 or inner heights (h) 58. Therefore, each spring washer size is given a unique reference number to avoid confusion. The table includes an 8×3.2×0.35 spring washer 74, an 8×3.2×0.82 spring washer 76, an 8×3.2×1.10 spring washer 78, an 8×3.4×0.82 spring washer 80, an 8×3.4×1.10 spring washer 82 with H=1.211 mm and h=0.111 mm, an 8×3.4×1.10 spring washer 84 with H=1.232 mm and h=0.132 mm, and an 8×3.4×1.10 spring washer 86 with H=1.295 mm and h=0.200 mm.

Note that spring washers 74, 76, 78 have an inner diameter (d) 54 of 3.2 mm, while spring washers 80, 82, 84, 86 have an inner diameter (d) 54 of 3.4 mm. For a given outer diameter (D) 52 and thickness (t) 60, the 3.2 mm inner diameter (d) 54 is slightly more flexible than the 3.4 mm inner diameter (d) 54. However, the 3.2 mm inner diameter (d) 54 is such a close fit to a 3 mm screw shank diameter that the inventors chose to use the 3.2 mm diameter with screws having separate heads coupled to the screw shank with an interconnection. The 3.4 mm inner diameter (d) 54 was developed for use with screws having integral heads; the spring washer 80, 82, 84, 86 may be rolled or threaded along the distal external threads of the screw. Somewhat larger inner diameters are also contemplated for at least this reason.

Spring washers may be used singly or in multiples. Any embodiment herein that illustrates a single spring washer may instead include multiple spring washers, and vice versa.

Multiple spring washers may be stacked in parallel, so that the concave side 64 of one spring washer rests against, or nests within, the convex side 62 of another washer. The theoretical load capacity of a parallel stack of N spring washers is equal to N times the load capacity of a single spring washer, and the theoretical deflection of the stack is equal to the deflection of a single spring washer. However, a parallel stack of spring washers tends to experience more hysteresis than a single spring washer or a series stack due to friction between adjacent essentially congruent concave sides 64 and convex sides 62.

Multiple spring washers may be stacked in series, so that the convex sides 62 or concave sides 64 of two adjacent spring washers are facing. This arrangement may be referred to as an opposing stack. The theoretical deflection of a series stack of N spring washers is equal to N times the deflection of a single spring washer, and the theoretical load capacity of the stack is equal to the load capacity of a single spring washer. A series stack of spring washers experiences almost the same hysteresis as a single spring washer because the contacting surfaces move congruently rather than sliding against each other as they do in a parallel stack.

Multiple spring washers may of course be stacked in a mixed stack that includes some parallel spring washers and some series spring washers.

Figure 28A:
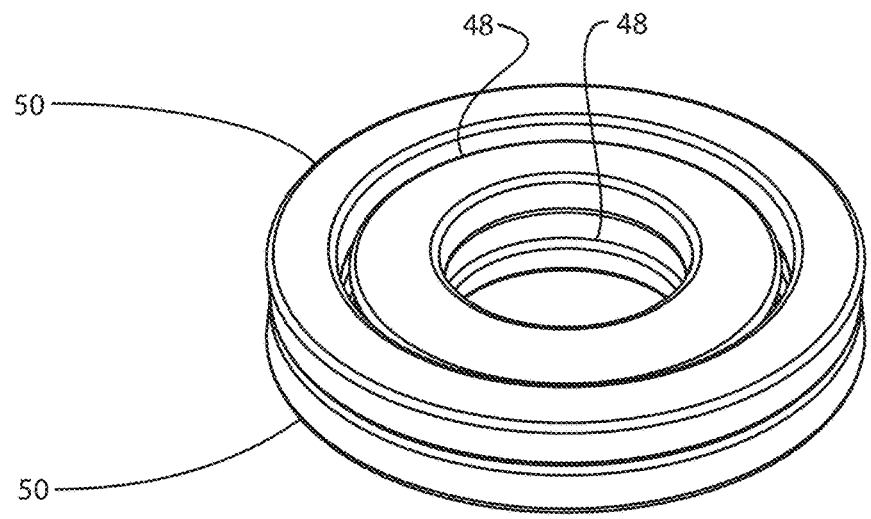
FIG. 28A is an isometric view of a series stack of inner spring washers nested inside a series stack of outer spring washers.
Figure 28B:
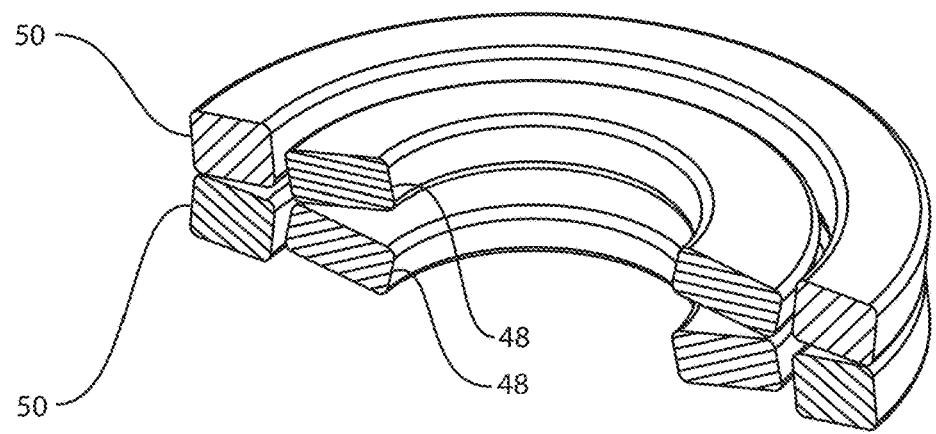
FIG. 28B is an isometric cross sectional view of the spring washer stack of FIG. 28A.
Figure 28C:
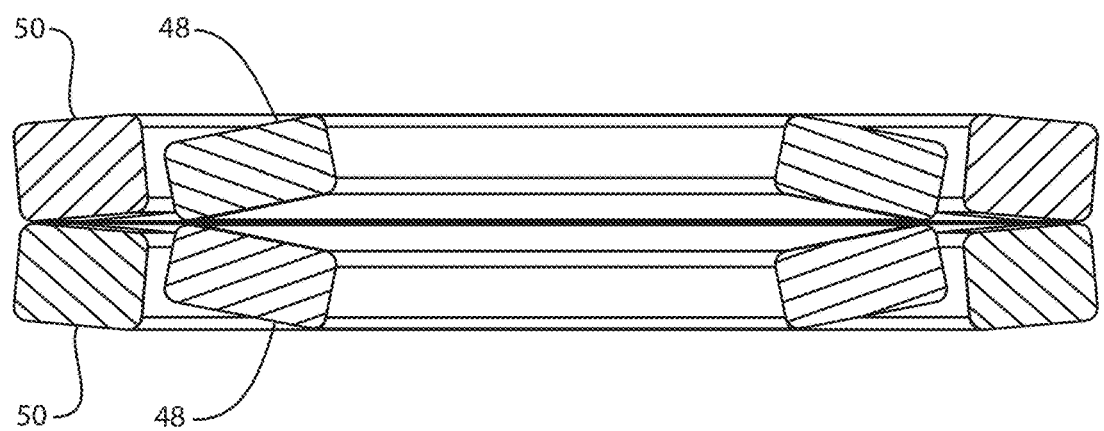
FIG. 28C is a cross sectional view of the spring washer stack of FIG. 28A.

Referring to FIGS. 28A-28C, multiple spring washers may be provided in a set that includes an outer spring washer 50 and an inner spring washer 48 that nests within the inner diameter (d) 54 of the outer spring washer 50. A set of spring washers 48, 50 may be used alone, or two or more sets of spring washers may be used together in a parallel stack, a series stack, or a mixed stack. Furthermore, the outer spring washers 50 may be stacked differently than the inner spring washers 48. FIG. 28 illustrates two sets of spring washers 48, 50 in a double series stack.

FIG. 3 is a table listing physical characteristics of 316L stainless steel. FIG. 4 is a table listing physical characteristics of titanium ASTM F136. The spring washers disclosed herein may be fabricated from titanium for use in patients who are intolerant to stainless steel, for use in patients with osteoporotic bone where lower spring forces are desired, or to satisfy other design criteria.

The spring washers disclosed herein may be fabricated from a stainless steel with a tensile yield strength greater than 1276 MPa and an ultimate tensile strength greater than 1600 MPa. The spring washer may be fabricated from an essentially nickel-free high-nitrogen austenitic stainless steel with a Young's modulus of 200 GPa, a tensile yield strength of 1351 MPa which after cold working may approach 1862 MPa, and an ultimate tensile strength of 1655 MPa which after cold working may approach 2206 MPa. A stainless steel meeting this description is sold under the trademark BIODur 108™. FIG. 5 is a table listing physical characteristics of the stainless steel sold under the trademark BIODur 108™.

Referring to FIGS. 3-5, elastic spring constant behavior is dependent on the modulus of elasticity of a material, not so much its strength. The modulus of elasticity for commercially pure titanium (CP Ti) is 110 GPa. The modulus of elasticity for A302 stainless steel is 193 GPa. The modulus of elasticity for A316 stainless steel and the stainless steel sold under the trademark BIODur 108™ is 200 GPa. The modulus of elasticity may not change much due to material strength increasing treatments such as heat treatments, cold work treatments, and the like. However, the inventors recognized that increased material strength is directly related to high load capacity of the spring washers disclosed herein, because allowable stress and hence load can be higher. Increased material strength permits the spring washers to operate within the nonlinear inelastic portion of the stress-strain curve, for example, near the ultimate strength of the material.

Normally, spring washers are designed to survive fatigue conditions of hundreds of thousands or millions of cycles. With such a fatigue design criteria, spring washers are designed to avoid the nonlinear inelastic portion of the stress-strain curve, especially the ultimate strength of the material. However, as set forth below, the technology disclosed herein minimizes or eliminates fatigue conditions by, for example, straining the washer perhaps 0.500 mm to 0.200 mm during installation. Then during diminution, the springs quickly relax, substantially to perhaps 40% to 60% of their installed stress. In the relaxed state the springs sustain bone compression in the optimal stress zone for lamellar bone bridging. Accelerated healing creates healed bone that further shields the spring washer and related hardware from load cycles. Further, hardware using the technology maintains reduction under intermittent high loads that flatten the spring washer and return to optimal bone compression afterwards.

FIG. 6 is a data sheet for the 8×3.2×0.35 spring washer 74 with H=0.70 mm and h=0.35 mm. The spring washer 74 may be used in a parallel stack, with each washer supporting 285 N at 0.30 mm extension upon installation. For example, the spring washer 74 may be used in a parallel stack of seven spring washers. The parallel stack of seven spring washers has a theoretical load capacity of 1995 N and a theoretical deflection of 0.30 mm. Note that the data sheet states that the stresses S2 ($\sigma_{II}$) are too high for standard fatigue conditions. Therefore, the spring washer 74 falls outside customary design parameters for spring washers.

Figure 7A:
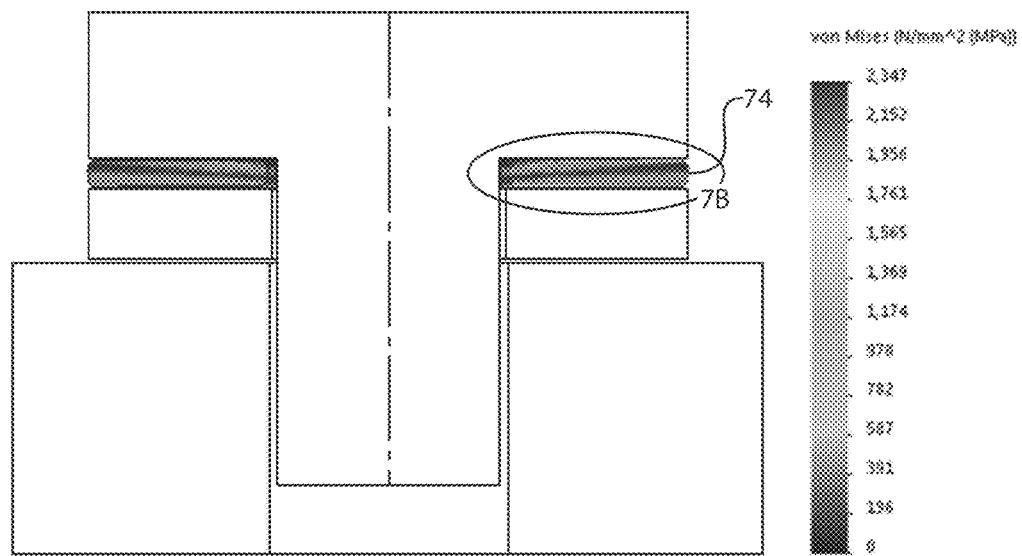
FIG. 7A is a finite element analysis contour plot of von Mises stress in a single spring washer of FIG. 6.
Figure 7B:
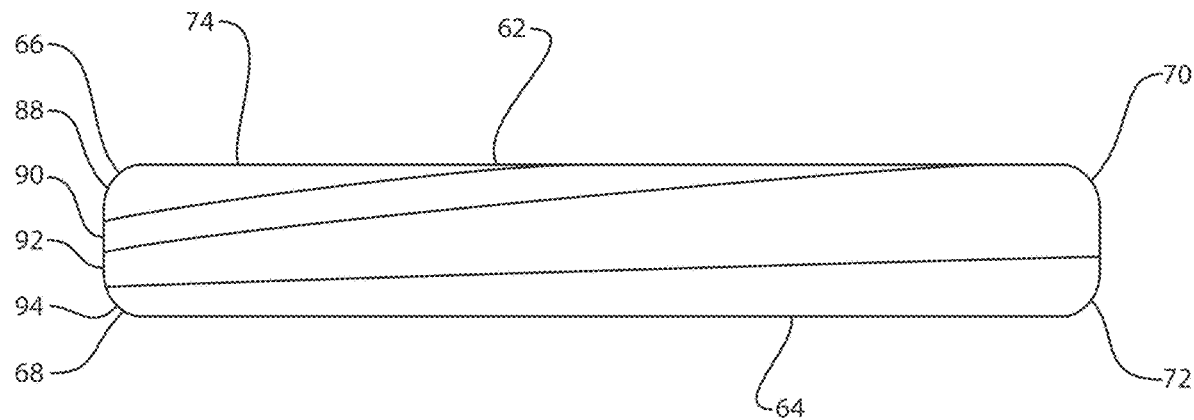
FIG. 7B is an enlarged detail view of one side of the spring washer of FIG. 7A.

FIG. 7A is a finite element analysis contour plot of von Mises stress in a single spring washer 74 under 285 N at 0.30 mm extension. FIG. 7B is an enlarged detail view of one side of the spring washer 74, with isostress contour lines that divide the cross-sectional area of the spring washer 74 into a high compressive stress zone 88, a moderate compressive stress zone 90, a neutral stress zone 92, and a moderate tensile stress zone 94. The high compressive stress zone 88 controls the design in this example. The high compressive stress zone 88 and the moderate compressive stress zone 90 together may be referred to as a compression ring extending partway across the upper surface 62 from the inner upper edge 66. The moderate tensile stress zone 94 may be referred to as a tension plate extending across the lower surface 64 between the inner lower edge 68 and the outer lower edge 72.

Figure 8:
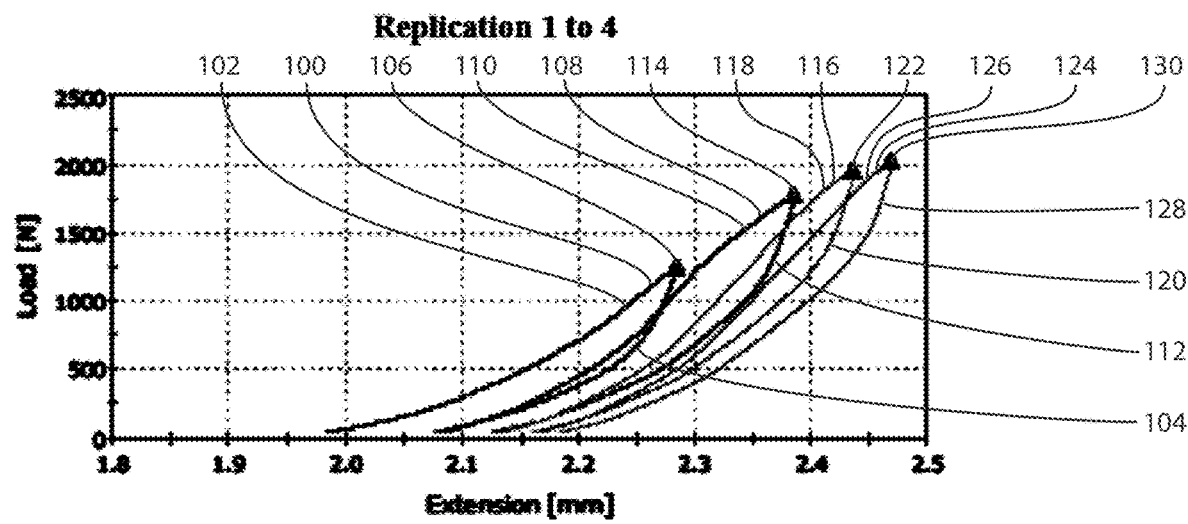
FIG. 8 is a chart of load versus extension for four consecutive loading cycles of a parallel stack of seven spring washers of FIG. 6 to 0.30 mm extension.

FIG. 8 is a chart of load versus extension for four consecutive loading cycles of a parallel stack of seven spring washers 74 taken to 0.30 mm extension. The parallel stack of seven spring washers 74 has a stack height of 2.76 mm. The first loading cycle 100 includes a loading portion 102 during which the stack is compressed, an unloading portion 104 during which the stack is decompressed, and a first peak load 106 at 0.30 mm extension. The second loading cycle 108 includes a loading portion 110, an unloading portion 112, and a second peak load 114 at 0.30 mm extension. The third loading cycle 116 includes a loading portion 118, an unloading portion 120, and a third peak load 122 at 0.30 mm extension. The fourth loading cycle 124 includes a loading portion 126, an unloading portion 128, and a fourth peak load 130 at 0.30 mm extension. The peak loads 106, 114, 122, 130 may be referred to as cold working loads, intended to occur before an installation load. Each loading cycle exhibits appreciable separation between the loading and unloading portions of the curve, indicative of high hysteresis. The loading portion of each curve has higher loads for a given extension than does the unloading portion of each curve. This is typical of a parallel stack of spring washers. Each consecutive loading cycle reaches a progressively higher peak load at 0.30 mm extension, indicative of cold work strain hardening the spring washers 74.

Figure 9:
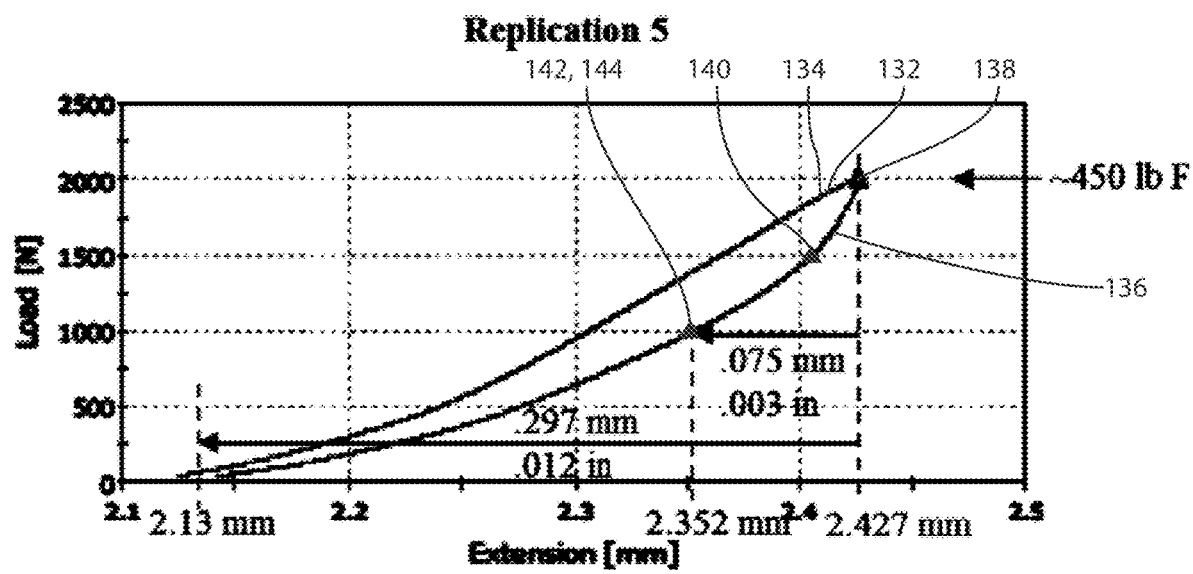
FIG. 9 is a chart of load versus extension for a fifth loading cycle of the spring washer stack of FIGS. 8 to 0.30 mm extension.

FIG. 9 is a chart of load versus extension for a fifth loading cycle of the parallel stack of seven spring washers 74, also taken to 0.30 mm extension. The fifth loading cycle 132 includes a loading portion 134, an unloading portion 136, and a fifth peak load 138 at 0.30 mm extension. The fifth peak load 138 may be referred to as an installation load. The fifth peak load 138 is 2000 N, equal to the fourth peak load 130 of FIG. 8, indicating that no further cold work strain hardening occurred during the fifth loading cycle 132. Along the unloading portion 136, point 140 corresponds to a 1500 N load, point 142 corresponds to a 1000 N load, and point 144 corresponds to a diminution of 0.075 mm from the installed load, in this instance the fifth peak load 138. In this example, points 142 and 144 are identical and correspond to a 1000 N load sustained by this spring stack following 0.075 mm of diminution. This also corresponds to 0.088 mm diminution closure capacity of the spring stack in a system with a screw and bone at 1000 N of sustained load. Note that during installation, in addition to compression of the spring stack, the screw elongates and the physical dimension of the bone compressed by the screw shortens. The bone screw, the bone itself and the spring stack contribute to diminution closure. The contribution to closure by the bone screw and bone are very small relative to the spring stack and their capacity would be quickly exhausted without the spring stack. If insufficient combined capacity exists to accommodate diminution, the screw will loosen, closure will cease, and the discontinuity will become unstable with the corresponding exposure to micro-movement from load bearing.

Recognizing that a small spring travel and a very high load capacity was desirable, the ratio of inner height to thickness (h/t, FIG. 2D) and the ratio of outer diameter to thickness (D/t, FIG. 2D) were increased well beyond industry standards in the following spring washers 76, 78, 80, 82, 84, 86. The increased h/t ratio provides a functional inner height after cold forming that accommodates diminution.

Figure 10:
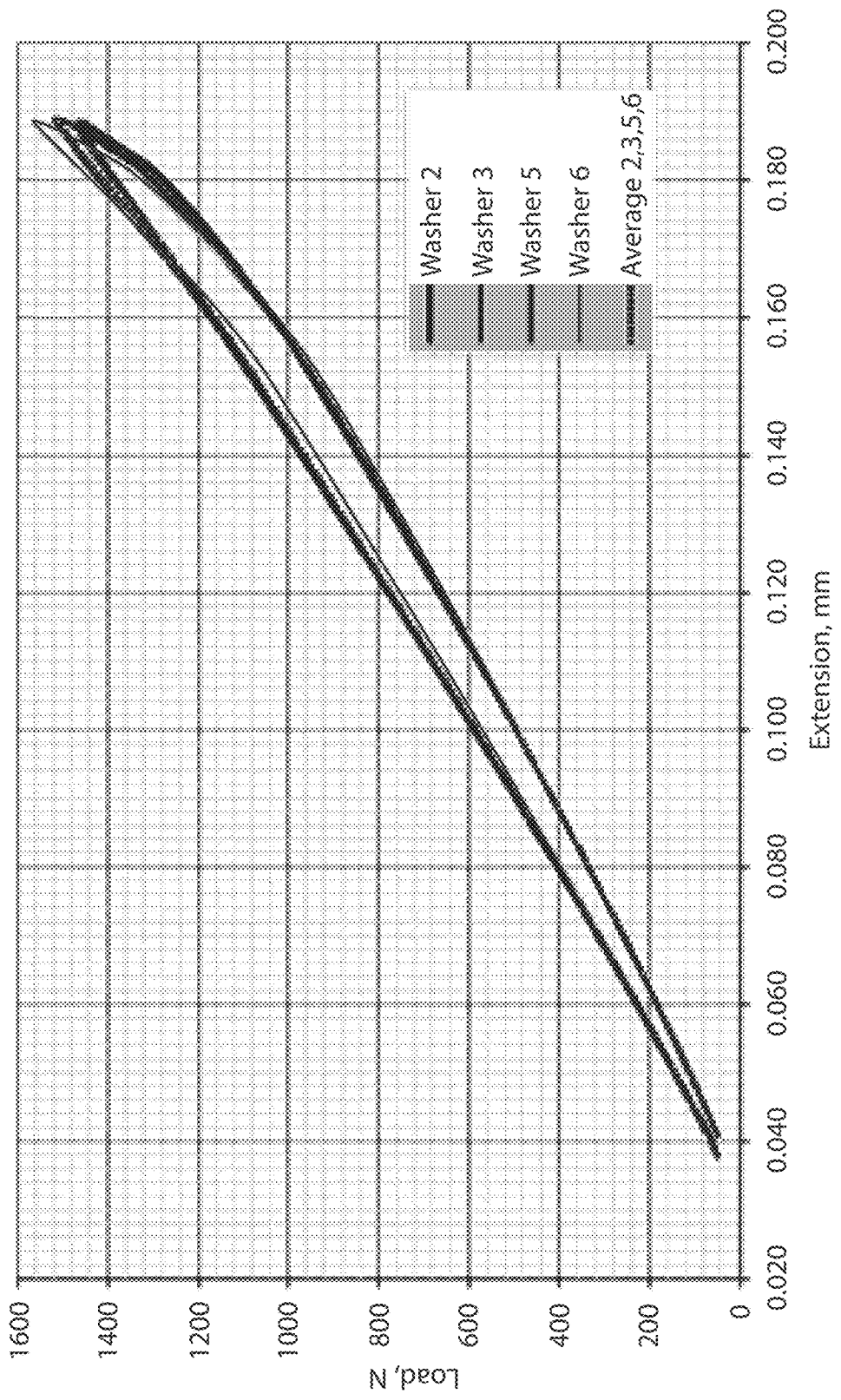
FIG. 10 is a chart of load versus extension for four individual 8×3.2×0.82 spring washers, each subjected to a single loading cycle to 0.15 mm extension, and a data series for the average performance of the four spring washers.

FIG. 10 is a chart of load versus extension for four individual 8×3.2×0.82 spring washers 76, each subjected to a single loading cycle taken to 0.189 mm extension. FIG. 10 also includes a data series for the average performance of the four spring washers 76.

Figure 11:
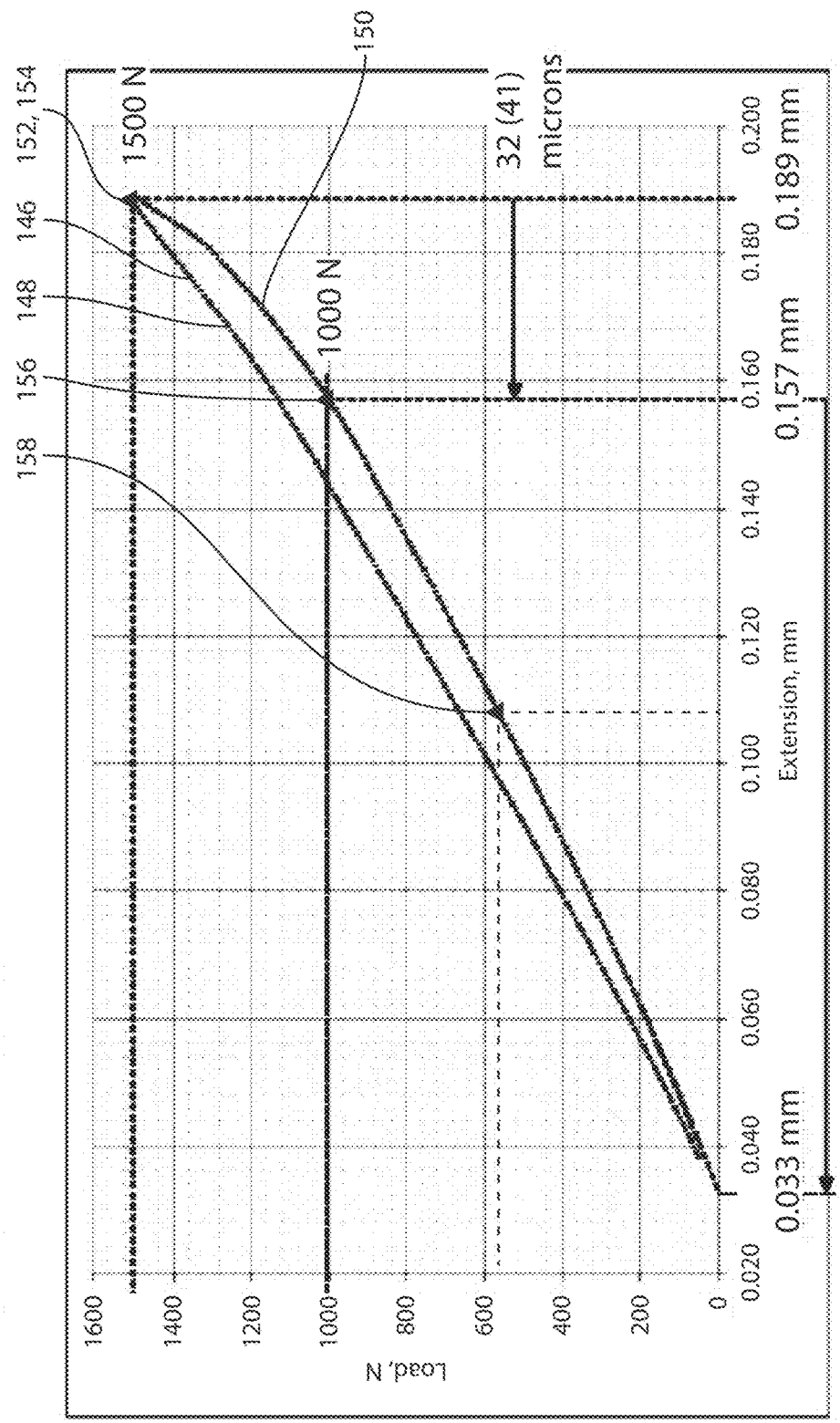
FIG. 11 is a chart of load versus extension for the average performance of the spring washers of FIGS. 10 to 0.189 mm extension.

FIG. 11 is a chart of load versus extension, showing the data series for the average performance of the four spring washers 76 from FIG. 10. The average loading cycle 146 includes a loading portion 148, an unloading portion 150, and an average peak load 152 at 0.189 mm extension. The average peak load 152 may be referred to as an installation load. The average peak load 152 for a single spring washer 76 was 1500 N at 0.189 mm extension. Along the unloading portion 150, point 154 corresponds to a 1500 N load, point 156 corresponds to a 1000 N load, and point 158 corresponds to a diminution of 0.075 mm from the installed load, in this instance the average peak load 152. In this example, points 152 and 154 are identical.

Figure 12A:
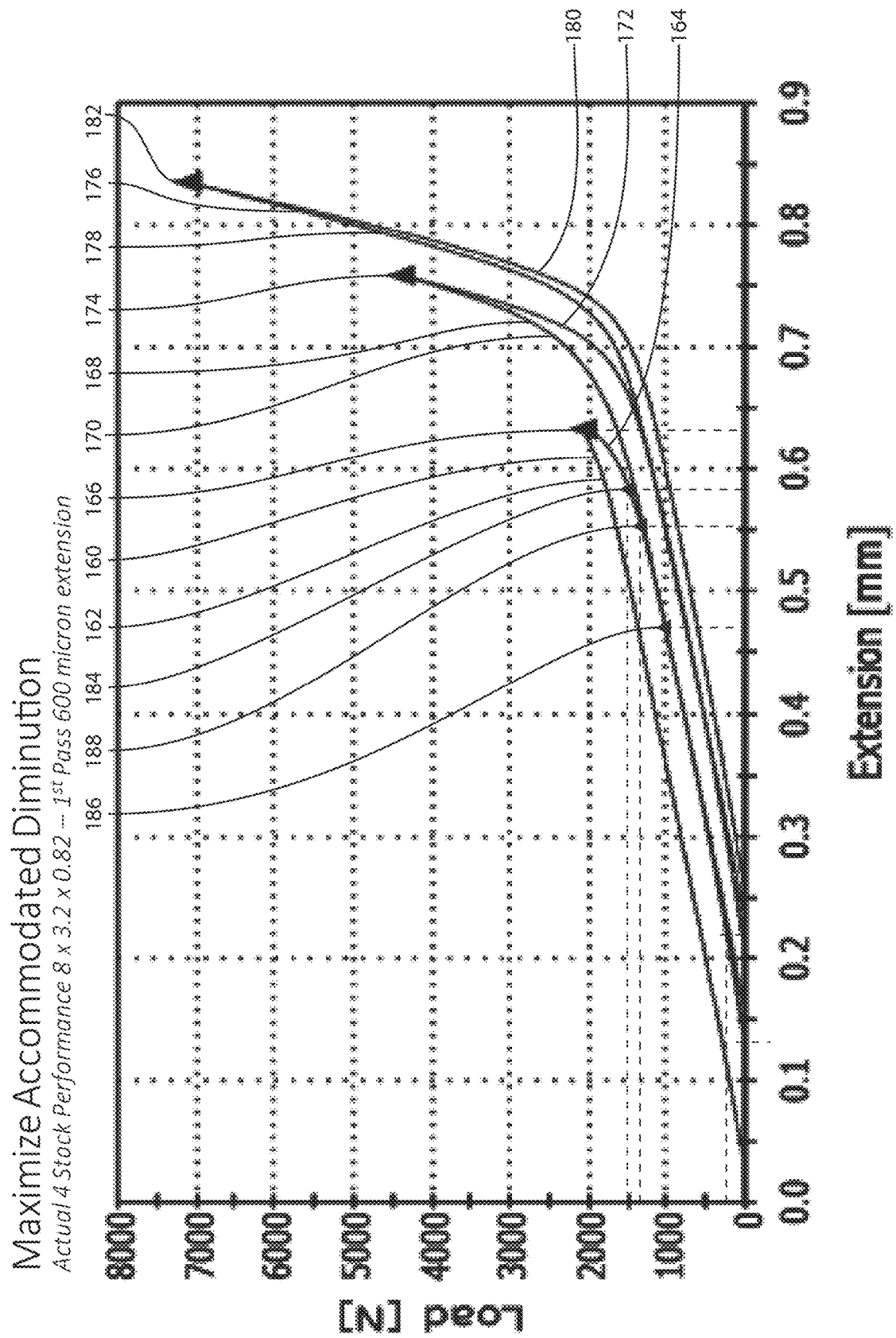
FIG. 12A is a chart of load versus extension for three consecutive loading cycles of a series stack of four spring washers of FIGS. 10 to 0.60 mm extension with selected points identified along the unloading portion of the first loading cycle.

FIG. 12A is a chart of load versus extension for three consecutive loading cycles of a series stack of four spring washers 76 taken to 0.60 mm extension. The first loading cycle 160 includes a loading portion 162, an unloading portion 164, and a first peak load 166 at 0.630 mm extension. The second loading cycle 168 includes a loading portion 170, an unloading portion 172, and a second peak load 174 at 0.60 mm extension. The third loading cycle 176 includes a loading portion 178, an unloading portion 180, and a third peak load 182 at 0.60 mm extension. The peak loads 166, 174, 182 may be referred to as installation loads. The first peak load 166 is 2000 N at 0.630 mm extension. Along the unloading portion 164, point 184 corresponds to a 1500 N load, point 186 corresponds to a 1000 N load, and point 188 corresponds to a diminution of 0.075 mm from the installed load, or first peak load 166.

Figure 12B:
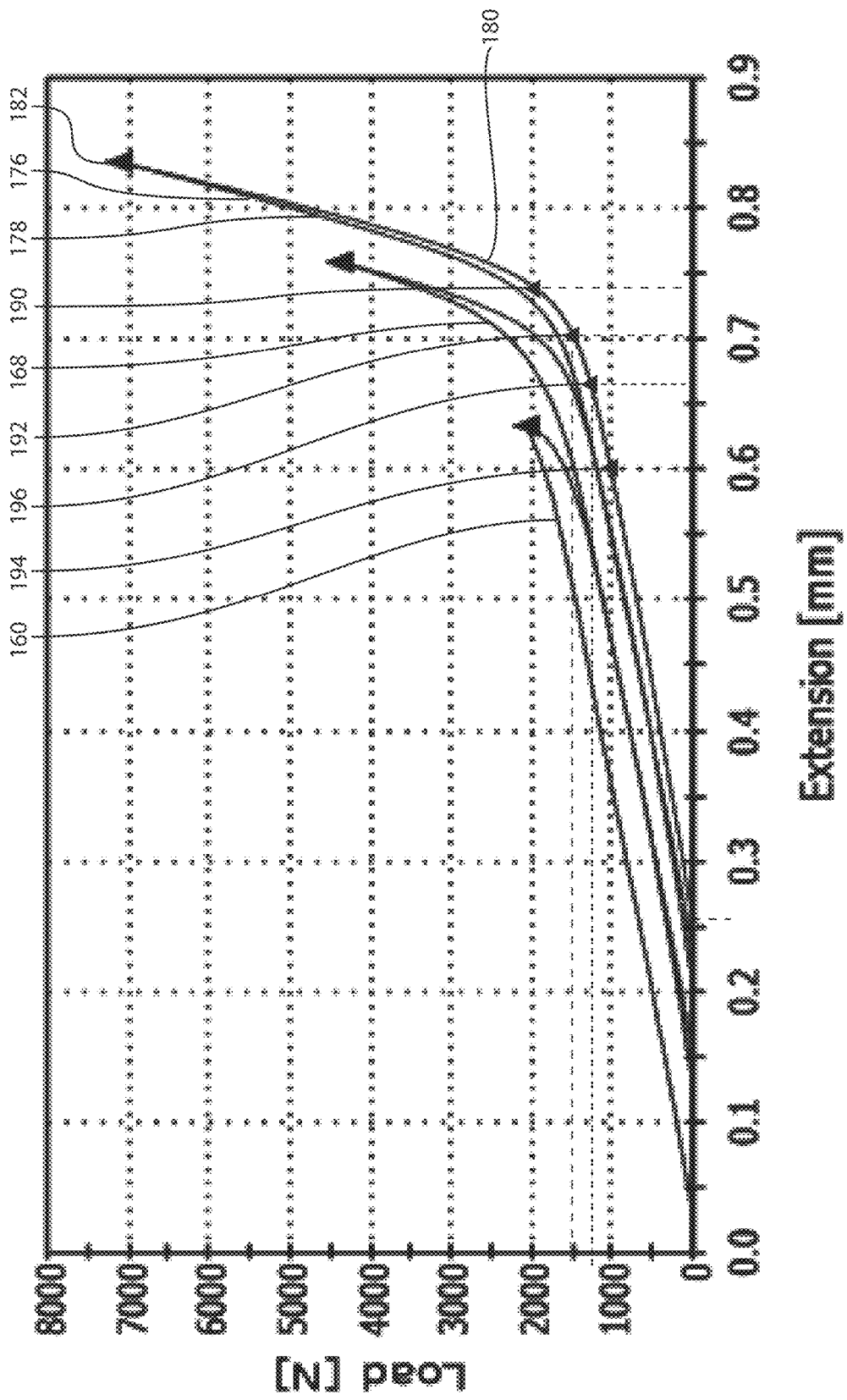
FIG. 12B is the chart of FIG. 12A, with selected points identified along the unloading portion of the third loading cycle.

FIG. 12B is the chart of FIG. 12A, with selected points identified along the third loading cycle 176. Along the unloading portion 180, point 190 corresponds to an installation load of 2000 N, point 192 corresponds to a 1500 N load, point 194 corresponds to a 1000 N load, and point 196 corresponds to a diminution of 0.075 mm from the installed load 190.

Figure 15:
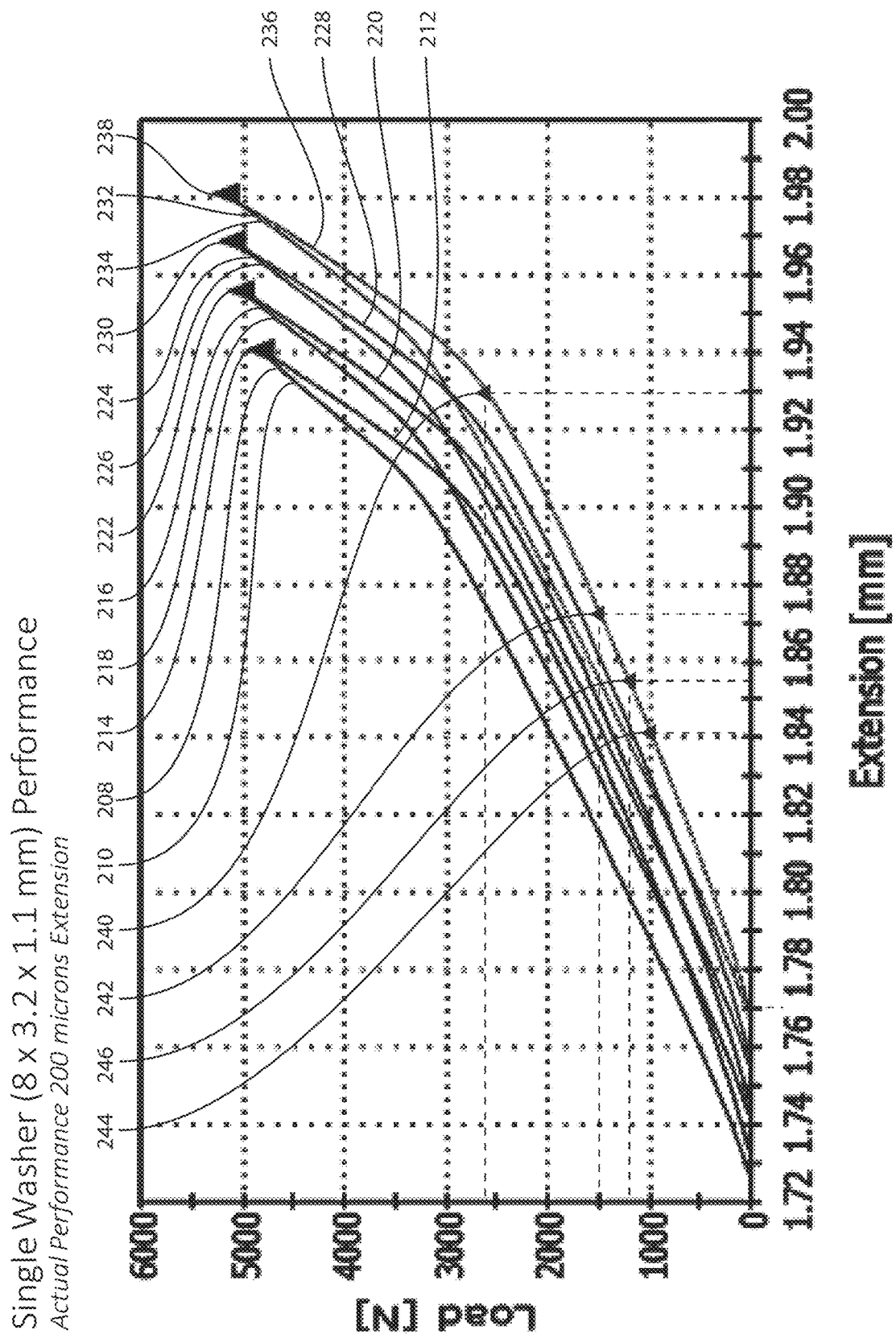
FIG. 15 is a chart of load versus extension for four consecutive loading cycles of a single 8×3.2×1.1 spring washer to 0.20 mm extension.

FIG. 15 is a chart of load versus extension for four consecutive loading cycles of a single 8×3.2×1.1 spring washer 78 to 0.20 mm extension. The first loading cycle 208 includes a loading portion 210, an unloading portion 212, and a first peak load 214 at 0.20 mm extension. The second loading cycle 216 includes a loading portion 218, an unloading portion 220, and a second peak load 222 at 0.20 mm extension. The third loading cycle 224 includes a loading portion 226, an unloading portion 228, and a third peak load 230 at 0.20 mm extension. The fourth loading cycle 232 includes a loading portion 234, an unloading portion 236, and a fourth peak load 238 at 0.20 mm extension. The peak loads 214, 222, 230, 238 may be referred to as cold working loads. The peak loads 222, 230, 238 are close to the same value, indicating that minimal cold work strain hardening occurred during the third loading cycle 224 and the fourth loading cycle 232. Along the unloading portion 236, point 240 corresponds to an installation load of 2600 N, point 242 corresponds to a 1500 N load, point 244 corresponds to a 1000 N load, and point 246 corresponds to a diminution of 0.075 mm from the installed load 240.

Figure 13:
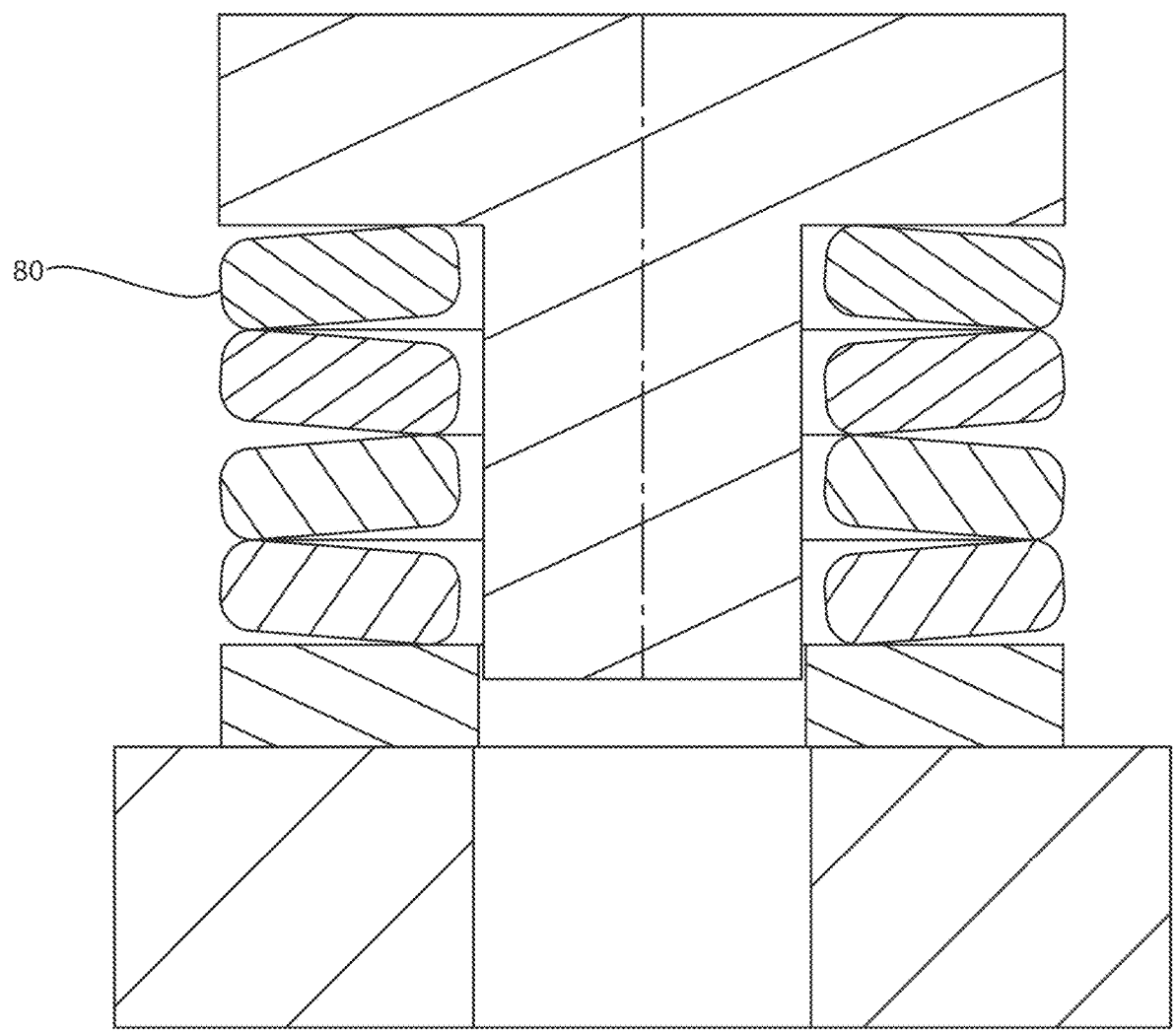
FIG. 13 is a diagram of a finite element analysis model of a series stack of four 8×3.4×0.82 spring washers under zero deflection.

FIG. 13 is a diagram of a finite element analysis model of a series stack of four 8×3.4×0.82 spring washers 80 under zero deflection.

Figure 14A:
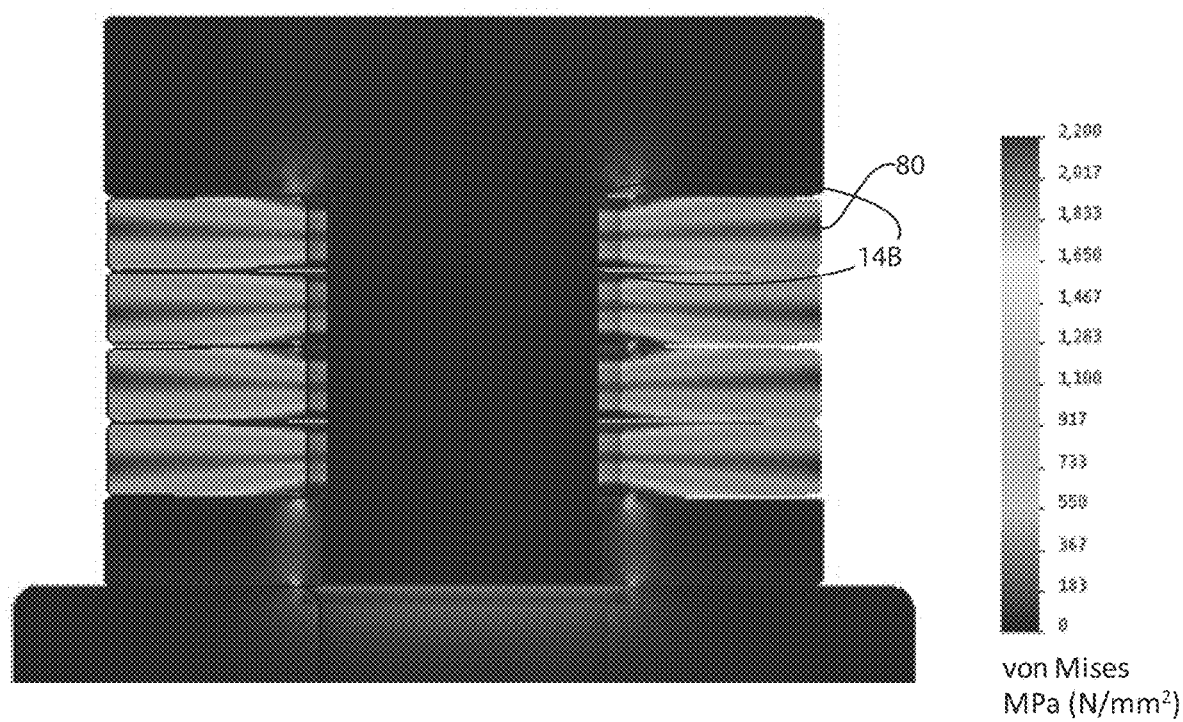
FIG. 14A is a finite element analysis contour plot of von Mises stress in the spring washer stack of FIG. 13.
Figure 14B:
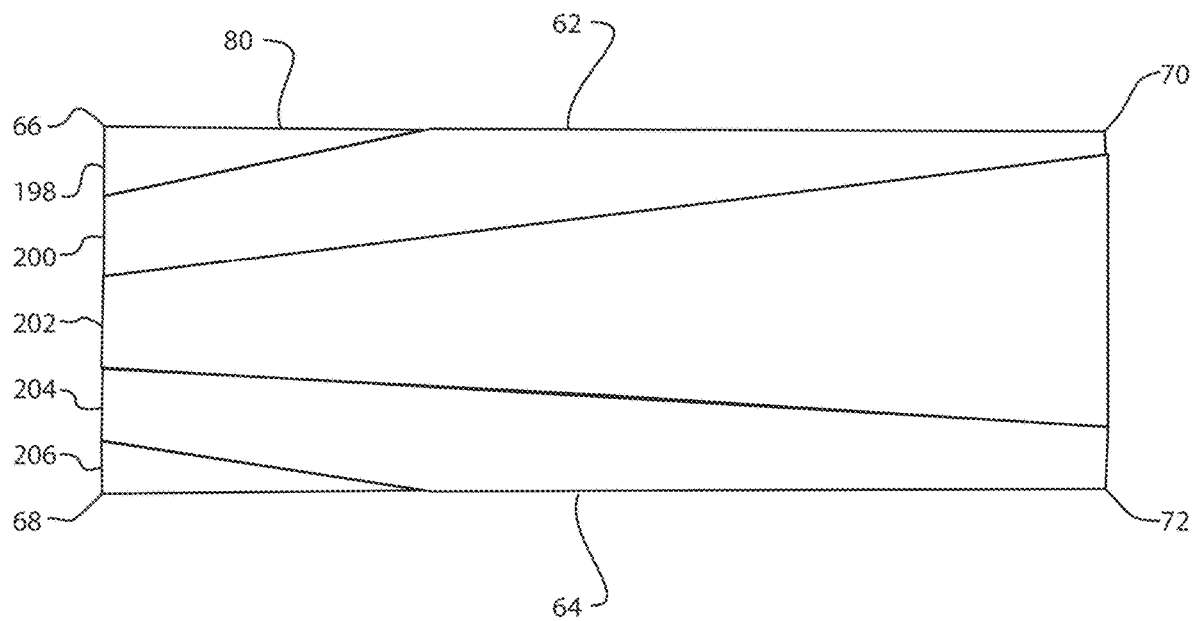
FIG. 14B is an enlarged detail view of one side of one of the spring washers of FIG. 14A.

FIG. 14A is a finite element analysis contour plot of von Mises stress in the stack of spring washers 80. FIG. 14B is an enlarged detail view of one side of one of the spring washers 80, with isostress contour lines that divide the cross-sectional area of the spring washer 80 into a high compressive stress zone 198, a moderate compressive stress zone 200, a neutral stress zone 202, a moderate tensile stress zone 204, and a high tensile stress zone 206. Note the appearance of the high tensile stress zone 206, which was absent in spring washer 74 in FIGS. 7A and 7B. The high compressive stress zone 198 and the moderate compressive stress zone 200 together may be referred to as a compression plate extending across the upper surface 62 (FIG. 2C) between the inner upper edge 66 and the outer upper edge 70. The high tensile stress zone 206 and the moderate tensile stress zone 204 together may be referred to as a tension plate extending across the lower surface 64 between the inner lower edge 68 and the outer lower edge 72. FIGS. 14A and 14B reveal peculiar and unexpected full-face compression and tension plates which produce a load resisting couple causing the spring action. The inventors' design allowance for local yielding has expanded the size (extending across the washer face, and into the washer thickness) and eccentricity (vertical separation by increased washer thickness) of the compression and tension plates versus the stress distribution shown in FIGS. 7A and 7B.

FIG. 19 is a data sheet for an 8×3.4×1.1 spring washer 82, with overall height H=1.211 mm and inner height h=0.111 mm. Note that the data sheet states that the stresses are too high for standard fatigue conditions. Therefore, the spring washer 82 falls outside customary design parameters for spring washers.

FIG. 20 is a data sheet for another 8×3.4×1.1 spring washer 84, with overall height H=1.232 mm and inner height h=0.132 mm. Note that the data sheet states that the stresses are too high for standard fatigue conditions. Therefore, the spring washer 84 falls outside customary design parameters for spring washers.

Figure 21A:
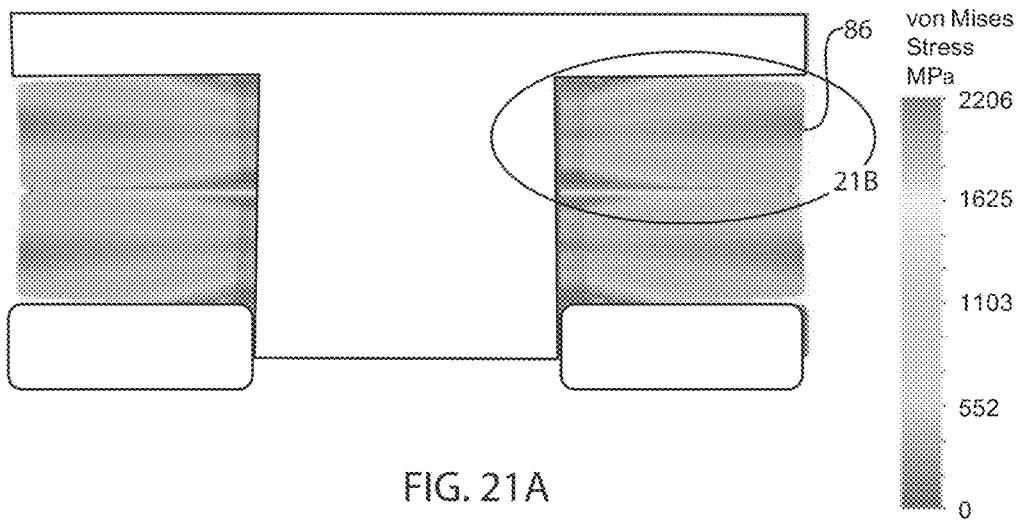
FIG. 21A is a finite element analysis contour plot of von Mises stress in a series stack of two spring washers of FIG. 16A.
Figure 21B:
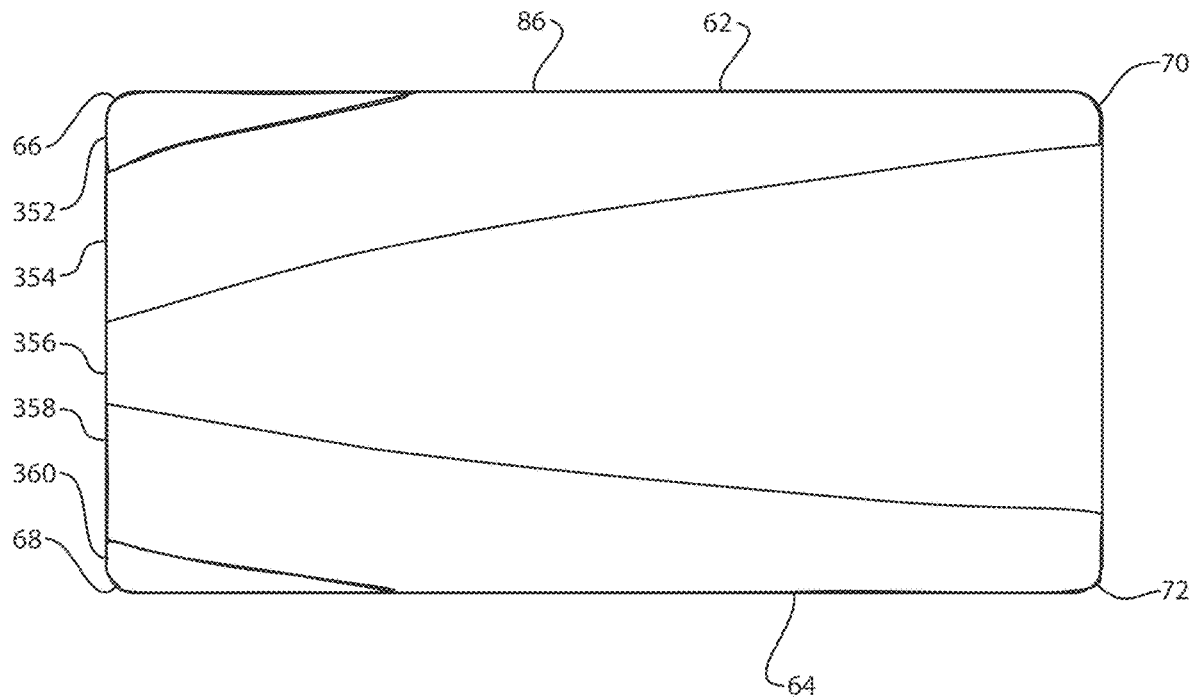
FIG. 21B is an enlarged detail view of one side of one of the spring washers of FIG. 21A.

FIG. 21A is a finite element analysis contour plot of von Mises stress in a series stack of two 8×3.4×1.1 spring washers 86, with overall height H=1.295 mm and inner height h=0.20 mm. FIG. 21B is an enlarged detail view of one side of one of the spring washers 86, with isostress contour lines that divide the cross-sectional area of the spring washer 86 into a high compressive stress zone 352, a moderate compressive stress zone 354, a neutral stress zone 356, a moderate tensile stress zone 358, and a high tensile stress zone 360. FIGS. 21A and 21B reveal peculiar and unexpected full-face compression and tension plates which produce a load resisting couple causing the spring action. The high compressive stress zone 352 and the moderate compressive stress zone 354 together may be referred to as a compression plate extending across the upper surface 62 (FIG. 2C) between the inner upper edge 66 and the outer upper edge 70. The high tensile stress zone 360 and the moderate tensile stress zone 358 together may be referred to as a tension plate extending across the lower surface 64 between the inner lower edge 68 and the outer lower edge 72. Furthermore, FIGS. 21A and 21B show an increased eccentricity (vertical separation because the plate is far thicker than washers using current art) between both compression and tension couples, further increasing load capacity. That this phenomenon could occur within a single thick spring washer rather than by requiring a stack of spring washers with a much larger total stack height was not usual or customary design practice in the spring washer design industry.

FIGS. 22A-D provide a comparison of the von Mises stress distributions in the spring washer 74 of FIGS. 7A and 7B and the stack of spring washers 86 of FIGS. 21A and 21B. The high compressive stress zone 88 of spring washer 74 and the high compressive stress zone 352 of spring washer 86 both involve the inner upper edge 66 (FIG. 2C). The moderate compressive stress zone 90 extends across a middle portion of the upper surface 62, while the moderate compressive stress zone 354 extends across the middle portion of the upper surface 62 and involves the outer upper edge 70. The high compressive stress zone 88 and the moderate compressive stress zone 90 together form a compression ring that extends partially across the upper surface 62 from the inner upper edge 66. The high compressive stress zone 352 and the moderate compressive stress zone 354 together form a compression plate that extends entirely across the upper surface 62 between the inner upper edge 66 and the outer upper edge 70. The neutral stress zone 92 extends across an outboard portion of the upper surface 62 and involves the outer upper edge 70; this zone slants from the outer upper edge 70 toward the inner lower edge 68 and involves 54% of the cross-sectional area of the spring washer 74. Thus 46% of the cross-sectional area of the spring washer 74 is stressed. The neutral stress zone 356 does not involve the upper surface 62 or the lower surface 64; this zone is evenly spaced between the inner upper edge 66 and the inner lower edge 68 and involves 41% of the cross-sectional area of the spring washer 86. Thus 59% of the cross-sectional area of the spring washer 86 is stressed. Since a greater percentage of the cross-sectional area of the spring washer 86 is stressed compared to the spring washer 74, the spring washer 86 is a more efficient design. The high tensile stress zone 96 and the moderate tensile stress zone 94 together form a tension plate that extends across the lower surface 64 between the inner lower edge 68 and the outer lower edge 72. The high tensile stress zone 360 and the moderate tensile stress zone 358 together form a tension plate extending across the lower surface 64 between the inner lower edge 68 and the outer lower edge 72. The compression and tension plates also contribute to the profound increase in load versus extension capacity proven to exist by the mechanical testing shown.

Figure 23A:
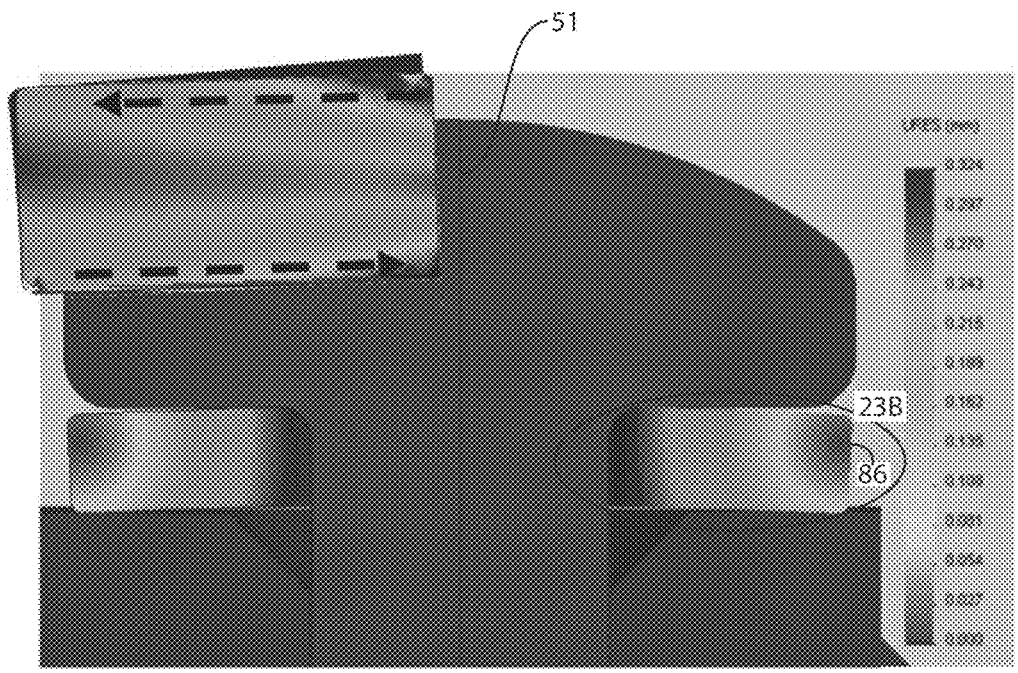
FIG. 23A is a finite element analysis contour plot of omni-directional movement in a single spring washer of FIG. 16A.
Figure 23B:
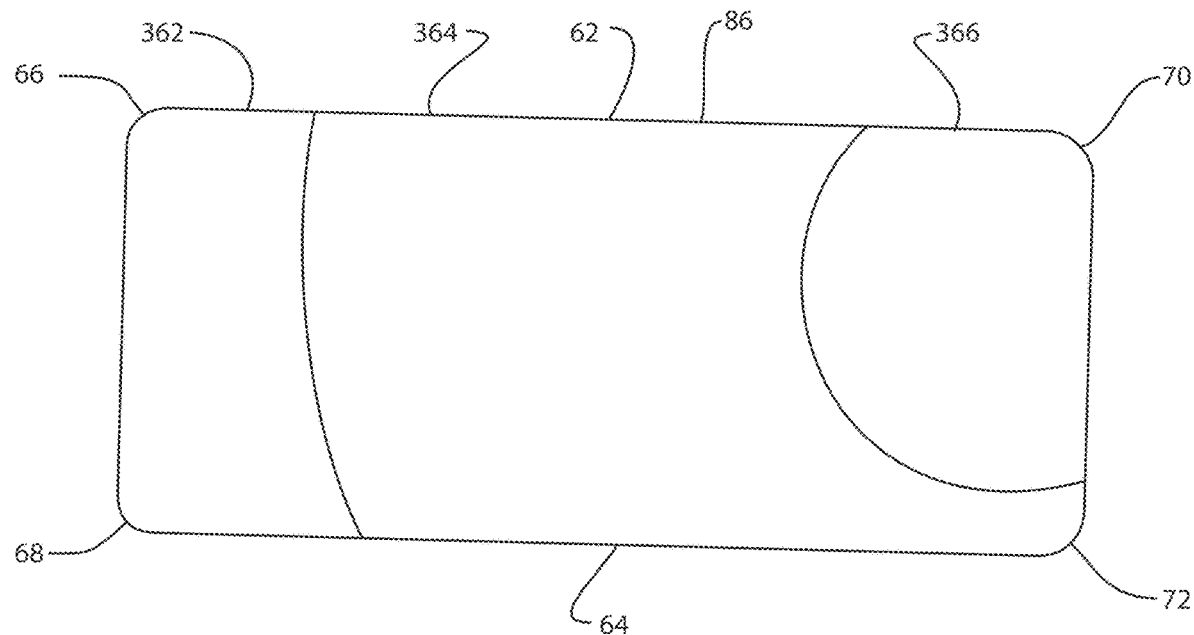
FIG. 23B is an enlarged detail view of one side of the spring washer of FIG. 23A.

FIG. 23A is a finite element analysis contour plot of omni-directional movement in a single spring washer 86. FIG. 23B is an enlarged detail view of one side of one of the spring washer 86, with iso-displacement contour lines that divide the cross-sectional area of the spring washer into a high displacement zone 362, a moderate displacement zone 364, and a neutral displacement zone 366.

Figure 24A:
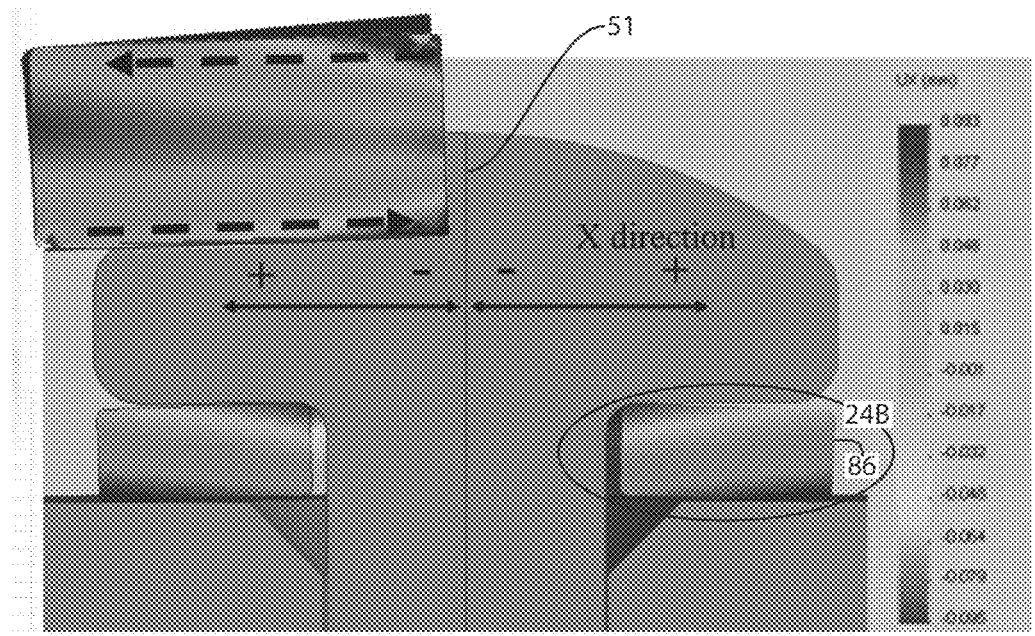
FIG. 24A is a finite element analysis contour plot of x-direction movement in the spring washer of FIG. 23A.
Figure 24B:
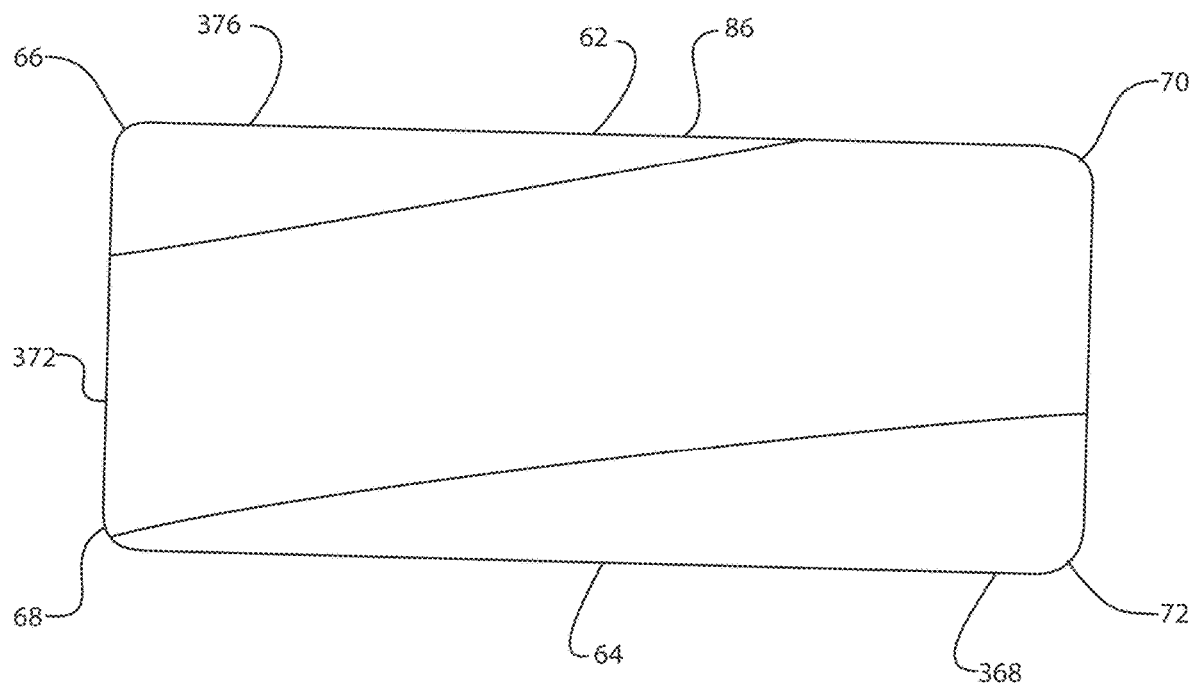
FIG. 24B is an enlarged detail view of one side of the spring washer of FIG. 24A.

FIG. 24A is a finite element analysis contour plot of x-direction movement in the spring washer 86 of FIG. 23. X-direction movement in this figure is perpendicular to a centerline, or central axis of revolution 51, of the spring washer 86. FIG. 24B is an enlarged detail view of one side of one of the spring washer 86, with iso-displacement contour lines that divide the cross-sectional area of the spring washer into a high positive x-displacement zone 368, a neutral x-displacement zone 372, and a high negative x-displacement zone 376. Note that when the spring washer 86 is compressed, the top compression plate (for example FIG. 21B, the high compressive stress zone 352 and the moderate compressive stress zone 354 together) moves toward the centerline while the bottom tension plate (for example FIG. 21B, the high tensile stress zone 360 and the moderate tensile stress zone 358 together) moves away from the centerline. This relatively large couple is connected by shear through the middle of the spring washer thickness (t). The material in the shear couple, trying to return to its original shape, gives the spring washer 86 its spring action. The shear couple is connected through the center shear plate, a low stress region compared to the top compression plate or the bottom tension plate (for example FIG. 21B, the neutral stress zone 356).

Figure 17:
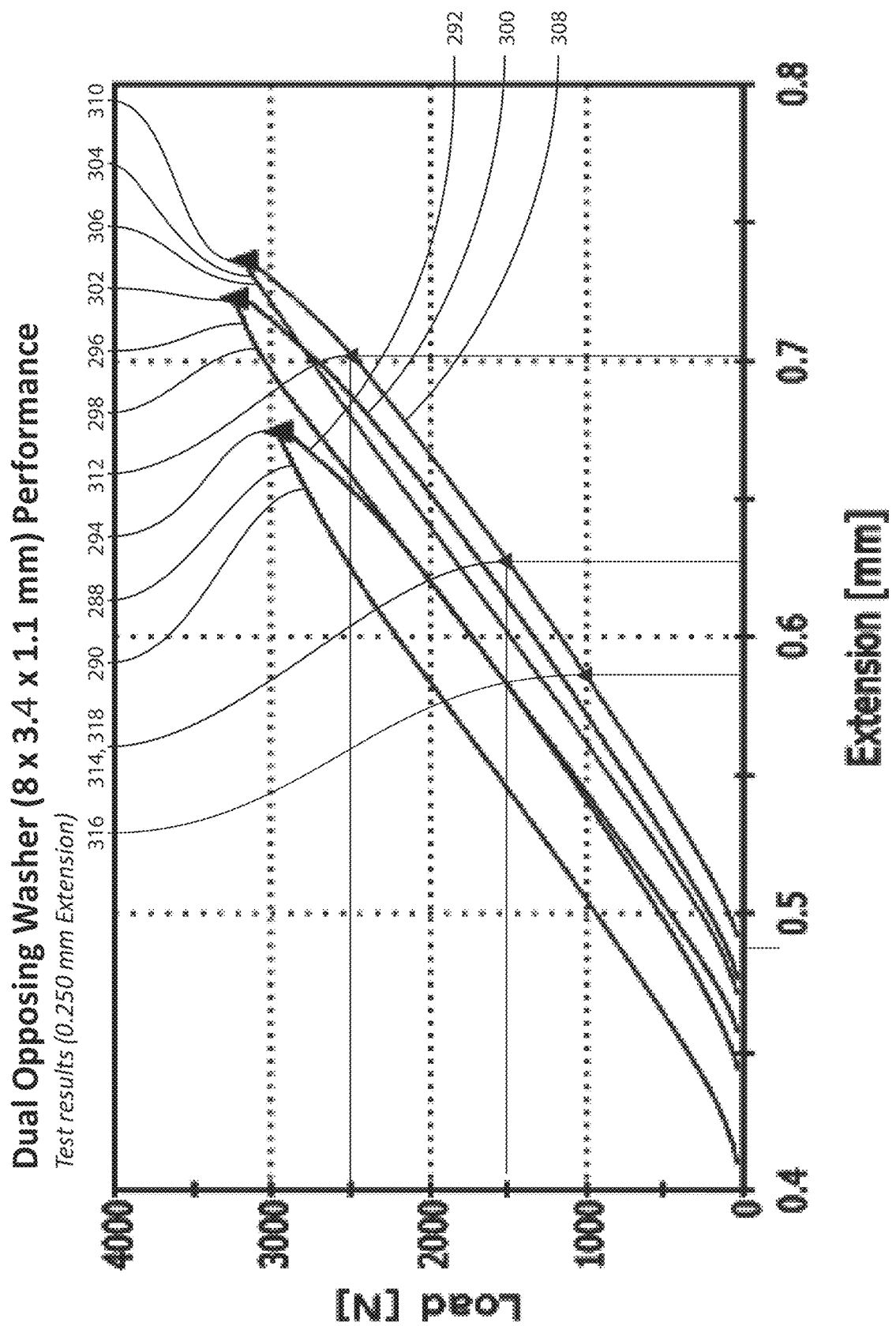
FIG. 17 is a chart of load versus extension for three consecutive loading cycles of a series stack of two spring washers of FIG. 16A to 0.25 mm extension.

FIG. 17 is a chart of load versus extension for three consecutive loading cycles of a series stack of two spring washers 86 to 0.25 mm extension. The first loading cycle 288 includes a loading portion 290, an unloading portion 292, and a first peak load 294 at 0.25 mm extension. The second loading cycle 296 includes a loading portion 298, an unloading portion 300, and a second peak load 302 at 0.25 mm extension. The third loading cycle 304 includes a loading portion 306, an unloading portion 308, and a third peak load 310 at 0.25 mm extension. The peak loads 294, 302, 310 may be referred to as cold working loads. The peak loads 302, 310 are close to the same value, indicating that minimal cold work strain hardening occurred during the third loading cycle 304. Along the unloading portion 308, point 312 corresponds to an installation load of 2500 N, point 314 corresponds to a 1500 N load, point 316 corresponds to a 1000 N load, and point 318 corresponds to a diminution of 0.075 mm from the installed load 240. In this example, points 314 and 318 are identical. The series stack of two spring washers 86 provides 1500 N after 0.075 mm of diminution with a stack height of 2.3 mm. Note that an installation load of 3000 N is also feasible with this spring washer 86.

Figure 18A:
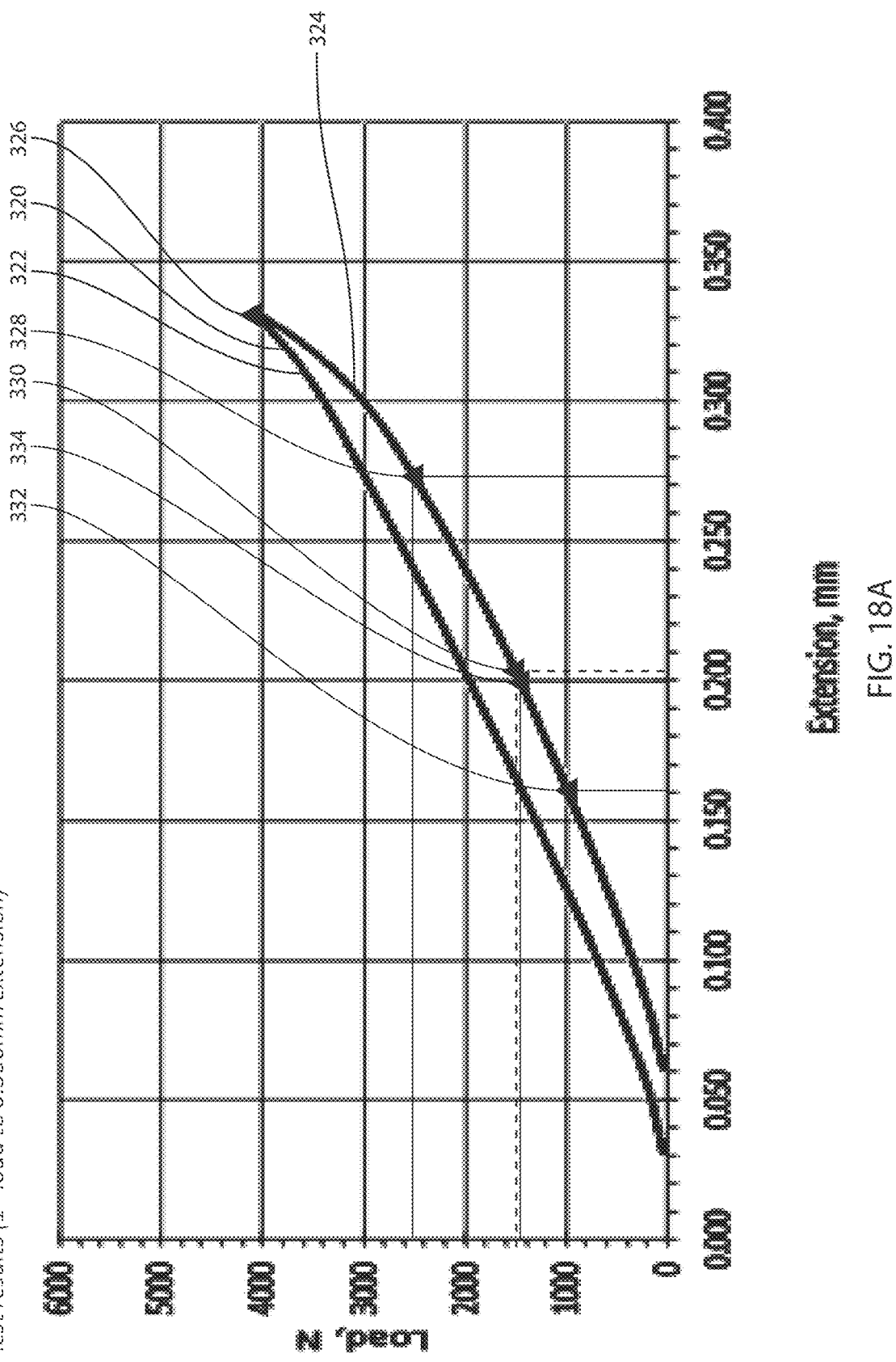
FIG. 18A is a chart of load versus extension for a single loading cycle of the spring washer stack of FIGS. 17 to 0.30 mm extension.

FIG. 18A is a chart of load versus extension for a single loading cycle of the series stack of two spring washers 86 to 0.30 mm extension. The loading cycle 320 includes a loading portion 322, an unloading portion 324, and a peak load 326 at 0.30 mm extension. Along the unloading portion 324, point 328 corresponds to an installation load of 2500 N, point 330 corresponds to a 1500 N load, point 332 corresponds to a 1000 N load, and point 334 corresponds to a diminution of 0.075 mm from the installed load 328. Note that an installation load of 3000 N is also feasible with this stack.

Figure 18B:
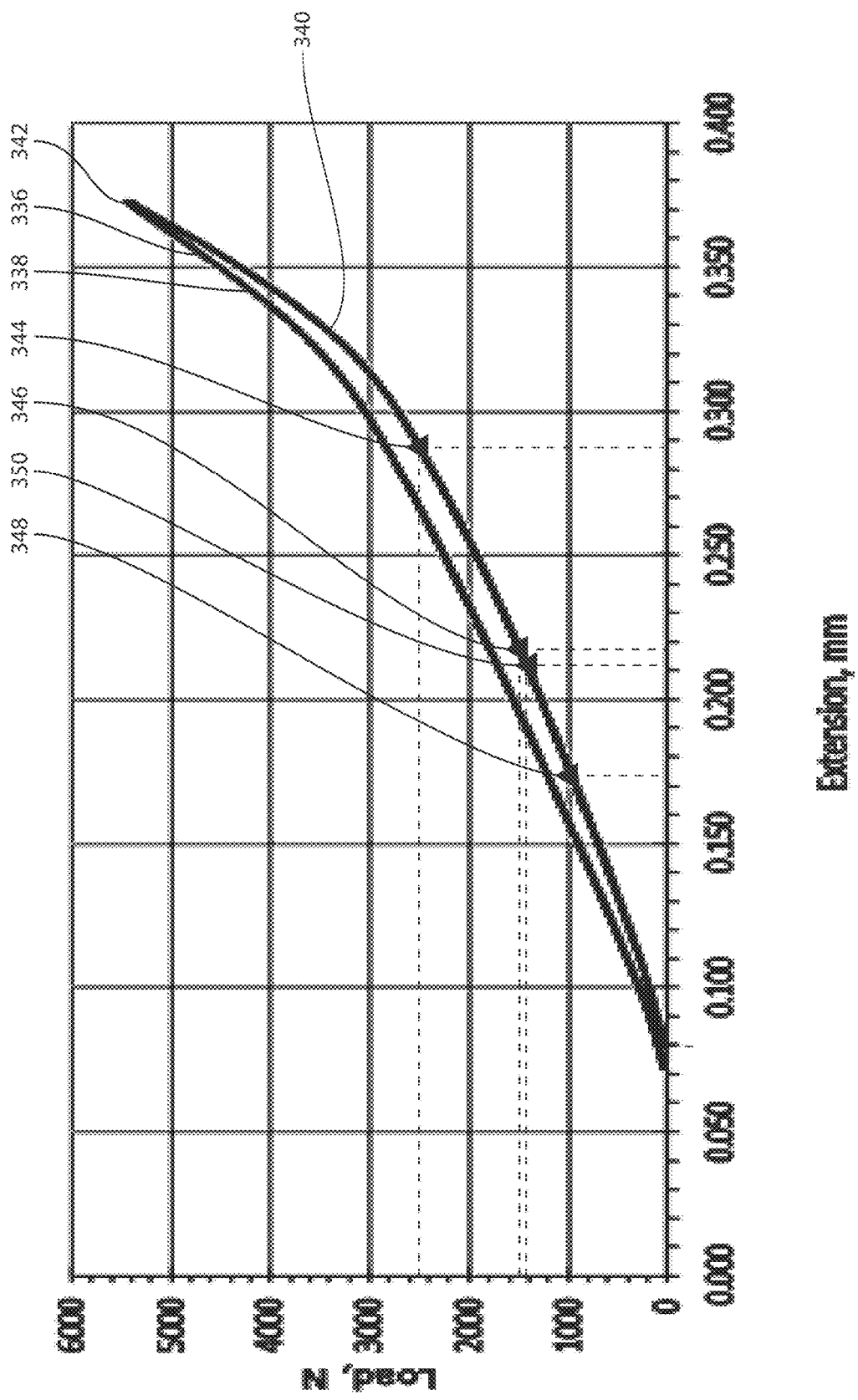
FIG. 18B is a chart of load versus extension for a third loading cycle of the stack of spring washers of FIG. 18A to 0.30 mm extension.

FIG. 18B is a chart of load versus extension for a third loading cycle of the series stack of two spring washers 86 to 0.30 mm extension. The loading cycle 336 includes a loading portion 338, an unloading portion 340, and a peak load 342 at 0.30 mm extension. Along the unloading portion 340, point 344 corresponds to an installation load of 2500 N, point 346 corresponds to a 1500 N load, point 348 corresponds to a 1000 N load, and point 350 corresponds to a diminution of 0.075 mm from the installed load 328. Note that an installation load of 3000 N is also feasible with this stack.

Figure 16A:
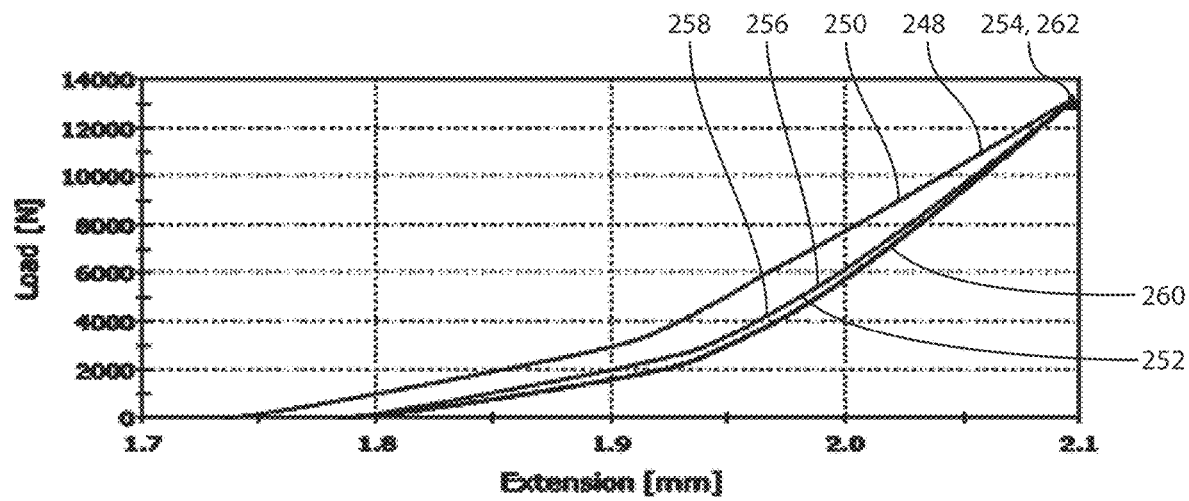
FIG. 16A is a chart of load versus extension for two consecutive loading cycles of a single 8×3.4×1.1 spring washer, with overall height H=1.295 mm and inner height h=0.20 mm to 13,000 N.

FIG. 16A is a chart of load versus extension for two consecutive loading cycles of a single spring washer 86 to 13,000 N (spring washer is flat at 3,500 N). The first loading cycle 248 includes a loading portion 250, an unloading portion 252, and a first peak load 254 at 13,000 N. The second loading cycle 256 includes a loading portion 258, an unloading portion 260, and a second peak load 262 at 13,000 N. This was to test the spring washer function under potential intermittent loads just beyond the ultimate strength point 24 of the bone (FIG. 1). Normal spring washer performance resumed after the 13,000 N load was removed.

Figure 16B:
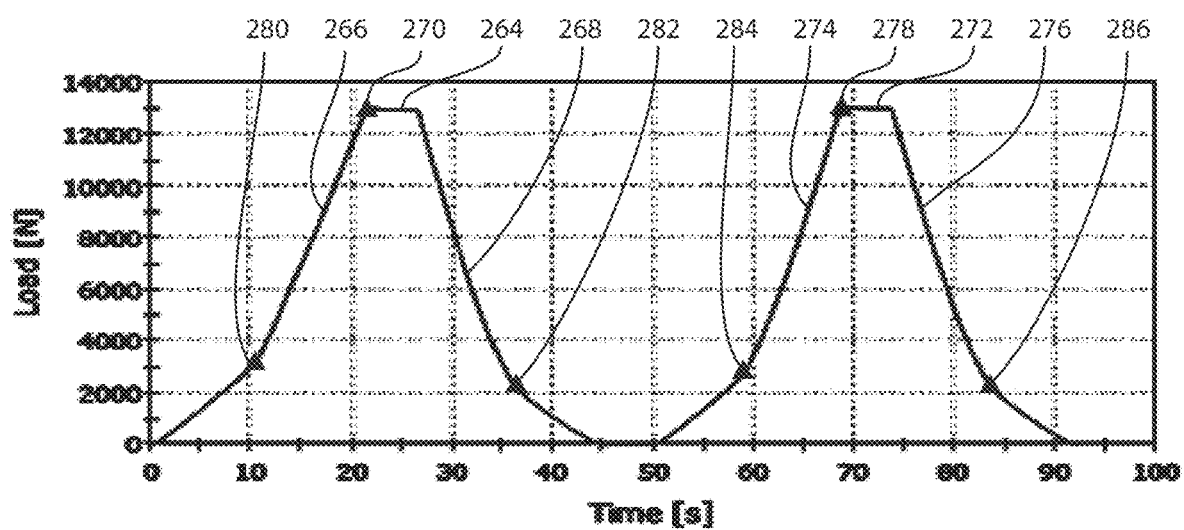
FIG. 16B is a chart of load versus time for the spring washer of FIG. 16A to 13,000 N.

FIG. 16B is a chart of load versus time corresponding to the data in FIG. 16A. In FIG. 16B, the first loading cycle 264 includes a loading portion 266, an unloading portion 268, and a first peak load 270 at 13,000 N. The second loading cycle 272 includes a loading portion 274, an unloading portion 276, and a second peak load 278 at 13,000 N. The peak loads 270, 278 are identical at 13,000 N. The spring becomes completely flat at point 280 along the loading portion 266 where the slope changes, and resumes function as a spring at point 282 along the unloading portion 268 where the slope changes. Between points 280 and 282, the slope of the curve is due to the inherent material elasticity of the flattened washer; the zero-slope portion reflects a pre-set load limit of 13,000 N in the testing program. The spring washer 86 again becomes completely flat at point 284 along the loading portion 274, and again resumes function as a spring at point 286 along the unloading portion 276. FIGS. 16A and 16B demonstrate that the spring washer 86 survives multiple high load conditions and continues to perform as before after the high load is removed.

FIG. 26 is a table summarizing data for spring washers 74, 76, 78, and 86 from FIGS. 9, 11, 12A, 12B, 15, 17, 18A, and 18B for installation loads of 1500 N to 2800 N; and corresponding loads 144, 158, 188, 196, 246, 318, 334, 350 for 0.075 mm diminution from the corresponding installed load. However, the data reported for the series stack of four spring washers 78 is an estimate. The table includes selected data in parentheses, which includes the corresponding relaxation of a 3.2 mm diameter×21 mm long screw, which also helps to accommodate diminution.

The effective capacity for installation load is greater than or equal to 1500 N for all spring washer sizes and configurations except for the single spring washer 74. The effective installation load is greater than or equal to 2000 N for all spring washer sizes and configurations except for the single spring washer 74 and the single spring washer 76. The effective installation load is greater than or equal to 2500 N for all configurations of spring washer 78 and spring washer 86, including a single spring washer 78.

The load after 0.075 mm diminution from the corresponding installed load is greater than or equal to 1000 N for all spring washer sizes and configurations except for the single spring washer 74 and the single spring washer 76. The load after 0.075 mm diminution from the corresponding installed load is greater than or equal to 1100 N for all configurations of spring washer 76, spring washer 78, and spring washer 86, except for the single spring washer 76. The load after 0.075 mm diminution from the corresponding installed load is greater than or equal to 1300 N for the series stack of four spring washers 76 after a single loading cycle to 0.60 mm (FIG. 12A), as well as for all series stack configurations of spring washer 78 and spring washer 86.

The diminution from the corresponding installed load to a 1500 N load is greater than or equal to 0.040 mm for all spring washer sizes and configurations except for the single spring washer 76 and the series stack of four spring washers 76 after three loading cycles to 0.60 mm (FIG. 12B). The diminution from the corresponding installed load to a 1500 N load is greater than or equal to 0.050 mm for the series stack of four spring washers 76 after a single loading cycle to 0.60 mm (FIG. 12A), as well as for all configurations of spring washer 78 and spring washer 86. The diminution from the corresponding installed load to a 1500 N load is greater than or equal to 0.069 mm for all series stack configurations of spring washer 78 and spring washer 86.

The diminution from the corresponding installed load to a 1000 N load is greater than or equal to 0.088 mm for all spring washer sizes and configurations except for the single spring washer 76. The diminution from the corresponding installed load to a 1000 N load is greater than or equal to 0.112 mm for all series stack configurations of spring washer 76, spring washer 78, and spring washer 86.

The last row of the table presents the percent difference in the 1000 N diminution versus the parallel stack of seven spring washers 74 (taken as the base case). The series stack configurations of spring washer 76, spring washer 78, and spring washer 86 provide 27% to 82% increase in the 1000 N diminution versus the parallel stack of seven spring washers 74, with an estimated 127% increase for the series stack of four spring washers 78. These percentages reflect improvement over the current art.

FIG. 25A is another cross sectional view of the spring washer 50. The inner upper edge 66 is now also labeled as location I, the inner lower edge 68 is now also labeled as location II, and the outer lower edge 72 is now also labeled as location III. FIG. 25B is a table listing dimensions, travel, load, and stresses for various spring washers. The stress $\sigma_I$ corresponds to the stress at location I of FIG. 25A. The stress $\sigma_{II}$ corresponds to the stress at location II. The stress $\sigma_{III}$ corresponds to the stress at location III. UTS stands for ultimate tensile strength. YS stands for yield strength. Six sizes of Mubea standard 8 mm spring washers are listed first, followed by spring washers 74, 80, and 86 according to the present disclosure. Note that stresses at locations I, II and III, forces and travel are as determined by Mubea standard formulae. Many stresses in these advanced spring washers 74, 80, 86 (as calculated by Mubea current art) are significantly above yield, and even ultimate strength. This is the intent of the disclosed ultimate strength design. Because the installed washers will see about a 40% to 60% reduction in installed stress within a few hours to a few days, fatigue conditions are not expected to exist shortly after installation. Also, large areas of the compression and tension plates can be allowed to yield, and thereby enable very high installed loads relative to washer size.

Figure 27A:
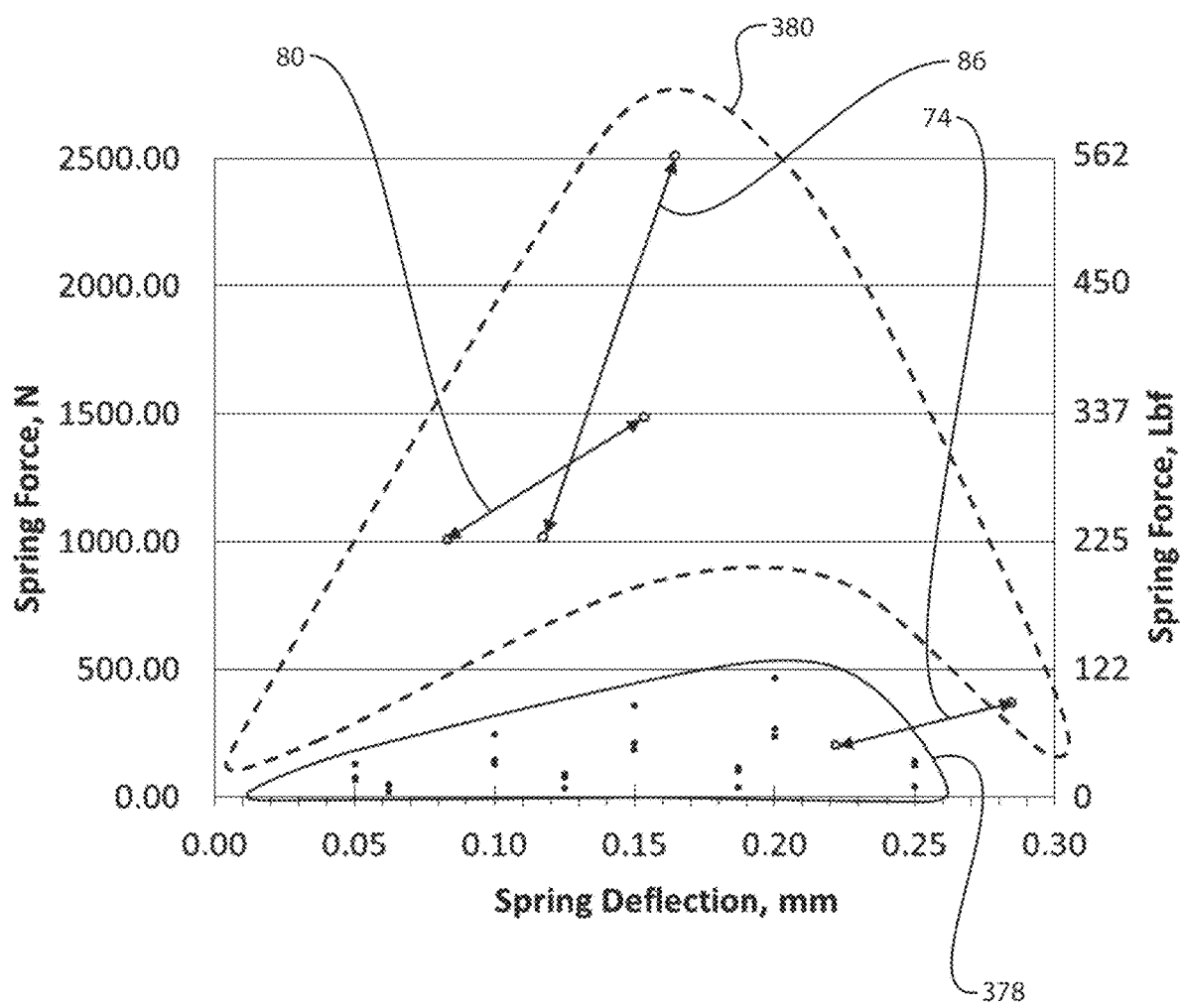
FIG. 27A is a chart of load versus deflection for various spring washers.
Figure 27C:
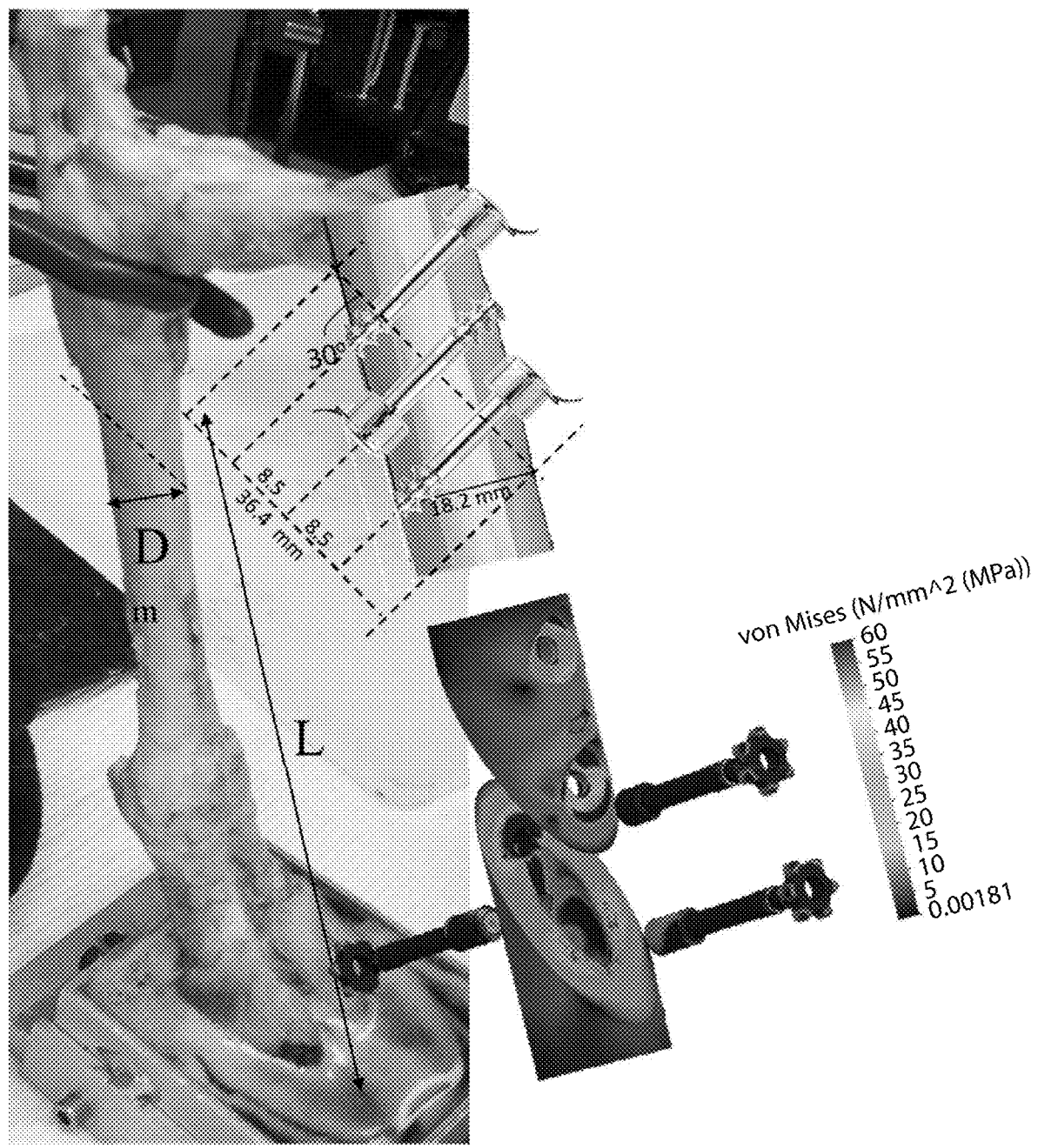
FIG. 27C is a diagram showing a 30° osteotomy in a long bone, stabilized with three bone screw assemblies; a finite element analysis contour plot of von Mises stress in the osteotomy, bone, and bone screw assemblies; and a fixtured long bone of a sheep.

FIG. 27A is a chart summarizing force versus deflection data for spring washers 74, 80, 86 as presented in FIG. 25. The chart includes a first area 378 that includes multiple data points for Mubea standard 8 mm spring washers. The first area 378 may be referred to as an industry standard design zone. In the first area 378, spring deflections are between 0.05 mm and 0.25 mm; the corresponding spring forces per spring do not exceed 500 N. The chart includes a second area 380 that includes multiple data points for 8 mm spring washers designed according to the principles set forth herein. The second area 380 may be referred to as the inventors' design zone. In the second area 380, spring deflections are between 0.05 mm and 0.29 mm; the corresponding spring forces per spring are between 450 N and 2900 N. For spring washers 80, 86, the spring forces are two to five times higher than the industry standard for a given deflection. Following the lower edge of the second area 380, the second area also encompasses spring forces of at least 290 N for 0.05 mm deflection, at least 355 N for 0.062 mm deflection, at least 573 N for 0.10 mm deflection, at least 709 N for 0.125 mm deflection, at least 820 N for 0.150 mm deflection, at least 895 N for 0.187 mm deflection, at least 895 N for 0.200 mm deflection, and at least 637 N for 0.250 mm deflection.

FIG. 27B is a table of various total diminution values and compression forces calculated from incremental diminution values for the spring washer, bone, and screw. Referring to the third row from the bottom, starting from an installed load of 3000 N, bone screw assembly 430 described below can accommodate 0.114 mm of total diminution and still provide 1837 N per screw when installed across the example discontinuity shown in FIG. 27C. Spring extension accommodates 0.081 mm of diminution, while the bone extension (rebound from installed compression) accommodates 0.019 mm and the screw contraction accommodates 0.014 mm. While optimized for 114 μm diminution, bone screw assembly 430 can accommodate as much as 0.250 mm total diminution and still provide 449 N per screw, referring to the bottom row. Spring washers are necessary to close 0.250 mm of diminution. Without spring washers, diminution would quickly exhaust the total of 0.041 mm and 0.031 mm of capacity for closure from the screw and bone alone. Without spring washers of the current embodiment, diminution closure will cease and the system will sustain little internal or external forces.

FIG. 27C is a diagram showing a 30° osteotomy in a long bone, stabilized with three bone screw assemblies; a finite element analysis contour plot of von Mises stress in the osteotomy, bone, and bone screw assemblies; and a fixtured long bone of a sheep.

Turning now to FIGS. 29A-35D, medical devices that incorporate the spring washers will now be disclosed.

Referring to FIGS. 29A-29D, a bone screw assembly 400 includes a screw 402, a base 404, and a spring washer 50.

The screw 402 includes a proximal portion 406, a distal portion 408, and a shaft or shank 410 between the proximal portion 406 and the distal portion 408. The proximal portion 406 includes a head 412 with a torque drive feature 414. The torque drive feature 414 may be a protruding feature, such as a hex key, or a recessed feature, such as a hex socket. A hexalobular socket is shown. The head 412 may be integrally formed with the shank 410, or the head 412 may be coupled to the shank 410 by an interconnection such as threads, cross pins, press fit, weld, peening, and the like. The head 412 includes a surface 415 that faces toward the distal portion 408. The surface 415 may be concave, convex, or flat or planar. The distal portion 408 includes external threads 416. The external threads 416 may be specifically designed to engage cortical or cancellous bone. The screw 402 may have a blunt, non-cutting distal tip 418. The screw 402 may be inserted into a tapped bone hole. Traditional bone screws tend to include very sharp tips, such as trocar tips, self-tapping tips, and the like. While these designs may eliminate a separate tapping step, bone screws are frequently installed with the tip protruding two or three threads beyond the contralateral cortex to obtain good engagement between the screw threads and the cortex. A protruding sharp screw tip may cause ongoing irritation and pain as surrounding soft tissues move relative to the screw tip. The shank 410 may be smooth. The shank 410 has a smaller outer diameter than the head 412 or the major diameter of the external threads 416. The outer diameter of the shank 410 may be the same as the minor diameter of the external threads 416, or nearly the same.

Figure 29A:
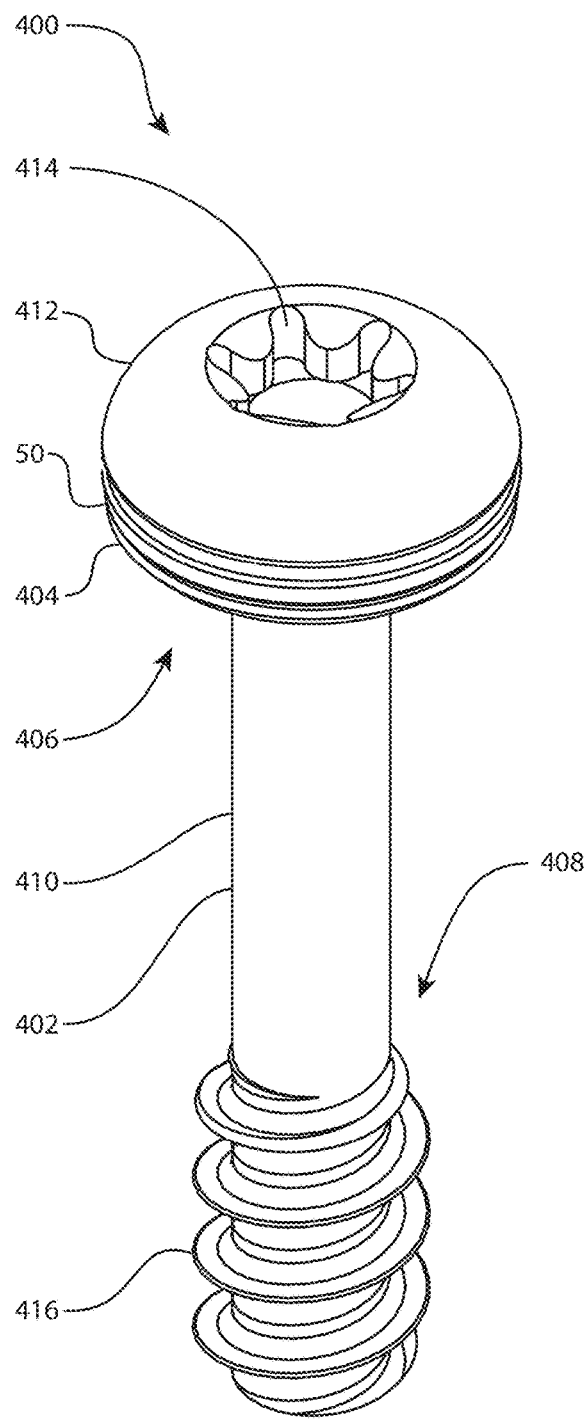
FIG. 29A is an isometric view of a bone screw assembly.
Figure 29B:
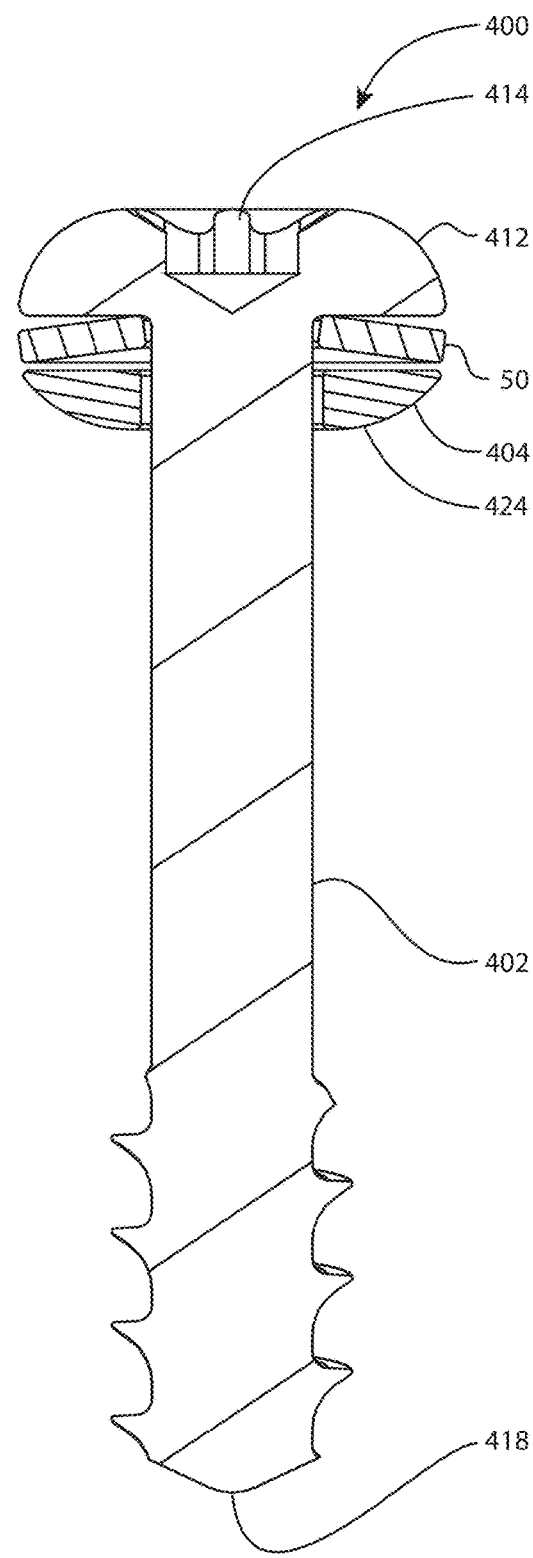
FIG. 29B is a cross sectional view of the bone screw assembly of FIG. 29A.

The base 404 may be disc shaped with a central aperture 420 sized to receive the shank 410 so that the base 404 is free to slide along the shank 410. The base 404 has a larger outer diameter than the shank 410, and may have a larger outer diameter than the head 412 or the major diameter of the external threads 416. However, the outer diameter of the base 404 may be the same as the outer diameter of the head 412 or the major diameter of the external threads 416, or nearly the same. The base 404 includes a first surface 422 and a second surface 424 opposite the first surface. The aperture 420 pierces the first and second surfaces 422, 424. The first and second surfaces 422, 424 may be concave, convex, or flat or planar. In FIGS. 29B and 29C, the first surface 422 is flat or planar, while in FIGS. 29B and 29D, the second surface 424 is convex.

The spring washer 50 may be spring washer 74, 76, 78, 80, 82, 84, 86, or another size consistent with the principles set forth herein. Referring to FIGS. 2C and 29B, the outer diameter (D) 52 may be the same as the outer diameter of the head 412 or the outer diameter of the base 404, or nearly the same. The outer diameter (D) 52 may be less than or equal to the outer diameter of the head 412 or the outer diameter of the base 404 so that the outer lower edge 72 may rest on the surface 415 of the head 412 or the first surface 422 of the base 404. The inner diameter (d) 54 receives the shank 410 of the screw 402 so that the spring washer 50 is free to slide along the shank 410. The inner diameter (d) 54 may be the same size as the aperture 420.

When the bone screw assembly 400 is operatively assembled, the shank 410 of the screw 402 is received in the inner diameter (d) 54 of the spring washer 50 and the aperture 420 of the base 404. The spring washer 50 is between the head 412 of the screw 402 and the base 404. The first surface 422 of the base 404 may face toward the surface 415 of the head 412 of the screw 402 and the second surface 424 of the base 404 may face toward the distal portion 408 of the screw 402. However, the orientation of the first and second surfaces 422, 424 may be reversed. The upper surface 62 of the spring washer 50 may face toward the surface 415 and the lower surface 64 of the spring washer 50 may face toward the first surface 422. However, the orientation of the upper and lower surfaces 62, 64 may be reversed.

In examples where the head 412 is integral with the screw 402, the bone screw assembly 400 may be assembled by first passing the spring washer 50 and then the base 404 along the external threads 416 from the blunt tip 418 toward the head 412. In this arrangement, the inner diameter (d) 54 and the aperture 420 may be equal to or greater than the minor diameter of the external threads 416 plus one-half of the difference between the major diameter of the external threads and the minor diameter of the external threads. Preferably, the inner diameter (d) 54 and the aperture 420 are optimized to the smallest size that does not damage the inner diameter (d) 54, the aperture 420, or the external threads 416 during assembly.

In examples where the head 412 is coupled to the screw 402 by an interconnection, the bone screw assembly 400 may be assembled by first passing the base 404 and then the spring washer 50 along the shank 410 from the proximal portion 406 toward the distal portion 408. In this arrangement, the inner diameter (d) 54 and the aperture 420 may be equal to or greater than the outer diameters of the interconnection and the shank 410. Preferably, the inner diameter (d) 54 and the aperture 420 are optimized to the smallest size that does not damage the inner diameter (d) 54, the aperture 420, the interconnection, or the shank 410 during assembly, and that permits the base 404 and the spring washer 50 to slide freely along the shank 410 in use.

When bone screw assembly 400 is installed across a bony discontinuity with an installation load of 3000 N, the bone screw assembly 400 dynamically adjusts to provide a 2000 N load at 0.078 mm (78µ) of diminution. The 3000 N installation load causes an average of 30 MPa of bone stress in the discontinuity zone or fracture zone. The 2000 N post-diminution load causes an average of 18 MPa to 20 MPa of bone stress in the discontinuity zone or fracture zone.

Referring to FIGS. 30A-30D, a bone screw assembly 430 includes a screw 432, a base 434, and a series stack of two spring washers 50 in facing relationship.

The screw 432 includes a proximal portion 436, a distal portion 438, and a shaft or shank 440 between the proximal portion 436 and the distal portion 438. The proximal portion 436 includes a head 442 with a torque drive feature 444. The torque drive feature 444 may be a protruding feature, such as a hex key, or a recessed feature, such as a hex socket. A hexalobular key is shown. The head 442 may be integrally formed with the shank 440, or the head 442 may be coupled to the shank 440 by an interconnection such as threads, cross pins, press fit, weld, peening, and the like. A cross pin interconnection is shown. The head 442 includes a central aperture 447 and cross holes 448 which are involved in the cross pin interconnection. The head 442 includes a surface 445 that faces toward the distal portion 438. The surface 445 may be concave, convex, or flat or planar. A flat or planar surface 445 is shown. The distal portion 438 includes external threads 452. The external threads 452 may be specifically designed to engage cortical or cancellous bone. The screw 432 may have a blunt, non-cutting distal tip 454. The screw 432 may be inserted into a tapped bone hole. The shank 440 includes transverse grooves 446 on opposite sides of the shank in the proximal portion 436 which are involved in the cross pin interconnection. Elsewhere, the shank 440 may be smooth. The shank 440 has a smaller outer diameter than the outer diameter of the head 442, the aperture 447 of the head 442, or the major diameter of the external threads 452. The outer diameter of the shank 440 may be the same as the minor diameter of the external threads 452, or nearly the same.

The base 434 may be disc shaped with a central aperture 456 sized to receive the shank 440 so that the base 434 is free to slide along the shank 440. The base 434 has a larger outer diameter than the shank 440, and may have a larger outer diameter than the head 442 or the major diameter of the external threads 452. However, the outer diameter of the base 434 may be the same as the outer diameter of the head 442 or the major diameter of the external threads 452, or nearly the same. The base 434 includes a first surface 458 and a second surface 460 opposite the first surface. The aperture 456 pierces the first and second surfaces 458, 460. The first and second surfaces 458, 460 may be concave, convex, or flat or planar. In FIGS. 30B and 30C, the first surface 458 is flat or planar, while in FIGS. 30B and 30D, the second surface 460 is convex.

The spring washer 50 may be spring washer 74, 76, 78, 80, 82, 84, 86, or another size consistent with the principles set forth herein. Referring to FIGS. 2C and 30B, the outer diameter (D) 52 may be the same as the outer diameter of the head 442 or the outer diameter of the base 434, or nearly the same. The outer diameter (D) 52 may be less than or equal to the outer diameter of the head 442 or the outer diameter of the base 434 so that the outer lower edge 72 may rest on the surface 445 of the head 442 or the first surface 458 of the base 434. The inner diameter (d) 54 receives the shank 440 of the screw 432 so that the spring washer 50 is free to slide along the shank 440. The inner diameter (d) 54 may be the same size as the aperture 456.

When the bone screw assembly 430 is operatively assembled, the shank 440 of the screw 432 is received in the inner diameters (d) 54 of the spring washers 50 and the aperture 456 of the base 434. The spring washers 50 are between the head 442 of the screw 432 and the base 434. The first surface 458 of the base 434 may face toward the surface 445 of the head 442 of the screw 432 and the second surface 460 of the base 434 may face toward the distal portion 438 of the screw 432. However, the orientation of the first and second surfaces 458, 460 may be reversed. The upper surface 62 of a proximal one of the spring washers 50 may face toward the surface 445 and the upper surface 62 of a distal one of the spring washers 50 may face toward the first surface 458. However, the lower surfaces 64 may face surfaces 445, 458 instead.

In examples where the head 442 is integral with the screw 432, the bone screw assembly 430 may be assembled by first passing the spring washers 50 and then the base 434 along the external threads 452 from the blunt tip 454 toward the head 442. In this arrangement, the inner diameter (d) 54 and the aperture 456 may be equal to or greater than the minor diameter of the external threads 452 plus one-half of the difference between the major diameter of the external threads and the minor diameter of the external threads. Preferably, the inner diameter (d) 54 and the aperture 456 are optimized to the smallest size that does not damage the inner diameter (d) 54, the aperture 456, or the external threads 452 during assembly.

In examples where the head 442 is coupled to the screw 432 by an interconnection such as the illustrated cross pin interconnection, the bone screw assembly 430 may be assembled by first passing the base 434, then the spring washers 50, and finally the head 442 along the shank 440 from the proximal portion 436 toward the distal portion 438. In this arrangement, the inner diameter (d) 54, the aperture 456, and the aperture 447 may be equal to or greater than the outer diameter of the interconnection and the shank 440. Preferably, the inner diameter (d) 54 and the aperture 456 are optimized to the smallest size that does not damage the inner diameter (d) 54, the aperture 456, the interconnection, or the shank 440 during assembly, and that permits the base 434 and the spring washer 50 to slide freely along the shank 440 in use. The head 442 is positioned relative to the shank 440 so that the grooves 446 of the shank 440 are aligned with the holes 448 of the head 442. Together, the aligned grooves 446 and holes 448 form cylindrical passages that receive cross pins 450 which couple the head 442 and the shank 440 together. The cross pins 450 may be press fit into the cylindrical passages formed by the grooves 446 and the holes 448.

One example of the bone screw assembly 430 has the following dimensions: shank 440 outer diameter is 3 mm, external threads 452 major diameter is 4.5 mm, external threads 452 spacing (pitch) is 1.5 mm, head 442 and base 434 outer diameter is 8 mm, and overall length is 21 mm to 29 mm.

When three bone screw assemblies 430 having the preceding dimensions are installed across the example discontinuity with an installation load of 3000 N each, each bone screw assembly 430 dynamically adjusts to provide a 2000 N load at 0.114 mm (114 μm) of diminution. The 3000 N installation load for each of the three bone screw assemblies 430 causes an average of 30 MPa of bone stress in the discontinuity zone or fracture zone. The 2000 N post-diminution load causes an average of 18 MPa to 20 MPa of bone stress in the discontinuity zone or fracture zone.

Additional information about the cross pin interconnection of bone screw assembly 430 is disclosed in U.S. Provisional Application Ser. No. 62/080,893, at least in FIGS. 41-46 and pages 88-93 of 94; and in U.S. Provisional Application Ser. No. 62/080,954, at least in FIGS. 30-31 and pages 49-51 of 67.

Figure 31A:
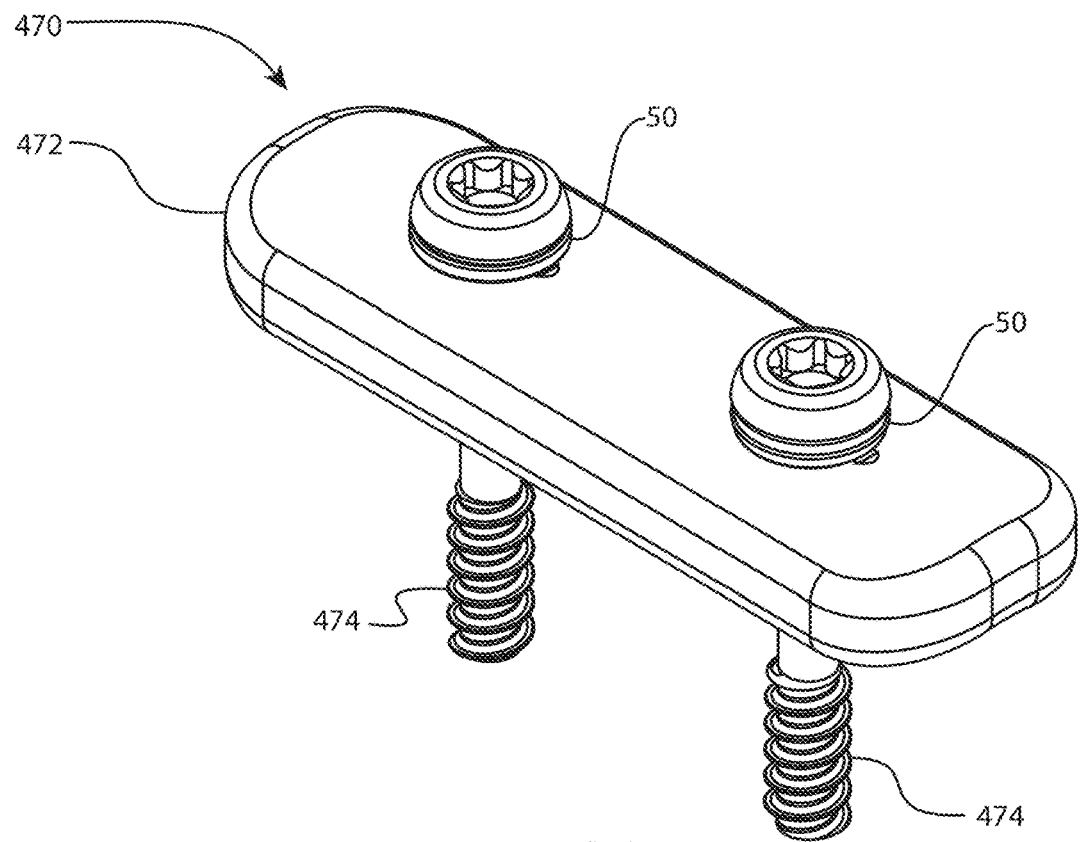
FIG. 31A is an isometric view of a bone plate assembly.
Figure 31B:
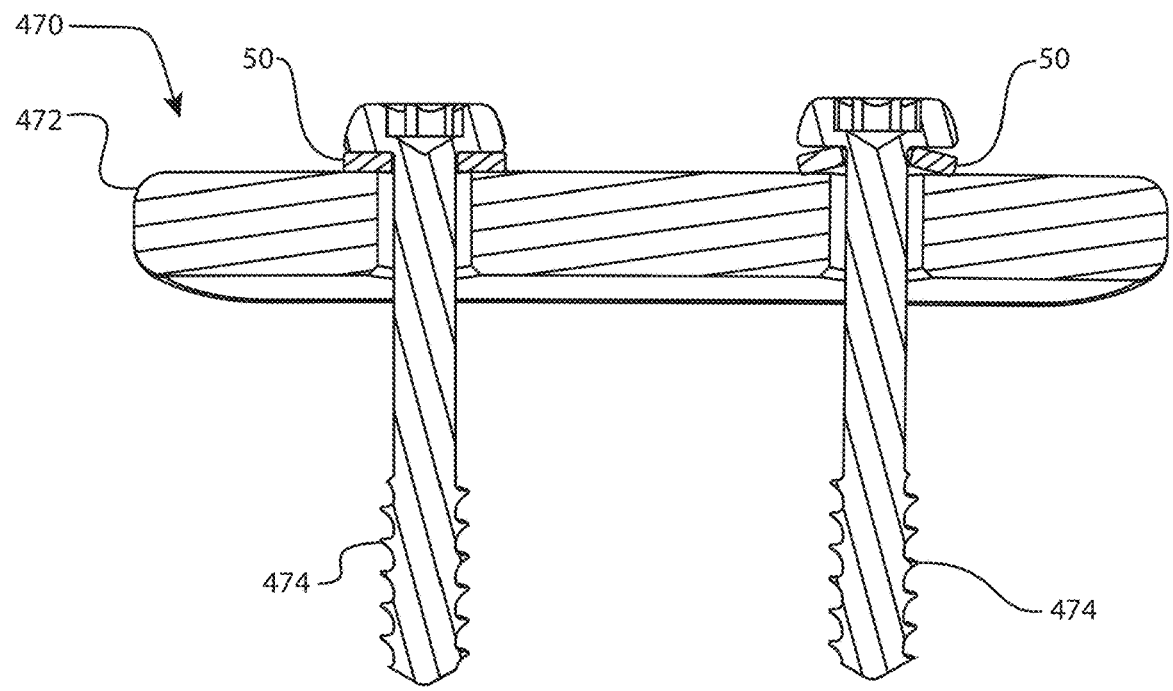
FIG. 31B is a cross sectional view of the bone plate assembly of FIG. 31A.

Referring to FIGS. 31A-31D, a bone plate assembly 470 includes a bone plate 472, a screw 474, and a spring washer 50. Two screws 474 and two spring washers 50 are shown, although any number of screws and spring washers may be included. In FIG. 31B, the left spring washer 50 is shown in its flattened state and the right spring washer is shown in its free state, or undeflected state.

The bone plate 472 includes a bone facing first surface 476 and a second surface 478 opposite the first surface. The first surface 476 and the second surface 478 may be concave, convex, or flat or planar. In FIGS. 31C and 31D, the first surface 476 is concave, while the second surface 478 is convex. An aperture 480 pierces the first and second surfaces 476, 478. Two apertures 480 are shown, although any number of apertures may be included. The aperture 480 may include internal threads. The second surface 478 may include a flattened portion 482 beside the aperture 480. The flattened portion 482 may be planar. Each aperture 480 is illustrated with two flattened portions 482 extending on opposite sides of the aperture; oval or round flattened portions are also contemplated.

The screw 474 may be the screw 402 of bone screw assembly 400 or the screw 432 of bone screw assembly 430. The screw 474 includes a proximal portion 484, a distal portion 486, and a shaft or shank 488 between the proximal portion 484 and the distal portion 486. The proximal portion 484 includes a head 490 with a torque drive feature 492. The torque drive feature 492 may be a protruding feature, such as a hex key, or a recessed feature, such as a hex socket. A hexalobular socket is shown. The head 490 may be integrally formed with the shank 488, or the head 490 may be coupled to the shank 488 by an interconnection such as threads, cross pins, press fit, weld, peening, and the like. The head 490 includes a surface 493 that faces toward the distal portion 486. The surface 493 may be concave, convex, or flat or planar. The distal portion 486 includes external threads 494. The external threads 494 may be specifically designed to engage cortical or cancellous bone. The external threads 494 may be complementary to the internal threads in the aperture 480, if present. The screw 474 may have a blunt, non-cutting distal tip 496. The screw 474 may be inserted into a tapped bone hole. The shank 488 may be smooth. The shank 488 may taper outwardly toward the head 490. The shank 488 has a smaller outer diameter than the head 490 or the major diameter of the external threads 494. The outer diameter of the shank 488 may be the same as the minor diameter of the external threads 494, or nearly the same.

The spring washer 50 may be spring washer 74, 76, 78, 80, 82, 84, 86, or another size consistent with the principles set forth herein. Referring to FIGS. 2C and 31B, the outer diameter (D) 52 may be the same as the outer diameter of the head 490, or nearly the same. The outer diameter (D) 52 may be less than or equal to the outer diameter of the head 490 so that the outer lower edge 72 may rest on the surface 493 of the head 490. The outer diameter (D) 52 may be larger than the aperture 480 of the bone plate 472. The inner diameter (d) 54 receives the shank 488 of the screw 474 so that the spring washer 50 is free to slide along the shank 488. The inner diameter (d) 54 may be the same size as the aperture 480, although FIG. 31B shows an arrangement in which the inner diameter (d) 54 is smaller than the aperture 480.

When the bone plate assembly 470 is operatively assembled, the shank 488 of the screw 474 is received in the inner diameter (d) 54 of the spring washer 50 and the aperture 480 of the bone plate 472. The spring washer 50 is between the head 490 of the screw 474 and the bone plate 472. The second surface 478 of the bone plate 472 may face toward the surface 493 of the head 490 of the screw 474 and the first surface 476 of the bone plate 472 may face toward the distal portion 486 of the screw 474. The upper surface 62 of the spring washer 50 may face toward the surface 493 and the lower surface 64 of the spring washer 50 may face toward the second surface 478. The outer lower edge 72 of the spring washer 50 may rest on the flattened portion 482. However, the orientation of the upper and lower surfaces 62, 64 may be reversed so that the outer lower edge 72 of the spring washer 50 rests on the surface 493.

In examples where the head 490 is integral with the screw 474, the spring washer 50 may be assembled to the screw 474 by passing the spring washer 50 along the external threads 494 from the blunt tip 496 toward the head 490. In this arrangement, the inner diameter (d) 54 may be equal to or greater than the minor diameter of the external threads 494 plus one-half of the difference between the major diameter of the external threads and the minor diameter of the external threads. Preferably, the inner diameter (d) 54 is optimized to the smallest size that does not damage the inner diameter (d) 54 or the external threads 416 during assembly. The screw 474, coupled to the spring washer 50, may be provided to an end user as a sub-assembly separate from the bone plate 472. The end user may drive the distal portion 486 of the screw 474 through the aperture 480 of the bone plate 472 from the second surface 478 toward the first surface 476 so that the spring washer 50 is between the surface 493 of the head 490 and the second surface 478 (or the flattened portion 482) of the bone plate 472.

In examples where the head 490 is coupled to the screw 474 by an interconnection, the spring washer 50 may be assembled to the screw 474 by passing the spring washer 50 along the shank 488 from the proximal portion 484 toward the distal portion 486. In this arrangement, the inner diameter (d) 54 may be equal to or greater than the outer diameter of the interconnection and the shank 488. Preferably, the inner diameter (d) 54 is optimized to the smallest size that does not damage the inner diameter (d) 54, the interconnection, or the shank 488 during assembly, and that permits the spring washer 50 to slide freely along the shank 488 in use. The screw 474, with spring washer 50, may be provided to an end user as a sub-assembly separate from the bone plate 472. The end user may drive the sub-assembly through the bone plate 472 as described in the preceding paragraph.

Referring to FIGS. 32A-32D, a bone plate assembly 500 includes a bone plate 502, a screw 504, and a spring washer

Figure 32A:
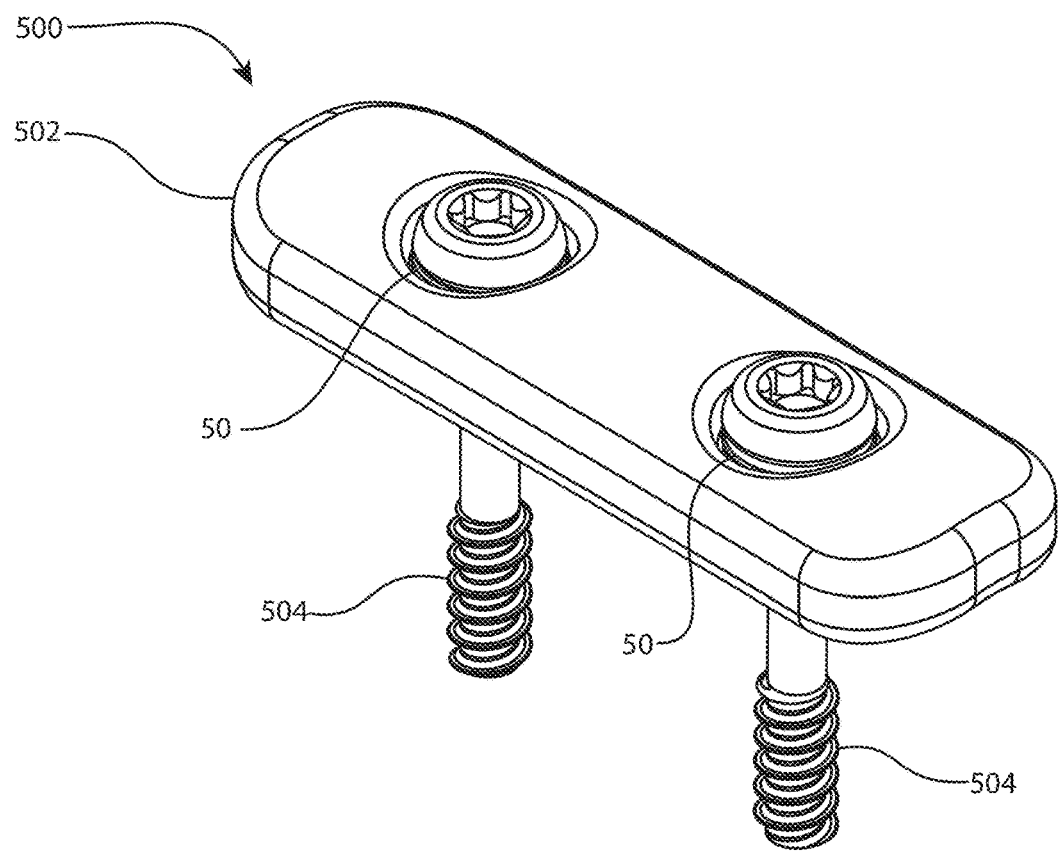
FIG. 32A is an isometric view of another bone plate assembly.
Figure 32B:
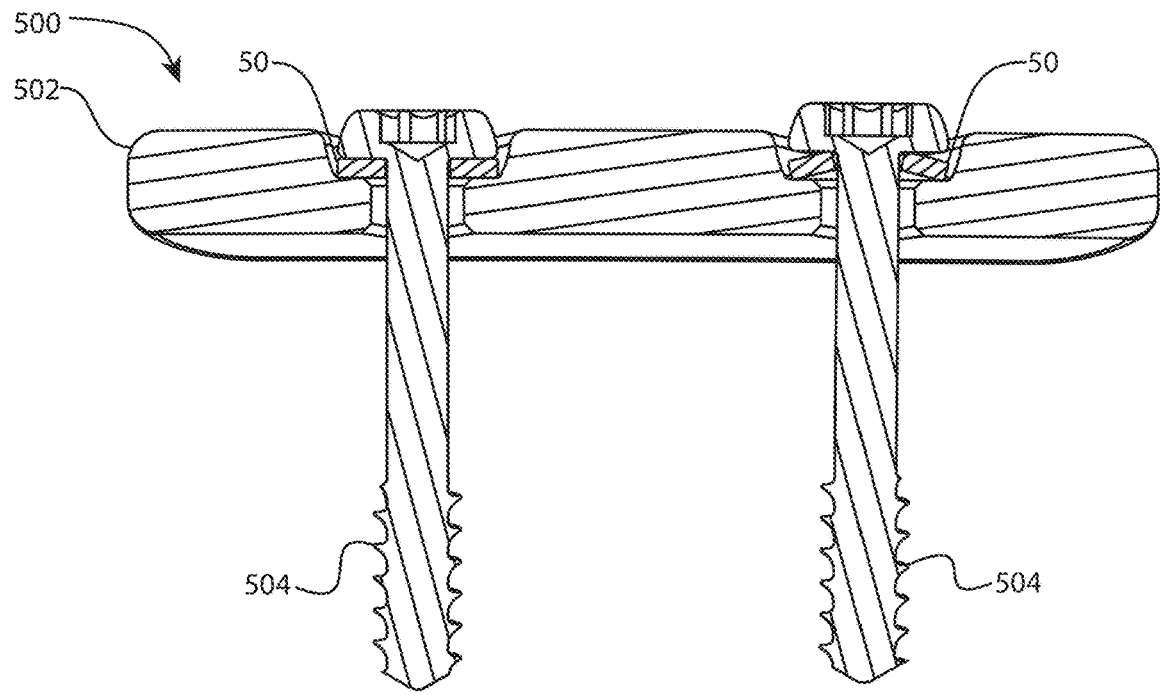
FIG. 32B is a cross sectional view of the bone plate assembly of FIG. 32A.

50. Two screws 504 and two spring washers 50 are shown, although any number of screws and spring washers may be included. In FIG. 32B, the left spring washer 50 is shown in its flattened state and the right spring washer is shown in its free state, or undeflected state.

Figure 32D:
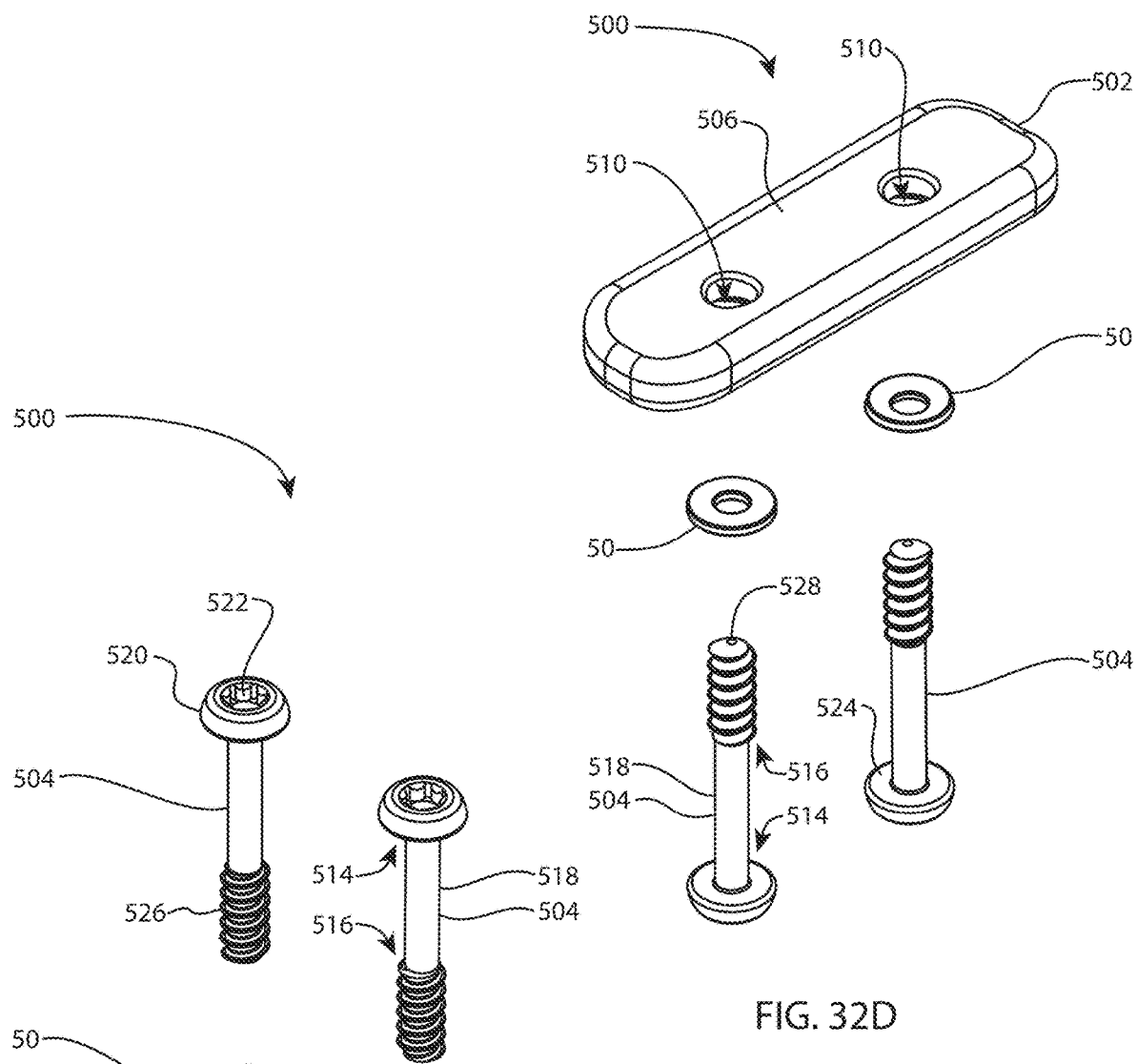
FIG. 32D is another exploded view of the bone plate assembly of FIG. 32A from a different viewpoint.
Figure 32C:
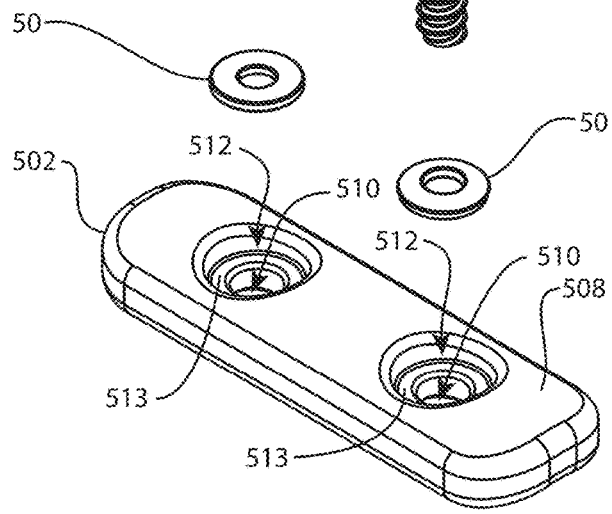
FIG. 32C is an exploded view of the bone plate assembly of FIG. 32A.

The bone plate 502 includes a bone facing first surface 506 and a second surface 508 opposite the first surface. The first surface 506 and the second surface 508 may be concave, convex, or flat or planar. In FIGS. 32C and 32D, the first surface 506 is concave, while the second surface 508 is convex. An aperture 510 pierces the first and second surfaces 506, 508. Two apertures 510 are shown, although any number of apertures may be included. The aperture 510 may include internal threads. In this example, a recess 512 is provided around each aperture 510 extending into the bone plate 502 from the second surface 508. The recess 512 includes a bottom surface 513 which may be flat or planar. The bottom surface 513 lies below the second surface 508.

The screw 504 may be the screw 402 of bone screw assembly 400 or the screw 432 of bone screw assembly 430. The screw 504 includes a proximal portion 514, a distal portion 516, and a shaft or shank 518 between the proximal portion 514 and the distal portion 516. The proximal portion 514 includes a head 520 with a torque drive feature 522. The torque drive feature 522 may be a protruding feature, such as a hex key, or a recessed feature, such as a hex socket. A hexalobular socket is shown. The head 520 may be integrally formed with the shank 518, or the head 520 may be coupled to the shank 518 by an interconnection such as threads, cross pins, press fit, weld, peening, and the like. The head 520 includes a surface 524 that faces toward the distal portion 516. The surface 524 may be concave, convex, or flat or planar. The distal portion 516 includes external threads 526. The external threads 526 may be specifically designed to engage cortical or cancellous bone. The external threads 526 may be complementary to the internal threads in the aperture 510, if present. The screw 504 may have a blunt, non-cutting distal tip 528. The screw 504 may be inserted into a tapped bone hole. The shank 518 may be smooth. The shank 518 may taper outwardly toward the head 520. The shank 518 has a smaller outer diameter than the head 520 or the major diameter of the external threads 526. The outer diameter of the shank 518 may be the same as the minor diameter of the external threads 526, or nearly the same.

The spring washer 50 may be spring washer 74, 76, 78, 80, 82, 84, 86, or another size consistent with the principles set forth herein. Referring to FIGS. 2C and 32B, the outer diameter (D) 52 may be the same as the outer diameter of the head 520, or nearly the same. The outer diameter (D) 52 may be less than or equal to the outer diameter of the head 520 so that the outer lower edge 72 may rest on the surface 524 of the head 520. The outer diameter (D) 52 may be larger than the aperture 510 of the bone plate 502. The inner diameter (d) 54 receives the shank 518 of the screw 504 so that the spring washer 50 is free to slide along the shank 518. The inner diameter (d) 54 may be the same size as the aperture 510, although FIG. 32B shows an arrangement in which the inner diameter (d) 54 is smaller than the aperture 510.

When the bone plate assembly 500 is operatively assembled, the shank 518 of the screw 504 is received in the inner diameter (d) 54 of the spring washer 50 and the aperture 510 of the bone plate 502. The spring washer 50 is received in the recess 512 and is between the head 520 of the screw 504 and the bottom surface 513 of the recess 512. The bottom surface 513 may face toward the surface 524 of the head 520 of the screw 504 and the first surface 506 of the bone plate 502 may face toward the distal portion 516 of the screw 504. The upper surface 62 of the spring washer 50 may face toward the surface 524 and the lower surface 64 of the spring washer 50 may face toward the bottom surface 513. The outer lower edge 72 of the spring washer 50 may rest on the bottom surface 513. However, the orientation of the upper and lower surfaces 62, 64 may be reversed so that the outer lower edge 72 of the spring washer 50 rests on the surface 524. Referring to FIG. 32B, the recess 512 is deeper than the overall height (H) 56 of the spring washer 50 in its free state so that the entire spring washer is recessed below the second surface 508.

In examples where the head 520 is integral with the screw 504, the spring washer 50 may be assembled to the screw 504 by passing the spring washer 50 along the external threads 526 from the blunt tip 528 toward the head 520. In this arrangement, the inner diameter (d) 54 may be equal to or greater than the minor diameter of the external threads 526 plus one-half of the difference between the major diameter of the external threads and the minor diameter of the external threads. Preferably, the inner diameter (d) 54 is optimized to the smallest size that does not damage the inner diameter (d) 54 or the external threads 416 during assembly. The screw 504, coupled to the spring washer 50, may be provided to an end user as a sub-assembly separate from the bone plate 502. The end user may drive the distal portion 516 of the screw 504 through the aperture 510 of the bone plate 502 from the second surface 508 toward the first surface 506 so that the spring washer 50 is in the recess 512 between the surface 524 of the head 520 and the bottom surface 513 of the recess 512.

In examples where the head 520 is coupled to the screw 504 by an interconnection, the spring washer 50 may be assembled to the screw 504 by passing the spring washer 50 along the shank 518 from the proximal portion 514 toward the distal portion 516. In this arrangement, the inner diameter (d) 54 may be equal to or greater than the outer diameter of the interconnection and the shank 518. Preferably, the inner diameter (d) 54 is optimized to the smallest size that does not damage the inner diameter (d) 54, the interconnection, or the shank 518 during assembly, and that permits the spring washer 50 to slide freely along the shank 518 in use. The screw 504, with spring washer 50, may be provided to an end user as a sub-assembly separate from the bone plate 502. The end user may drive the sub-assembly through the bone plate 502 as described in the preceding paragraph.

Figure 33A:
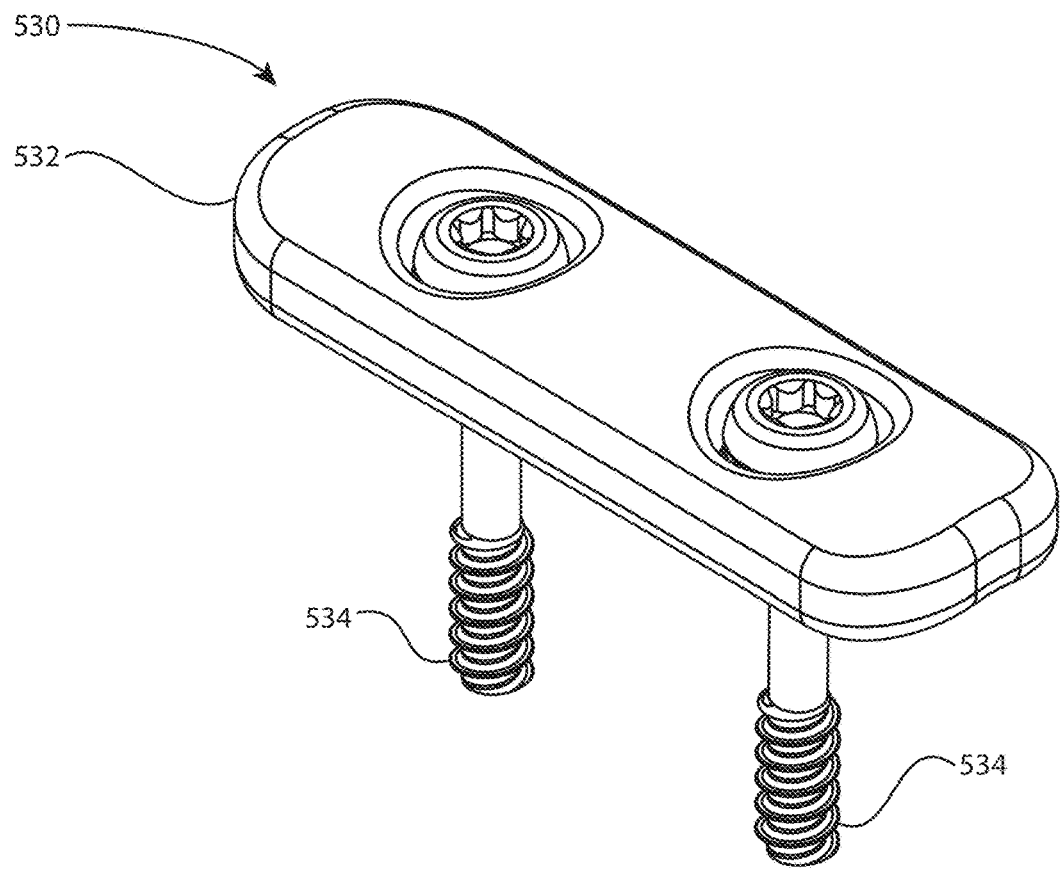
FIG. 33A is an isometric view of yet another bone plate assembly.
Figure 33B:
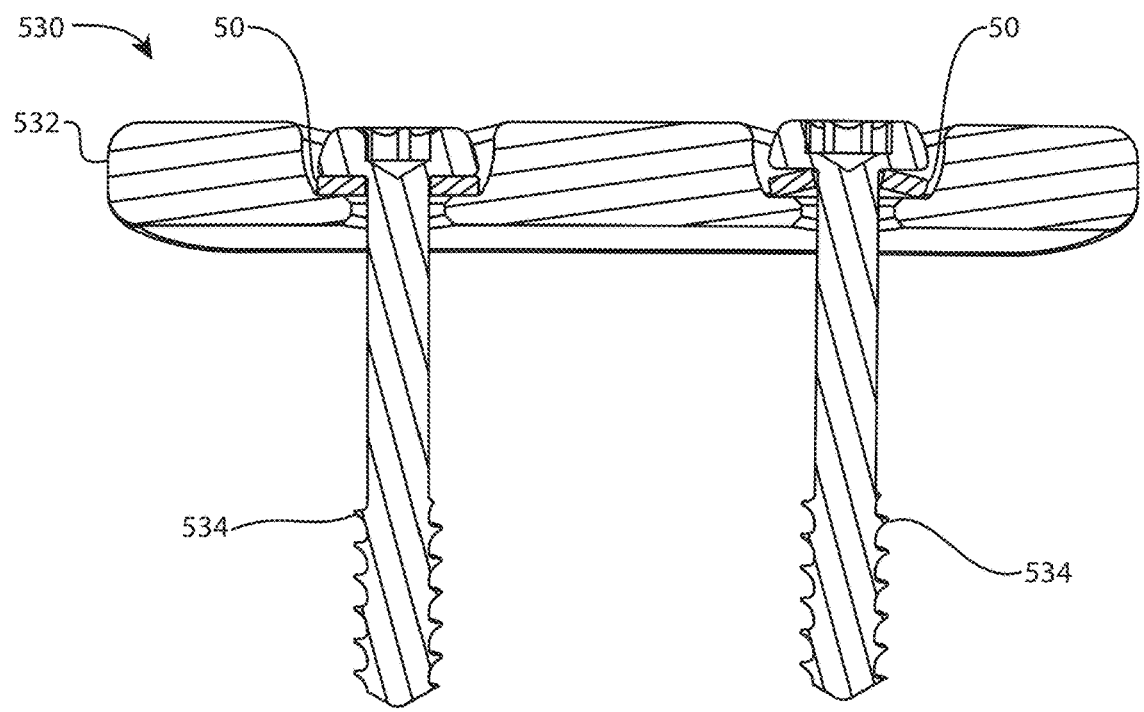
FIG. 33B is a cross sectional view of the bone plate assembly of FIG. 33A.

Referring to FIGS. 33A-33D, a bone plate assembly 530 includes a bone plate 532, a screw 534, and a spring washer 50. Two screws 534 and two spring washers 50 are shown, although any number of screws and spring washers may be included. In FIG. 33B, the left spring washer 50 is shown in its flattened state and the right spring washer is shown in its free state, or undeflected state.

Figure 33D:
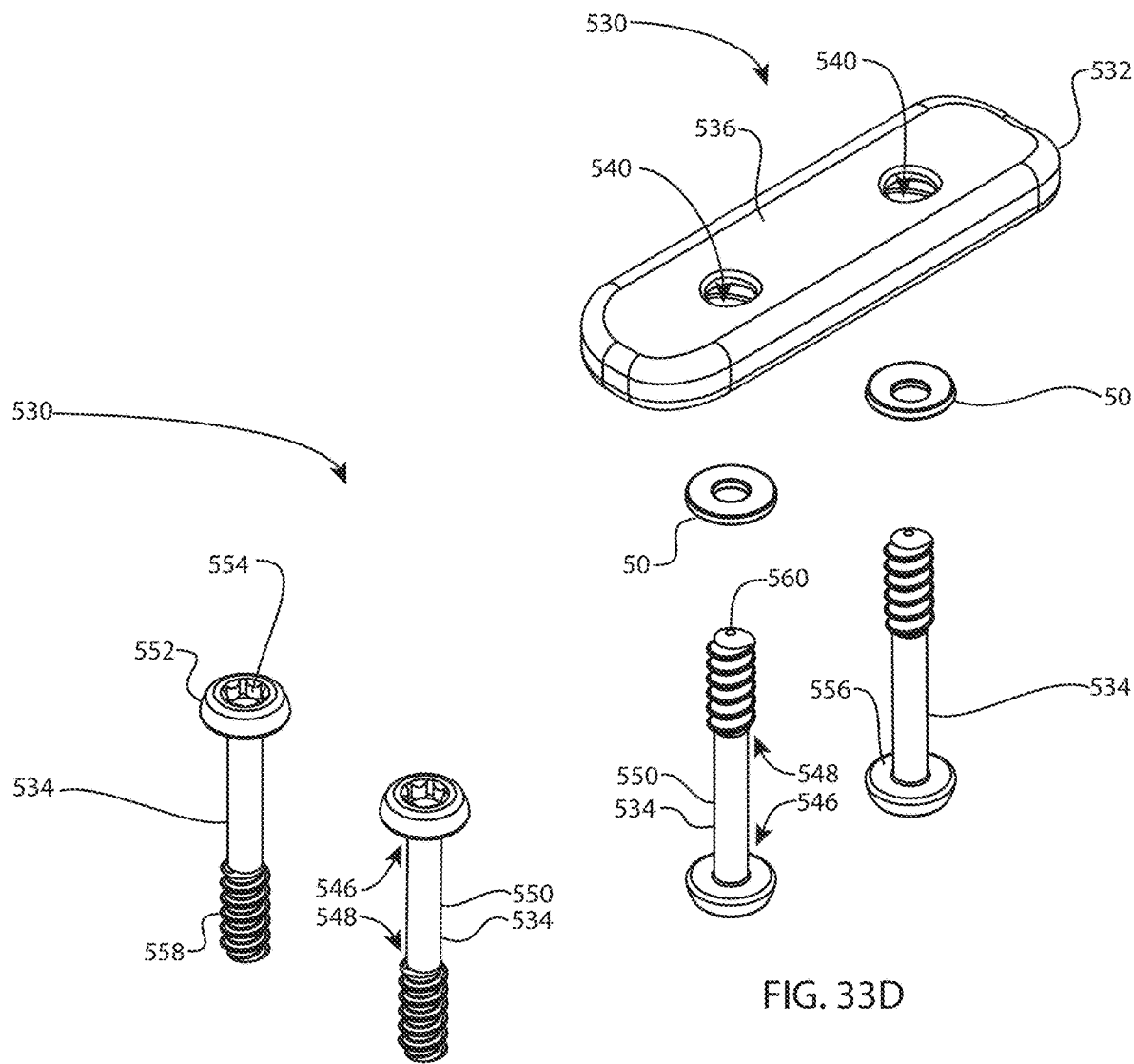
FIG. 33D is another exploded view of the bone plate assembly of FIG. 33A from a different viewpoint.
Figure 33C:
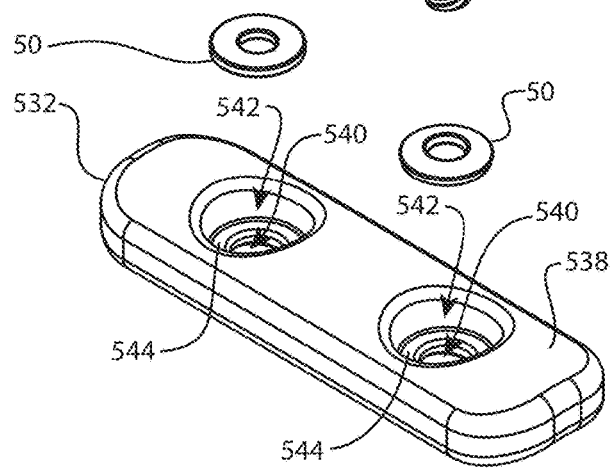
FIG. 33C is an exploded view of the bone plate assembly of FIG. 33A.

The bone plate 532 includes a bone facing first surface 536 and a second surface 538 opposite the first surface. The first surface 536 and the second surface 538 may be concave, convex, or flat or planar. In FIGS. 33C and 33D, the first surface 536 is concave, while the second surface 538 is convex. An aperture 540 pierces the first and second surfaces 536, 538. Two apertures 540 are shown, although any number of apertures may be included. The aperture 540 may include internal threads. In this example, a recess 542 is provided around each aperture 540 extending into the bone plate 532 from the second surface 538. The recess 542 includes a bottom surface 544 which may be flat or planar. The bottom surface 544 lies below the second surface 538.

The screw 534 may be the screw 402 of bone screw assembly 400 or the screw 432 of bone screw assembly 430. The screw 534 includes a proximal portion 546, a distal portion 548, and a shaft or shank 550 between the proximal portion 546 and the distal portion 548. The proximal portion 546 includes a head 552 with a torque drive feature 554. The torque drive feature 554 may be a protruding feature, such as a hex key, or a recessed feature, such as a hex socket. A hexalobular socket is shown. The head 552 may be integrally formed with the shank 550, or the head 552 may be coupled to the shank 550 by an interconnection such as threads, cross pins, press fit, weld, peening, and the like. The head 552 includes a surface 556 that faces toward the distal portion 548. The surface 556 may be concave, convex, or flat or planar. The distal portion 548 includes external threads 558. The external threads 558 may be specifically designed to engage cortical or cancellous bone. The external threads 558 may be complementary to the internal threads in the aperture 540, if present. The screw 534 may have a blunt, non-cutting distal tip 560. The screw 534 may be inserted into a tapped bone hole. The shank 550 may be smooth. The shank 550 may taper outwardly toward the head 552. The shank 550 has a smaller outer diameter than the head 552 or the major diameter of the external threads 558. The outer diameter of the shank 550 may be the same as the minor diameter of the external threads 558, or nearly the same.

The spring washer 50 may be spring washer 74, 76, 78, 80, 82, 84, 86, or another size consistent with the principles set forth herein. Referring to FIGS. 2C and 33B, the outer diameter (D) 52 may be the same as the outer diameter of the head 552, or nearly the same. The outer diameter (D) 52 may be less than or equal to the outer diameter of the head 552 so that the outer lower edge 72 may rest on the surface 556 of the head 552. The outer diameter (D) 52 may be larger than the aperture 540 of the bone plate 532. The inner diameter (d) 54 receives the shank 550 of the screw 534 so that the spring washer 50 is free to slide along the shank 550. The inner diameter (d) 54 may be the same size as the aperture 540, although FIG. 33B shows an arrangement in which the inner diameter (d) 54 is smaller than the aperture 540.

When the bone plate assembly 530 is operatively assembled, the shank 550 of the screw 534 is received in the inner diameter (d) 54 of the spring washer 50 and the aperture 540 of the bone plate 532. The spring washer 50 is received in the recess 542 and is between the head 552 of the screw 534 and the bottom surface 544 of the recess 542. The bottom surface 544 may face toward the surface 556 of the head 552 of the screw 534 and the first surface 536 of the bone plate 532 may face toward the distal portion 548 of the screw 534. The upper surface 62 of the spring washer 50 may face toward the surface 556 and the lower surface 64 of the spring washer 50 may face toward the bottom surface 544. The outer lower edge 72 of the spring washer 50 may rest on the bottom surface 544. However, the orientation of the upper and lower surfaces 62, 64 may be reversed so that the outer lower edge 72 of the spring washer 50 rests on the surface 556. Referring to FIG. 33B, the recess 542 is deeper than the overall height (H) 56 of the spring washer 50 in its flat state plus the overall height of the head 552 of the screw 534 so that the entire head 552 and spring washer 50 are recessed below the second surface 538.

In examples where the head 552 is integral with the screw 534, the spring washer 50 may be assembled to the screw 534 by passing the spring washer 50 along the external threads 558 from the blunt tip 560 toward the head 552. In this arrangement, the inner diameter (d) 54 may be equal to or greater than the minor diameter of the external threads 558 plus one-half of the difference between the major diameter of the external threads and the minor diameter of the external threads. Preferably, the inner diameter (d) 54 is optimized to the smallest size that does not damage the inner diameter (d) 54 or the external threads 416 during assembly. The screw 534, coupled to the spring washer 50, may be provided to an end user as a sub-assembly separate from the bone plate 532. The end user may drive the distal portion 548 of the screw 534 through the aperture 540 of the bone plate 532 from the second surface 538 toward the first surface 536 so that the spring washer 50 is in the recess 542 between the surface 556 of the head 552 and the bottom surface 544 of the recess 542.

In examples where the head 552 is coupled to the screw 534 by an interconnection, the spring washer 50 may be assembled to the screw 534 by passing the spring washer 50 along the shank 550 from the proximal portion 546 toward the distal portion 548. In this arrangement, the inner diameter (d) 54 may be equal to or greater than the outer diameter of the interconnection and the shank 550. Preferably, the inner diameter (d) 54 is optimized to the smallest size that does not damage the inner diameter (d) 54, the interconnection, or the shank 550 during assembly, and that permits the spring washer 50 to slide freely along the shank 550 in use. The screw 534, with spring washer 50, may be provided to an end user as a sub-assembly separate from the bone plate 532. The end user may drive the sub-assembly through the bone plate 532 as described in the preceding paragraph.

Figure 34A:
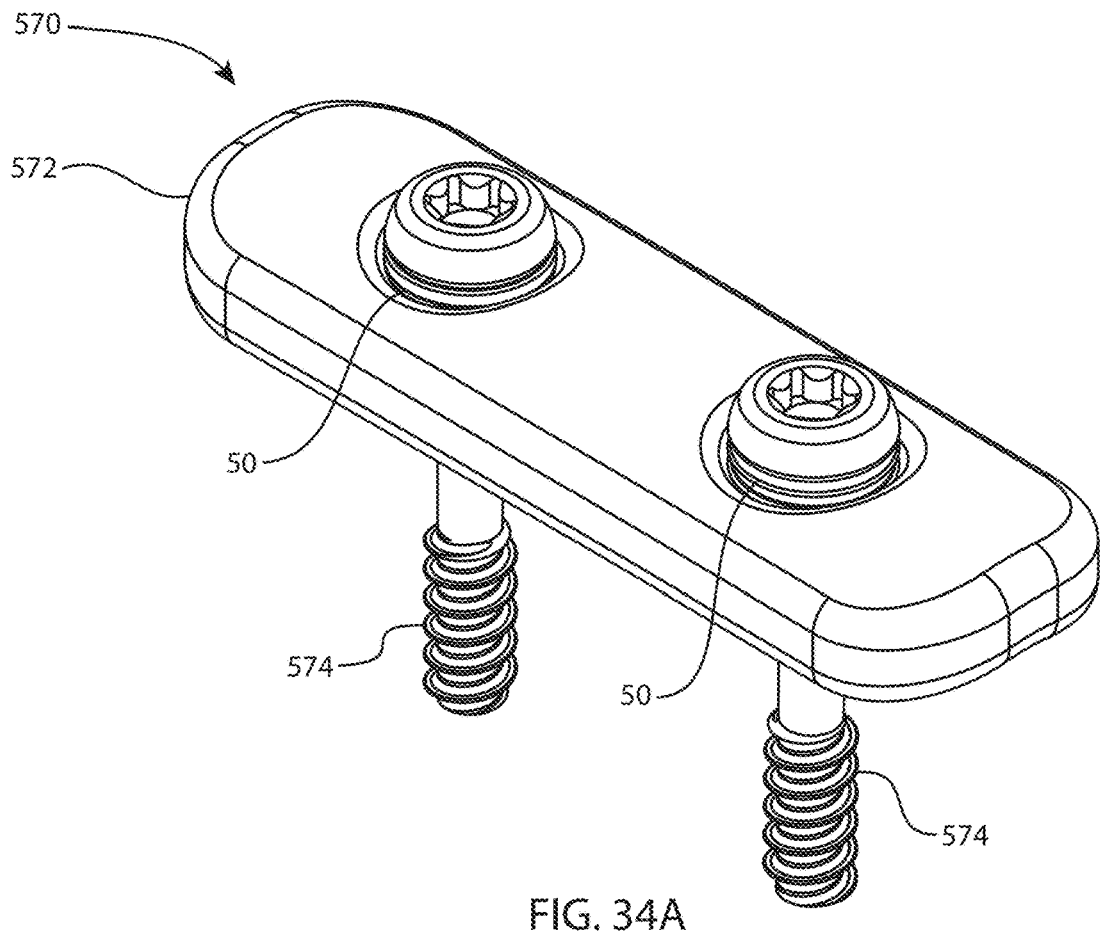
FIG. 34A is an isometric view of yet another bone plate assembly.
Figure 34B:
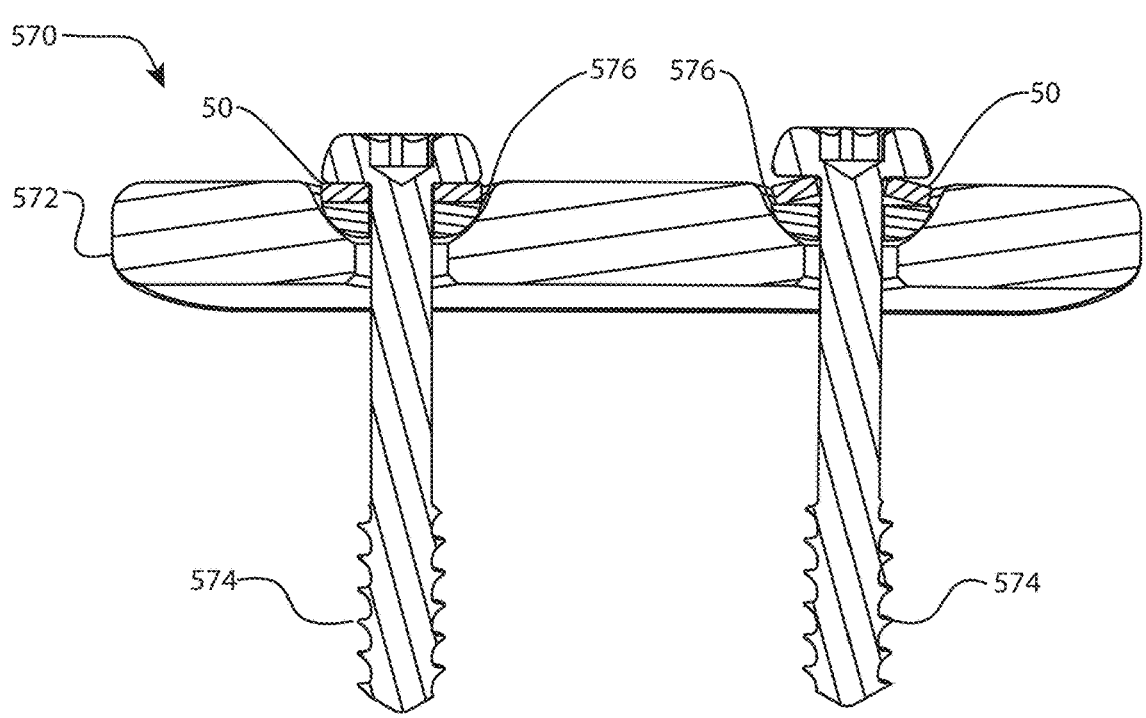
FIG. 34B is a cross sectional view of the bone plate assembly of FIG. 34A.

Referring to FIGS. 34A-34D, a bone plate assembly 570 includes a bone plate 572, a screw 574, a spring washer 50, and a base 576. Two screws 574, two spring washers 50, and two bases 576 are shown, although any number of screws, spring washers, and bases may be included. In FIG. 34B, the left spring washer 50 is shown in its flattened state and the right spring washer is shown in its free state, or undeflected state.

Figures 34, 34D:
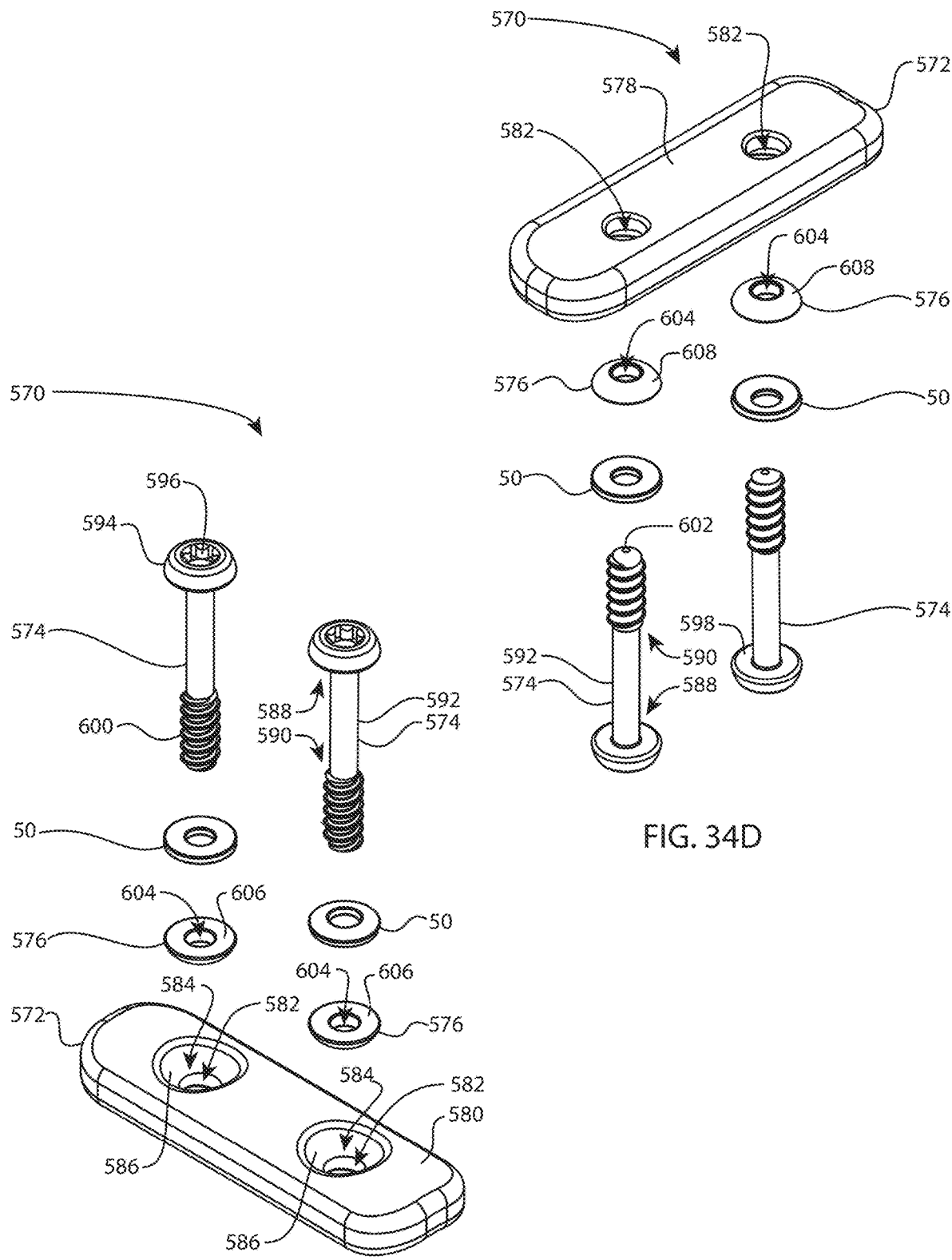
FIG. 34D is another exploded view of the bone plate assembly of FIG. 34A from a different viewpoint.

The bone plate 572 includes a bone facing first surface 578 and a second surface 580 opposite the first surface. The first surface 578 and the second surface 580 may be concave, convex, or flat or planar. In FIGS. 34C and 34D, the first surface 578 is concave, while the second surface 580 is convex. An aperture 582 pierces the first and second surfaces 578, 580. Two apertures 582 are shown, although any number of apertures may be included. The aperture 582 may include internal threads. The internal threads may be offset from the center of the aperture 582. In this example, a recess 584 is provided around each aperture 582 extending into the bone plate 572 from the second surface 580. The recess 584 includes a spherical interior surface 586.

The screw 574 may be the screw 402 of bone screw assembly 400 or the screw 432 of bone screw assembly 430. The screw 574 includes a proximal portion 588, a distal portion 590, and a shaft or shank 592 between the proximal portion 588 and the distal portion 590. The proximal portion 588 includes a head 594 with a torque drive feature 596. The torque drive feature 596 may be a protruding feature, such as a hex key, or a recessed feature, such as a hex socket. A hexalobular socket is shown. The head 594 may be integrally formed with the shank 592, or the head 594 may be coupled to the shank 592 by an interconnection such as threads, cross pins, press fit, weld, peening, and the like. The head 594 includes a surface 598 that faces toward the distal portion 590. The surface 598 may be concave, convex, or flat or planar. The distal portion 590 includes external threads 600. The external threads 600 may be specifically designed to engage cortical or cancellous bone. The external threads 600 may be complementary to the internal threads in the aperture 582, if present. The screw 574 may have a blunt, non-cutting distal tip 602. The screw 574 may be inserted into a tapped bone hole. The shank 592 may be smooth. The shank 592 may taper outwardly toward the head 594. The shank 592 has a smaller outer diameter than the head 594 or the major diameter of the external threads 600. The outer diameter of the shank 592 may be the same as the minor diameter of the external threads 600, or nearly the same.

The base 576 may be disc shaped with a central aperture 604 sized to receive the shank 592 so that the base 576 is free to slide along the shank 592. The base 576 has a larger outer diameter than the shank 592, and may have a larger outer diameter than the head 594, the major diameter of the external threads 600, or the aperture 582 of the bone plate 572. However, the outer diameter of the base 576 may be the same as the outer diameter of the head 594 or the major diameter of the external threads 600, or nearly the same. The base 576 includes a first surface 606 and a second surface 608 opposite the first surface. The aperture 604 pierces the first and second surfaces 606, 608. The first and second surfaces 606, 608 may be concave, convex, or flat or planar. In FIGS. 34B and 34C, the first surface 606 is flat or planar, while in FIGS. 34B and 34D, the second surface 608 is convex spherical and complementary to the spherical interior surface 586 of the recess 582 of the bone plate 572. The convex spherical second surface 608 forms a ball and socket joint with the spherical interior surface 586, which permits the screw 574, spring washer 50, and base 576 to polyaxially pivot within the recess 584.

The spring washer 50 may be spring washer 74, 76, 78, 80, 82, 84, 86, or another size consistent with the principles set forth herein. Referring to FIGS. 2C and 34B, the outer diameter (D) 52 may be the same as the outer diameter of the head 594 or the outer diameter of the base 576, or nearly the same. The outer diameter (D) 52 may be less than or equal to the outer diameter of the head 594 or the outer diameter of the base 576 so that the outer lower edge 72 may rest on the surface 598 of the head 594 or the first surface 606 of the base 576. The outer diameter (D) 52 may be larger than the aperture 582 of the bone plate 572. The inner diameter (d) 54 receives the shank 592 of the screw 574 so that the spring washer 50 is free to slide along the shank 592. The inner diameter (d) 54 may be the same size as the aperture 582, although FIG. 34B shows an arrangement in which the inner diameter (d) 54 is smaller than the aperture 582.

When the bone plate assembly 570 is operatively assembled, the shank 592 of the screw 574 is received in the inner diameter (d) 54 of the spring washer 50, the aperture 604 of the base 576, and the aperture 582 of the bone plate 572. The base 576 and the spring washer 50 are received in the recess 584. The base 576 is between the spring washer 50 and the spherical interior surface 586 of the recess 584. The spring washer 50 is between the head 594 of the screw 574 and the base 576. The surfaces 586, 606 may face toward the surface 598 of the head 594 of the screw 574 and the surfaces 578, 608 may face toward the distal portion 590 of the screw 574. The upper surface 62 of the spring washer 50 may face toward the surface 598 and the lower surface 64 of the spring washer 50 may face toward the first surface 606. The outer lower edge 72 of the spring washer 50 may rest on the first surface 606. However, the orientation of the upper and lower surfaces 62, 64 may be reversed so that the outer lower edge 72 of the spring washer 50 rests on the surface 598. Referring to FIG. 34B, the recess 584 is deeper than the overall height (H) 56 of the spring washer 50 in its flat state plus the overall height of the base 576 so that the entire spring washer 50 and base 576 are recessed below the second surface 580.

In examples where the head 594 is integral with the screw 574, the spring washer 50 and base 576 may be assembled to the screw 574 by first passing the spring washer 50 and then the base 576 along the external threads 600 from the blunt tip 602 toward the head 594. In this arrangement, the inner diameter (d) 54 and the aperture 604 may be equal to or greater than the minor diameter of the external threads 600 plus one-half of the difference between the major diameter of the external threads and the minor diameter of the external threads. Preferably, the inner diameter (d) 54 and the aperture 604 are optimized to the smallest size that does not damage the inner diameter (d) 54, the aperture 604, or the external threads 416 during assembly. The screw 574, coupled to the spring washer 50 and base 576, may be provided to an end user as a sub-assembly separate from the bone plate 572. The end user may drive the distal portion 590 of the screw 574 through the aperture 582 of the bone plate 572 from the second surface 580 toward the first surface 578 so that the spring washer 50 and the base 576 are in the recess 584 between the surface 598 of the head 594 and the bottom surface 586 of the recess 584.

In examples where the head 594 is coupled to the screw 574 by an interconnection, the spring washer 50 and base 576 may be assembled to the screw 574 by first passing the base 576 and then the spring washer 50 along the shank 592 from the proximal portion 588 toward the distal portion 590. In this arrangement, the inner diameter (d) 54 and the aperture 604 may be equal to or greater than the outer diameter of the interconnection and the shank 592. Preferably, the inner diameter (d) 54 and the aperture 604 are optimized to the smallest size that does not damage the inner diameter (d) 54, the aperture 604, the interconnection, or the shank 592 during assembly, and that permits the spring washer 50 and base 576 to slide freely along the shank 592 in use. The screw 574, with spring washer 50 and base 576, may be provided to an end user as a sub-assembly separate from the bone plate 572. The end user may drive the sub-assembly through the bone plate 572 as described in the preceding paragraph.

Figure 35A:
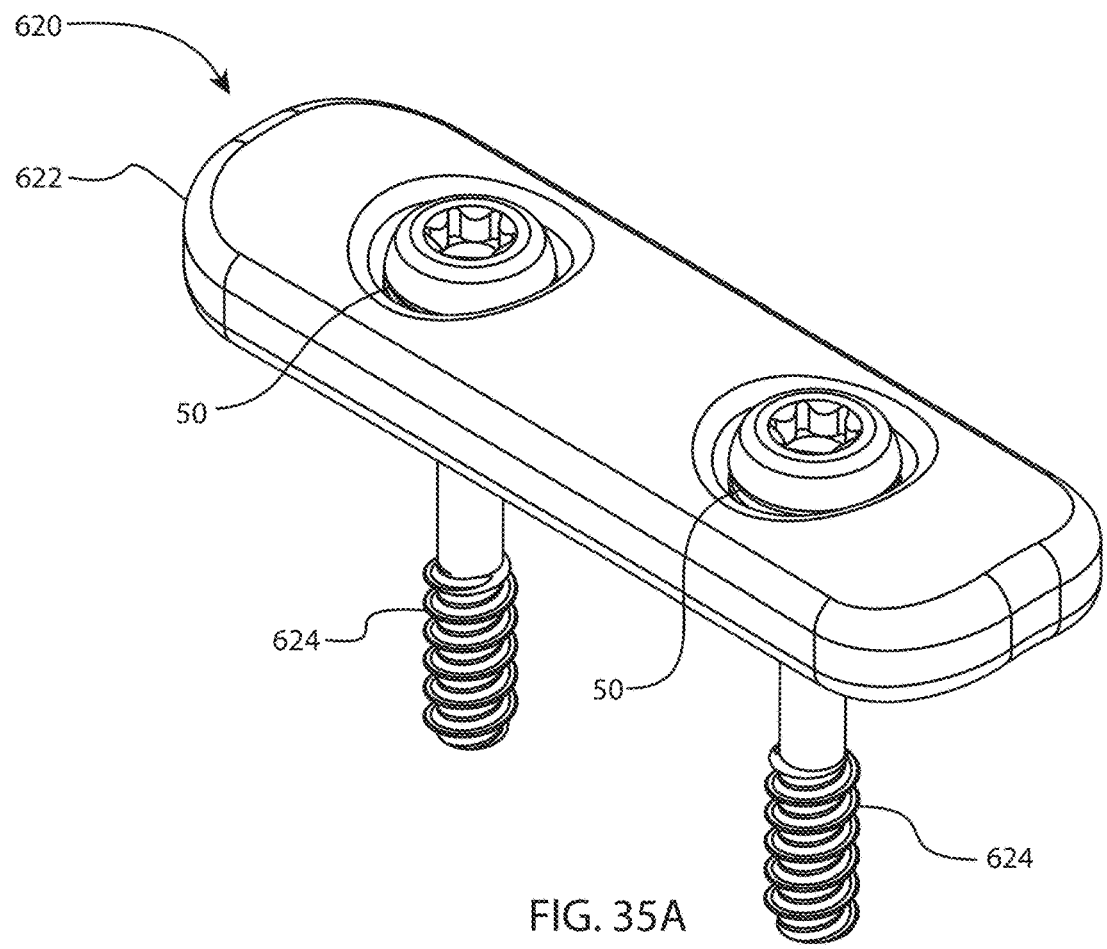
FIG. 35A is an isometric view of yet another bone plate assembly.
Figure 35B:
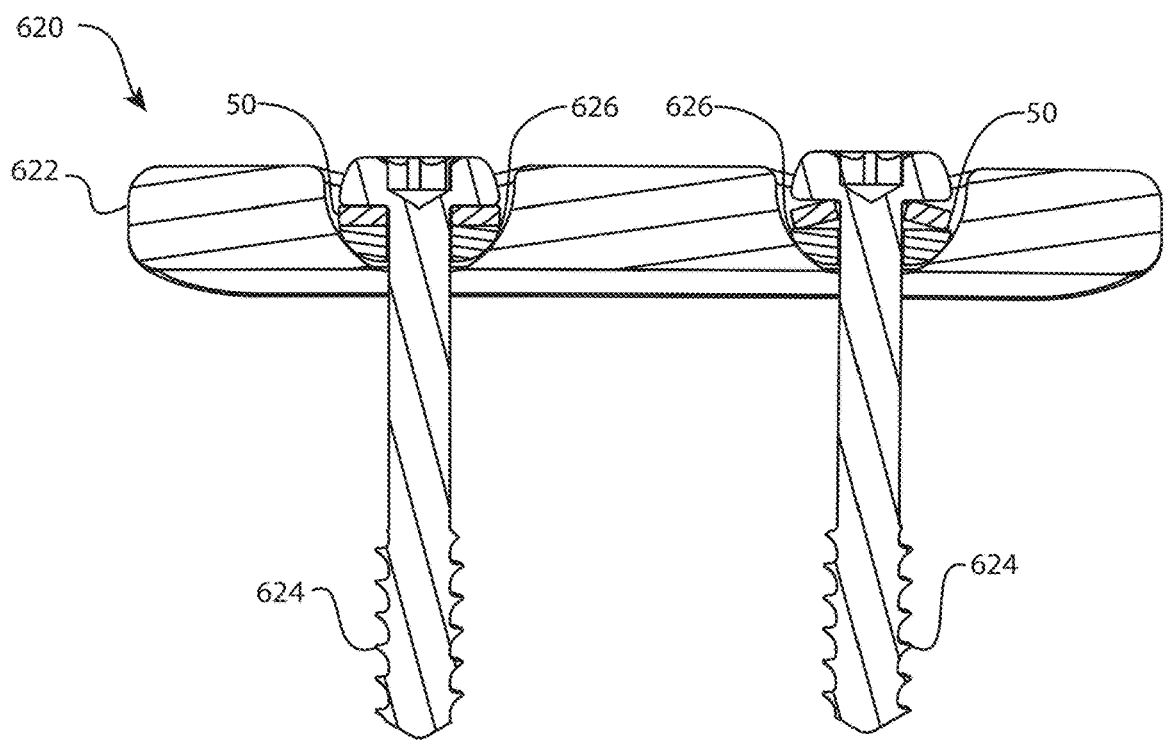
FIG. 35B is a cross sectional view of the bone plate assembly of FIG. 35A.

Referring to FIGS. 35A-35D, a bone plate assembly 620 includes a bone plate 622, a screw 624, a spring washer 50, and a base 626. Two screws 624, two spring washers 50, and two bases 626 are shown, although any number of screws, spring washers, and bases may be included. In FIG. 35B, the left spring washer 50 is shown in its flattened state and the right spring washer is shown in its free state, or undeflected state.

Figures 35C, 35D:
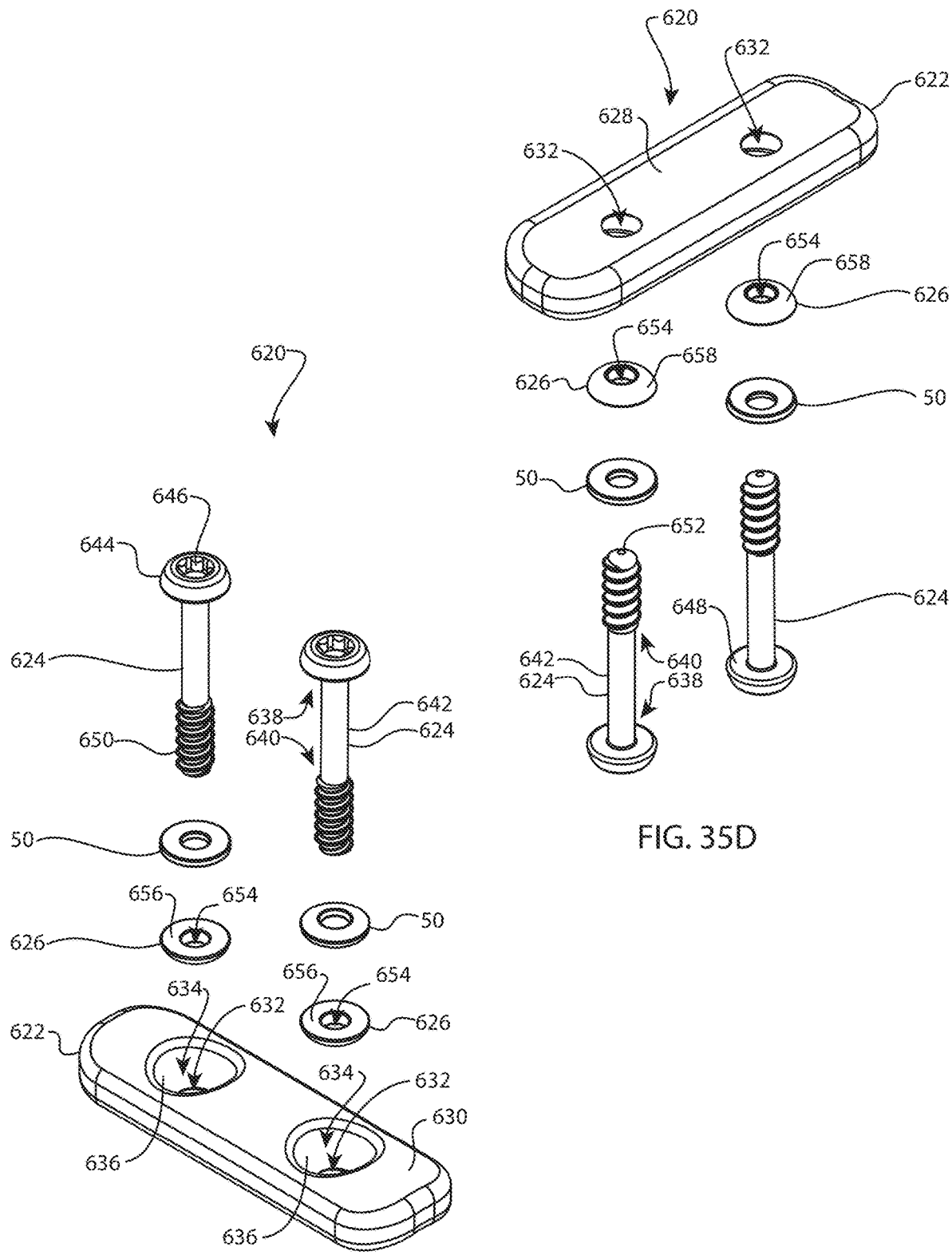
FIG. 35C is an exploded view of the bone plate assembly of FIG. 35A.
FIG. 35D is another exploded view of the bone plate assembly of FIG. 35A from a different viewpoint.

The bone plate 622 includes a bone facing first surface 628 and a second surface 630 opposite the first surface. The first surface 628 and the second surface 630 may be concave, convex, or flat or planar. In FIGS. 35C and 35D, the first surface 628 is concave, while the second surface 630 is convex. An aperture 632 pierces the first and second surfaces 628, 630. Two apertures 632 are shown, although any number of apertures may be included. The aperture 632 may include internal threads. The internal threads may be offset from the center of the aperture 632. In this example, a recess 634 is provided around each aperture 632 extending into the bone plate 622 from the second surface 630. The recess 634 includes a spherical interior surface 636.

The screw 624 may be the screw 402 of bone screw assembly 400 or the screw 432 of bone screw assembly 430. The screw 624 includes a proximal portion 638, a distal portion 640, and a shaft or shank 642 between the proximal portion 638 and the distal portion 640. The proximal portion 638 includes a head 644 with a torque drive feature 646. The torque drive feature 646 may be a protruding feature, such as a hex key, or a recessed feature, such as a hex socket. A hexalobular socket is shown. The head 644 may be integrally formed with the shank 642, or the head 644 may be coupled to the shank 642 by an interconnection such as threads, cross pins, press fit, weld, peening, and the like. The head 644 includes a surface 648 that faces toward the distal portion 640. The surface 648 may be concave, convex, or flat or planar. The distal portion 640 includes external threads 650. The external threads 650 may be specifically designed to engage cortical or cancellous bone. The external threads 650 may be complementary to the internal threads in the aperture 632, if present. The screw 624 may have a blunt, non-cutting distal tip 652. The screw 624 may be inserted into a tapped bone hole. The shank 642 may be smooth. The shank 642 may taper outwardly toward the head 644. The shank 642 has a smaller outer diameter than the head 644 or the major diameter of the external threads 650. The outer diameter of the shank 642 may be the same as the minor diameter of the external threads 650, or nearly the same.

The base 626 may be disc shaped with a central aperture 654 sized to receive the shank 642 so that the base 626 is free to slide along the shank 642. The base 626 has a larger outer diameter than the shank 642, and may have a larger outer diameter than the head 644, the major diameter of the external threads 650, or the aperture 632 of the bone plate 622. However, the outer diameter of the base 626 may be the same as the outer diameter of the head 644 or the major diameter of the external threads 650, or nearly the same. The base 626 includes a first surface 656 and a second surface 658 opposite the first surface. The aperture 654 pierces the first and second surfaces 656, 658. The first and second surfaces 656, 658 may be concave, convex, or flat or planar. In FIGS. 35B and 35C, the first surface 656 is flat or planar, while in FIGS. 35B and 35D, the second surface 658 is convex spherical and complementary to the spherical interior surface 636 of the recess 632 of the bone plate 622. The convex spherical second surface 658 forms a ball and socket joint with the spherical interior surface 636, which permits the screw 624, spring washer 50, and base 626 to polyaxially pivot within the recess 634.

The spring washer 50 may be spring washer 74, 76, 78, 80, 82, 84, 86, or another size consistent with the principles set forth herein. Referring to FIGS. 2C and 35B, the outer diameter (D) 52 may be the same as the outer diameter of the head 644 or the outer diameter of the base 626, or nearly the same. The outer diameter (D) 52 may be less than or equal to the outer diameter of the head 644 or the outer diameter of the base 626 so that the outer lower edge 72 may rest on the surface 648 of the head 644 or the first surface 656 of the base 626. The outer diameter (D) 52 may be larger than the aperture 632 of the bone plate 622. The inner diameter (d) 54 receives the shank 642 of the screw 624 so that the spring washer 50 is free to slide along the shank 642. The inner diameter (d) 54 may be the same size as the aperture 632, although FIG. 35B shows an arrangement in which the inner diameter (d) 54 is smaller than the aperture 632.

When the bone plate assembly 620 is operatively assembled, the shank 642 of the screw 624 is received in the inner diameter (d) 54 of the spring washer 50, the aperture 654 of the base 626, and the aperture 632 of the bone plate 622. The base 626 and the spring washer 50 are received in the recess 634. The base 626 is between the spring washer 50 and the spherical interior surface 636 of the recess 634. The spring washer 50 is between the head 644 of the screw 624 and the base 626. The surfaces 636, 656 may face toward the surface 648 of the head 644 of the screw 624 and the surfaces 628, 658 may face toward the distal portion 640 of the screw 624. The upper surface 62 of the spring washer 50 may face toward the surface 648 and the lower surface 64 of the spring washer 50 may face toward the first surface 656. The outer lower edge 72 of the spring washer 50 may rest on the first surface 656. However, the orientation of the upper and lower surfaces 62, 64 may be reversed so that the outer lower edge 72 of the spring washer 50 rests on the surface 648. Referring to FIG. 35B, the recess 634 is much deeper than the overall height (H) 56 of the spring washer 50 in its flat state plus the overall height of the base 626 so that the entire spring washer 50 and base 626, plus more than half of the overall height of the head 644, are recessed below the second surface 630.

In examples where the head 644 is integral with the screw 624, the spring washer 50 and base 626 may be assembled to the screw 624 by first passing the spring washer 50 and then the base 626 along the external threads 650 from the blunt tip 652 toward the head 644. In this arrangement, the inner diameter (d) 54 and the aperture 654 may be equal to or greater than the minor diameter of the external threads 650 plus one-half of the difference between the major diameter of the external threads and the minor diameter of the external threads. Preferably, the inner diameter (d) 54 and the aperture 654 are optimized to the smallest size that does not damage the inner diameter (d) 54, the aperture 654, or the external threads 416 during assembly. The screw 624, coupled to the spring washer 50 and base 626, may be provided to an end user as a sub-assembly separate from the bone plate 622. The end user may drive the distal portion 640 of the screw 624 through the aperture 632 of the bone plate 622 from the second surface 630 toward the first surface 628 so that the spring washer 50 and the base 626 are in the recess 634 between the surface 648 of the head 644 and the bottom surface 636 of the recess 634.

In examples where the head 644 is coupled to the screw 624 by an interconnection, the spring washer 50 and base 626 may be assembled to the screw 624 by first passing the base 626 and then the spring washer 50 along the shank 642 from the proximal portion 638 toward the distal portion 640. In this arrangement, the inner diameter (d) 54 and the aperture 654 may be equal to or greater than the outer diameter of the interconnection and the shank 642. Preferably, the inner diameter (d) 54 and the aperture 654 are optimized to the smallest size that does not damage the inner diameter (d) 54, the aperture 654, the interconnection, or the shank 642 during assembly, and that permits the spring washer 50 and base 626 to slide freely along the shank 642 in use. The screw 624, with spring washer 50 and base 626, may be provided to an end user as a sub-assembly separate from the bone plate 622. The end user may drive the sub-assembly through the bone plate 622 as described in the preceding paragraph.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. An implant system comprising:
    a screw comprising a distal portion with bone-engaging external threads, a proximal portion opposite the distal portion, and a shank portion between the distal portion and the proximal portion;
    a screw head coupled to the proximal portion of the screw, wherein the screw head comprises an outer diameter and an overall height;
    a spring washer comprising a frustoconical ring having an outer diameter D, an inner diameter d, an upper surface, a lower surface, a central axis of revolution, an outer upper edge of the upper surface at the outer diameter D, an inner upper edge of the upper surface at the inner diameter d, an outer lower edge of the lower surface at the outer diameter D, an inner lower edge of the lower surface at the inner diameter d, an overall height H measured parallel to the central axis of revolution between the inner upper edge and the outer lower edge, an inner height h measured parallel to the central axis of revolution between the inner lower edge and the outer lower edge, and a thickness t, wherein D is less than or equal to 10 mm and t/D is greater than 0.1111 and less than or equal to 0.1500; and
    a base comprising a bone-facing surface, a top surface opposite the bone-facing surface, and a through hole, wherein a major diameter of the external threads of the screw is larger than the through hole of the base, wherein the shank portion of the screw fits through the through hole of the base, wherein the outer diameter of the screw head is larger than the through hole of the base, wherein D is larger than the through hole of the base;
    wherein when the system is operatively assembled, the shank portion of the screw extends through the inner diameter of the spring washer and the through hole of the base so that the spring washer sits on the top surface of the base, the spring washer is between the base and the screw head, and the distal portion of the screw protrudes past the bone-facing surface of the base.

2. The system of claim 1, wherein the screw head is integrally formed with the proximal portion of the screw.

3. The system of claim 1, wherein the screw head is coupled to the proximal portion of the screw by an interconnection selected from the group consisting of threads, cross pins, press fit, weld, and peening.

4. The system of claim 1, wherein a first force of at least 1500 N applied to the spring washer results in a first displacement of the spring washer of less than 0.17 mm, and a second force of at least 1000 N applied to the spring washer results in a second displacement of the spring washer of less than 0.125 mm, wherein the second force is less than the first force.

5. The system of claim 1, wherein a first force between 2000 N and 4000 N applied to the spring washer results in a first displacement of the spring washer, a second force between 1000 N and 3000 N applied to the spring washer results in a second displacement of the spring washer, wherein the second force is less than the first force, and the difference between the first displacement and the second displacement is less than 0.15 mm.

6. The system of claim 1, wherein the bone-facing surface of the base is a convex spherical surface, and the top surface of the base is a flat surface.

7. An implant system comprising:
    a screw comprising a distal portion with bone-engaging external threads, a proximal portion opposite the distal portion, and a shank portion between the distal portion and the proximal portion;
    a screw head coupled to the proximal portion of the screw, wherein the screw head comprises an outer diameter and an overall height;
    a spring washer comprising a frustoconical ring having an outer diameter D, an inner diameter d, an upper surface, a lower surface, a central axis of revolution, an outer upper edge of the upper surface at the outer diameter D, an inner upper edge of the upper surface at the inner diameter d, an outer lower edge of the lower surface at the outer diameter D, an inner lower edge of the lower surface at the inner diameter d, an overall height H measured parallel to the central axis of revolution between the inner upper edge and the outer lower edge, an inner height h measured parallel to the central axis of revolution between the inner lower edge and the outer lower edge, and a thickness t, wherein D is less than or equal to 10 mm and t/D is greater than 0.1111 and less than or equal to 0.1500; and
    a bone plate comprising a bone-facing surface, a top surface opposite the bone-facing surface, and a through hole, wherein the distal portion of the screw and the shank portion of the screw fit through the through hole of the bone plate, wherein the outer diameter of the screw head is larger than the through hole of the bone plate, wherein D is larger than the through hole of the bone plate;
    wherein when the system is operatively assembled, the screw extends through the inner diameter of the spring washer and the through hole of the bone plate so that the spring washer is between the bone-facing surface of the bone plate and the screw head, and the distal portion of the screw protrudes past the bone-facing surface of the bone plate.

8. The system of claim 7, wherein the screw head is integrally formed with the proximal portion of the screw.

9. The system of claim 7, wherein the screw head is coupled to the proximal portion of the screw by an interconnection selected from the group consisting of threads, cross pins, press fit, weld, and peening.

10. The system of claim 7, wherein a first force of at least 1500 N applied to the spring washer results in a first displacement of the spring washer of less than 0.17 mm, and a second force of at least 1000 N applied to the spring washer results in a second displacement of the spring washer of less than 0.125 mm, wherein the second force is less than the first force.

11. The system of claim 7, wherein a first force between 2000 N and 4000 N applied to the spring washer results in a first displacement of the spring washer, a second force between 1000 N and 3000 N applied to the spring washer results in a second displacement of the spring washer, wherein the second force is less than the first force, and the difference between the first displacement and the second displacement is less than 0.15 mm.

12. The system of claim 7, wherein when the system is operatively assembled, the spring washer is between the top surface of the bone plate and the screw head.

13. The system of claim 7, wherein the bone plate comprises a recess indented into the top surface of the bone plate and extending around the through hole.

14. The system of claim 13, wherein when the system is operatively assembled, the spring washer is received in the recess of the bone plate.

15. The system of claim 14, further comprising:
   a base comprising a bottom surface, a top surface opposite the bottom surface, and a through hole;
   wherein when the system is operatively assembled, the screw extends through the through hole of the base, the base is received in the recess of the bone plate, the spring washer sits on the top surface of the base, and the spring washer is between the base and the screw head.

16. The system of claim 15, wherein the recess of the bone plate comprises a concave spherical surface, wherein the bottom surface of the base comprises a convex spherical surface, wherein when the system is operatively assembled, the concave spherical surface forms a ball and socket joint with the convex spherical surface so that the screw, spring washer, and base are polyaxially pivotable within the recess of the bone plate.

* * * * *